United States Patent
Matsuda et al.

(10) Patent No.: US 8,569,493 B2
(45) Date of Patent: Oct. 29, 2013

(54) METHOD FOR TREATING A HOMEOSTASIS-RELATED DISEASE OR GLAUCOMA BY ADMINISTERING A 1,2,3,4-TETRAHYROQUINOXALINE COMPOUND

(75) Inventors: Mamoru Matsuda, Ikoma (JP); Toshiyuki Mori, Ikoma (JP); Masato Nagatsuka, Ikoma (JP); Sachiko Kobayashi, Ikoma (JP); Masatomo Kato, Ikoma (JP); Miwa Takai, Ikoma (JP)

(73) Assignee: Santen Pharmaceutical Co., Ltd., Osaka (JP)

( * ) Notice: Subject to any disclaimer, the term of this patent is extended or adjusted under 35 U.S.C. 154(b) by 0 days.

(21) Appl. No.: 13/364,680

(22) Filed: Feb. 2, 2012

(65) Prior Publication Data

US 2012/0129866 A1 May 24, 2012

Related U.S. Application Data

(62) Division of application No. 12/451,653, filed as application No. PCT/JP2008/059866 on May 29, 2008, now Pat. No. 8,193,187.

(30) Foreign Application Priority Data

May 29, 2007 (JP) .................................. 2007-141568

(51) Int. Cl.
C07D 471/00 (2006.01)

(52) U.S. Cl.
USPC ........................................................ 544/349

(58) Field of Classification Search
USPC ........................................................ 544/349
See application file for complete search history.

(56) References Cited

U.S. PATENT DOCUMENTS

| | | | |
|---|---|---|---|
| 6,153,607 A | 11/2000 | Pflugfelder et al. | |
| 6,340,758 B1 | 1/2002 | Kornberg | |
| 6,369,057 B1 | 4/2002 | Billhardt et al. | |
| 6,852,719 B2 | 2/2005 | Liu et al. | |
| 8,017,775 B2 | 9/2011 | Matsuda et al. | |
| 2004/0266758 A1 | 12/2004 | Hadida-Ruah et al. | |
| 2007/0249011 A1 | 10/2007 | Kudo et al. | |
| 2009/0111807 A1 | 4/2009 | Matsuda et al. | |
| 2009/0298826 A1 | 12/2009 | Matsuda et al. | |
| 2009/0298827 A1 | 12/2009 | Matsuda et al. | |
| 2009/0326009 A1 | 12/2009 | Matsuda et al. | |
| 2010/0056504 A1 | 3/2010 | Matsuda et al. | |
| 2010/0137307 A1 | 6/2010 | Matsuda et al. | |

FOREIGN PATENT DOCUMENTS

| EP | 1 944 290 A1 | 7/2008 |
|---|---|---|
| EP | 2151436 A1 | 2/2010 |
| JP | 2002-193955 A | 7/2002 |
| JP | 2008-74829 A | 4/2008 |
| WO | WO 2004/099192 A2 | 11/2004 |
| WO | WO 2006/015259 A2 | 2/2006 |
| WO | WO 2007/105766 A1 | 9/2007 |
| WO | WO 2008/111632 A1 | 9/2008 |
| WO | WO 2009/035067 A1 | 3/2009 |
| WO | WO 2009/035068 A1 | 3/2009 |

OTHER PUBLICATIONS

George Patani et al., "Bioisosterism: A Rational Approach in Drug Design," Chem. Rev., 1996, 96, 3147-3176.
Hajime Nawat, Sougou Rinsyou, "New Horizons of Glucocorticoid Therapy in the 21$^{st}$ Century," 54(7), 1951-2076 (2005).
Extended European Search Report, including the Supplementary European Search Report and the European Search Opinion, dated Jul. 6, 2011 in EP Application No. 08764835.8 (6 pages).
Jeffrey N. Miner et al., "New and improved glucocorticoid receptor ligands," Expert Opinion on Investagational Drugs, Ashley Publications Ltd., London, GB, vol. 14, No. 12, Dec. 1, 2005, pp. 1527-1545.
McNaught, A.D. et al.: "Aryl groups," Compendium of Chemical Terminology, 2$^{nd}$ Edition, [Online] 1997, XP-002582725, IUPAC.
McNaught, A.D. et al.: "Arenes," Compendium of Chemical Terminology, 2$^{nd}$ Edition, [Online] 1997, XP-002582726, IUPAC.
Jordan, V.C., "Tamoxifen: A Most Unlikely Pioneering Medicine," Nature Reviews: Drug Discovery, 2, 2003, 205.

(Continued)

Primary Examiner — Douglas M Willis
(74) Attorney, Agent, or Firm — Holtz, Holtz, Goodman & Chick PC

(57) ABSTRACT

A method for preventing or treating a metabolic disorder, an inflammatory disease, an autoimmune disease, an allergic disease, a central nervous system disease, a cardiovascular disease, a homeostasis-related disease or glaucoma, involving administering a compound or a salt thereof, the compound having the following formula (1):

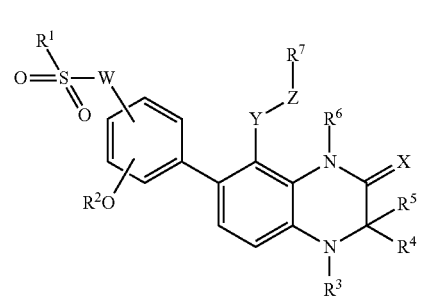

(1)

wherein $R^1$ represents alkyl, cycloalkyl, aryl, heterocyclic or aralkyl; $R^7$ represents cycloalkyl, aryl or heterocyclic; W represents oxygen or $NR^8$, Y represents alkylene, Z represents oxygen, sulfur, OCO or $NR^9$; $R^2$, $R^3$, $R^4$, $R^6$, $R^8$ and $R^9$ represent hydrogen or alkyl.

12 Claims, No Drawings

(56) References Cited

OTHER PUBLICATIONS

Hackam, et al., "Translation of Research Evidence from Animals to Humans," *JAMA*, 296(14), 2006, 1731-1732.

Igaku Daijiten, Nanzando (Nanzando'S Medical Dictionary), The 17th Edition, 1038-1040.

Nagelhouet et al., "Preservation of Tear Film Integrity and Inhibition of Corneal Injury by Dexamethasone in a Rabbit Model of Lacrimal Gland Inflammation-Induced Dry Eye", *J. of Ocular Pharmacology and Therapeutics*, 21, 2, 2005, p. 139-148.

Heath, "Optometric management of anterior segment eye disease: Dry eye and eyelid disease," *Continued Education and Training*, 2007, p. 1-9.

METHOD FOR TREATING A HOMEOSTASIS-RELATED DISEASE OR GLAUCOMA BY ADMINISTERING A 1,2,3,4-TETRAHYROQUINOXALINE COMPOUND

CROSS-REFERENCE TO RELATED APPLICATIONS

This application is a Divisional application of application Ser. No. 12/451,653 filed Nov. 23, 2009 (U.S. Pat. No. 8,193,187), which is the United States national phase application under 35 USC 371 of International application PCT/JP2008/059866 filed May 29, 2008. The entire contents of each of application Ser. No. 12/451,653 and PCT/JP2008/059866 are hereby incorporated by reference herein.

BACKGROUND OF THE INVENTION

1. Field of the Invention

The present invention relates to novel 1,2,3,4-tetrahydroquinoxaline derivatives which have, as a substituent, a phenyl group having a sulfonic acid ester structure or a sulfonic acid amide structure introduced therein or a salt thereof, which are useful as pharmaceuticals. The derivatives have a glucocorticoid receptor binding activity and are useful as glucocorticoid receptor modulators having a nonsteroidal structure (glucocorticoid receptor agonists and/or glucocorticoid receptor antagonists).

2. Description of the Related Art

A glucocorticoid receptor is a 94 kDa ligand-activated intracellular transcriptional regulatory factor that is a member of the nuclear receptor superfamily. This receptor is known to affect the regulation of the metabolism of carbohydrates, proteins, fats and the like, suppression of the immune or inflammatory responses, activation of the central nervous system, regulation of cardiovascular function, and basal and stress-related homeostasis and the like due to it transcriptional regulatory action. As diseases which are considered to be related to glucocorticoid receptor, metabolic disorders such as diabetes and obesity, inflammatory diseases such as enteritis and chronic obstructive pulmonary diseases, autoimmune diseases such as connective tissue diseases, allergic diseases such as asthma, atopic dermatitis and allergic rhinitis, central nervous system diseases such as psychiatric disorders, Alzheimer's disease and drug use disorders, cardiovascular diseases such as hypertension, hypercalcemia, hyperinsulinemia and hyperlipidemia, homeostasis-related diseases causing an abnormality of neuro-immune-endocrine balance, glaucoma and the like are known (SOUGOU RINSYOU, 54(7), 1951-2076 (2005), JP-A-2002-193955).

Therefore, it is considered that a compound having a glucocorticoid receptor binding activity is useful as preventive and/or therapeutic agent for these diseases.

As such a compound having a glucocorticoid receptor binding activity, glucocorticoid receptor agonists synthesized in the living body such as cortisol and corticosterone, synthetic glucocorticoid receptor agonists such as dexamethasone, prednisone and prednisilone, non-selective glucocorticoid receptor antagonists such as RU486 and the like are known (JP-A-2002-193955).

On the other hand, compounds having a 1,2,3,4-tetrahydroquinoxaline structure are disclosed in WO 2004/099192, JP-A-5-148243 and the like. The compounds disclosed in WO 2004/099192 relate to protein thyrosine phosphatase inhibitors essentially having a carboxylic group. A very large number of compounds having 1,2,3,4-tetrahydroquinoxaline structure and the use of them as anti-virus agents are disclosed in JP-A-5-148243. However, 1,2,3,4-tetrahydroquinoxaline derivatives which have, as a substituent, a phenyl group having a sulfonic acid ester structure or a sulfonic acid amide structure introduced therein or a salt thereof have not been specifically disclosed in any of literatures.

SUMMARY OF THE INVENTION

Problems to be Solved

It is a very interesting subject to study the synthesis of novel 1,2,3,4-tetrahydroquinoxaline derivatives which have, as a substituent, a phenyl group having a sulfonic acid ester structure or a sulfonic acid amide structure introduced therein or a salt thereof, and to find a pharmacological action of the derivatives.

Means of Solving Problems

The present inventors conducted the studies of the synthesis of novel 1,2,3,4-tetrahydroquinoxaline derivatives which have, as a substituent, a phenyl group having a sulfonic acid ester structure or a sulfonic acid amide structure introduced therein or a salt thereof having a novel chemical structure, and succeeded in producing a large number of novel compounds.

The chemical structural feature of the derivatives or a salt thereof is a point that they have a sulfonic acid ester structure or a sulfonic acid amide structure in moiety (A) of the following general formula (1).

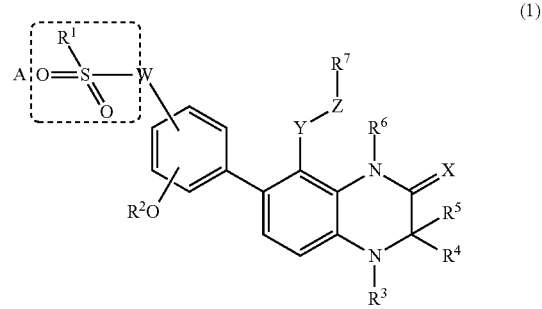

Further, as a result of the study about the pharmacological actions of the derivatives or a salt thereof, the present inventors found that the derivatives or a salt thereof have an excellent glucocorticoid receptor binding activity and are useful as pharmaceuticals, and thus the present invention has been completed.

That is, the present invention relates to compounds represented by the following general formula (1) or a salt thereof and a pharmaceutical composition containing at least one of them. Further, a preferred invention in its pharmaceutical use relates to glucocorticoid receptor modulators. Its target diseases are considered to be metabolic disorders such as diabetes and obesity, inflammatory diseases such as enteritis and chronic obstructive pulmonary diseases, autoimmune diseases such as connective tissue diseases, allergic diseases such as asthma, atopic dermatitis and allergic rhinitis, central nervous system diseases such as psychiatric disorders, Alzheimer's disease and drug use disorders, cardiovascular diseases such as hypertension, hypercalcemia, hyperinsulinemia and hyperlipidemia, homeostasis-related diseases causing an abnormality of neuro-immune-endocrine balance, glaucoma and the like. A particularly preferred invention relates to a preventive and/or a therapeutic agent for these diseases.

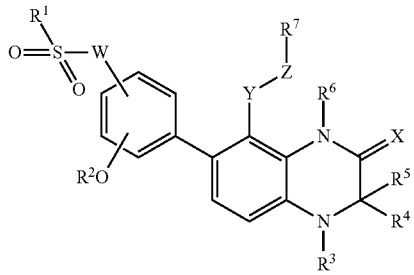

(1)

[R¹ represents a lower alkyl group which may have a substituent, a lower cycloalkyl group which may have a substituent, an aryl group which may have a substituent, a heterocyclic group which may have a substituent or an aralkyl group which may have a substituent;

R² represents a hydrogen atom or a lower alkyl group which may have a substituent;

R³ represents a hydrogen atom or a lower alkyl group which may have a substituent;

R⁴ and R⁵ may be the same or different and represent a hydrogen atom or a lower alkyl group which may have substituent;

R⁶ represents a hydrogen atom or a lower alkyl group which may have a substituent;

R⁷ represents a hydrogen atom, a lower alkyl group which may have a substituent, a lower alkenyl group which may have a substituent, a lower alkynyl group which may have a substituent, a lower cycloalkyl group which may have a substituent, an aryl group which may have a substituent or a heterocyclic group which may have a substituent;

W represents an oxygen atom, a sulfur atom or NR⁸;

R⁸ represents a hydrogen atom or a lower alkyl group which may have a substituent;

X represents an oxygen atom or a sulfur atom;

Y represents a lower alkylene group which may have a substituent;

Z represents an oxygen atom, a sulfur atom, NR⁹, OCO or OSO₂;

R⁹ represents a hydrogen atom or a lower alkyl group which may have a substituent. Hereinafter the same shall apply.]

DETAILED DESCRIPTION OF THE INVENTION

The present invention provides 1,2,3,4-tetrahydroquinoxaline derivatives which have, as a substituent, a phenyl group having a sulfonic acid ester structure or a sulfonic acid amide structure introduced therein or a salt thereof (hereinafter referred to as "the present compound"), which are useful as pharmaceuticals. The present compound has an excellent glucocorticoid receptor binding activity and is useful as a glucocorticoid receptor modulator. It is expected that the present compound is particularly useful as a preventive or therapeutic agent for metabolic disorders such as diabetes and obesity, inflammatory diseases such as enteritis and chronic obstructive pulmonary diseases, autoimmune diseases such as connective tissue diseases, allergic diseases such as asthma, atopic dermatitis and allergic rhinitis, central nervous system diseases such as psychiatric disorders, Alzheimer's disease and drug use disorders, cardiovascular diseases such as hypertension, hypercalcemia, hyperinsulinemia and hyperlipidemia, homeostasis-related diseases causing an abnormality of neuro-immune-endocrine balance, glaucoma and the like.

BEST MODE FOR CARRYING OUT THE INVENTION

Hereinafter, definitions of terms and phrases (atoms, groups and the like) used in this specification will be described in detail. In addition, when the definition of terms and phrases is applied to the definition of another terms and phrases, a desirable range and the particularly desirable range of each definition is also applied.

The "halogen atom" refers to a fluorine, chlorine, bromine or iodine atom.

The "lower alkyl group" refers to a straight chain or branched alkyl group having 1 to 8 carbon atoms, preferably a straight chain or branched alkyl group having 1 to 6 carbon atoms, more preferably a straight chain or branched alkyl group having 1 to 4 carbon atoms. Specific examples thereof include methyl, ethyl, n-propyl, n-butyl, n-pentyl, n-hexyl, n-heptyl, n-octyl, isopropyl, isobutyl, sec-butyl, tert-butyl and isopentyl groups and the like.

The "lower alkenyl group" refers to a straight chain or branched alkenyl group having 2 to 8 carbon atoms, preferably a straight chain or branched alkenyl group having 2 to 6 carbon acorns, more preferably a straight chain or branched alkenyl group having 2 to 4 carbon atoms. Specific examples thereof include vinyl, propenyl, butenyl, pentenyl, hexenyl, heptenyl, octenyl, isopropenyl, 2-methyl-1-propenyl and 2-methyl-2-butenyl groups and the like.

The "lower alkynyl group" refers to a straight chain or branched alkynyl group having 2 to 8 carbon atoms, preferably a straight chain or branched alkynyl group having 2 to 6 carbon atoms, more preferably a straight chain or branched alkynyl group having 2 to 4 carbon atoms. Specific examples thereof include ethynyl, propynyl, butynyl, pentynyl, hexynyl, heptynyl, octynyl, isobutynyl and isopentynyl groups and the like.

The "lower cycloalkyl group" refers to a cycloalkyl group having 3 to 8 carbon atoms, preferably a cycloalkyl group having 3 to 6 carbon atoms. Specific examples thereof include cyclopropyl, cyclobutyl, cyclopentyl, cyclohexyl, cyclopentyl and cyclooctyl groups.

The "aryl group" refers to a residue formed by removing one hydrogen atom from a monocyclic aromatic hydrocarbon group, or bicyclic or tricyclic condensed polycyclic aromatic hydrocarbon having 6 to 14 carbon atoms. Specific examples thereof include phenyl, naphthyl, anthryl and phenanthryl groups and the like.

The "heterocyclic group" refers to a residue formed by removing a hydrogen atom from a saturated or unsaturated monocyclic heterocyclic ring having one or a plurality of heteroatoms selected from a nitrogen atom, an oxygen atom and a sulfur atom in the ring or a bicyclic or tricyclic condensed polycyclic heterocyclic ring.

Specific examples of the saturated monocyclic heterocyclic ring include pyrrolidine, pyrazolidine, imidazolidine, triazolidine, piperidine, hexahydropyridazine, hexahydropyrimidine, piperazine, homopiperidine and homopiperazine rings and the like having at least a nitrogen atom in the ring, tetrahydrofuran and tetrahydropyran rings and the like having at least an oxygen atom in the ring, tetrahydrothiophene and tetrahydrothiopyran rings and the like having at least a sulfur atom in the ring, oxazolidine, isoxazolidine and morpholine rings and the like having at least a nitrogen atom and an oxygen atom in the ring, and thiazolidine, isothiazolidine and thiomorpholine rings and the like having at least a nitrogen atom and a sulfur atom in the ring.

Further, such a saturated monocyclic heterocyclic ring can be condensed with a benzene ring or the like to form a bicyclic or tricyclic condensed polycyclic heterocyclic ring such as a dihydroindole, dihydroindazole, dihydrobenzimidazole, tetrahydroquinoline, tetrahydroisoquinoline, tetrahydrocinnoline, tetrahydrophthalazine, tetrahydroquinazoline, tetrahydroquinoxaline, dihydrobenzofuran, dihydroisobenzofuran, chromane, isochromane, dihydrobenzothiophene, dihydroisobenzothiophene, thiochromane, isothiochromane, dihydrobenzoxazole, dihydrobenzisoxazole, dihydrobenzoxazine, dihydrobenzothiazole, dihydrobenzisothiazole, dihydrobenzothiazine, xanthene, 4a-carbazole, or perimidine ring and the like.

Specific examples of the unsaturated monocyclic heterocyclic ring include dihydropyrrole, pyrrole, dihydropyrazole, pyrazole, dihydroimidazole, imidazole, dihydrotriazole, triazole, tetrahydropyridine, dihydropyridine, pyridine, tetrahydropyridazine, dihydropyridazine, pyridazine, tetrahydropyrimidine, dihydropyrimidine, pyrimidine, tetrahydropyrazine, dihydropyrazine and pyrazine rings and the like having at least a nitrogen atom in the ring, dihydrofuran, furan, dihydropyran and pyran rings and the like having at least an oxygen atom in the ring, dihydrothiophene, thiophene, dihydrothiopyran and thiopyran rings and the like having at least a sulfur atom in the ring, dihydrooxazole, oxazole, dihydroisoxazole, isoxazole, dihydrooxazine and oxazine rings and the like having at least a nitrogen atom and an oxygen atom in the ring, dihydrothiazole, thiazole, dihydroisothiazole, isothiazole, dihydrothiazine and thia zinc rings and the like having at least a nitrogen atom and a sulfur atom in the ring.

Further, such an unsaturated monocyclic heterocyclic ring can be condensed with a benzene ring or the like to form a bicyclic or tricyclic condensed polycyclic heterocyclic ring such as an indole, indazole, benzimidazole, benzotriazole, dihydroquinoline, quinoline, dihydroisoquinoline, isoquinoline, phenanthridine, dihydrocinnoline, cinnoline, dihydrophthalazine, phthalazine, dihydroquinazoline, quinazoline, dihydroquinoxaline, quinoxaline, benzofuran, isobenzofuran, chromene, isochromene, benzothiophene, isobenzothiophene, thiochromene, isothiochromene, benzoxazole, benzisoxazole, benzoxazine, benzothiazole, benzisothiazole, benzothiazine, phenoxanthin, carbazole, β-carboline, phenanthridine, acridine, phenanthroline, phenazine, phenothiazine or phenoxazine ring and the like.

The "aralkyl group" refers to a group formed by replacing the hydrogen atom of a lower alkyl group with an aryl group. Specific examples thereof include benzyl, phenethyl, phenylpropyl, naphthylmethyl, anthrylmethyl and phenanthrylmethyl groups and the like.

The "lower alkoxy group" refers to a group formed by replacing the hydrogen atom of a hydroxy group with a lower alkyl group. Specific examples thereof include methoxy, ethoxy, n-propoxy, n-butoxy, n-pentoxy, n-hexyloxy, n-heptyloxy, n-octyloxy, isopropoxy, isobutoxy, sec-butoxy, tert-butoxy and isopentoxy groups and the like.

The "aryloxy group" refers cc a group formed by replacing the hydrogen atom of a hydroxy group with an aryl group. Specific examples thereof include phenoxy, naphthoxy, anthryloxy and phenanthryloxy groups and the like.

The "lower alkoxycarbonyl group" refers to a group formed by replacing the hydrogen atom of a formyl group with a lower alkoxy group. Specific examples thereof include methoxycarbonyl, ethoxycarbonyl, n-propoxycarbonyl, n-butoxycarbonyl, n-pentoxycarbonyl, n-hexyloxycarbonyl, n-heptyloxycarbonyl, n-octyloxycarbonyl, isopropoxycarbonyl, isobutoxycarbonyl, sec-butoxycarbonyl, tert-butoxycarbonyl and isopentoxycarbonyl groups and the like.

The "aryloxycarbonyl group" refers to a group formed by replacing the hydrogen atom of a formyl group with an aryloxy group. Specific examples thereof include phenoxycarbonyl, naphthoxycarbonyl, anthryloxycarbonyl and phenanthryloxycarbonyl groups and the like.

The "lower alkylene group" refers to a straight chain or branched alkylene group having 1 to 8 carbon atoms, preferably a straight chain or branched alkylene group having 1 to 6 carbon atoms, more preferably a straight chain or branched alkylene group having 1 to 4 carbon atoms. Specific examples thereof include methylene, ethylene, trimethylene, tetramethylene, pentamethylene, hexamethylene, heptamethylene, octamethylene, methylmethylene and ethylmethylene groups and the like.

The "lower alkylamino group" refers to a group formed by replacing either or both of the hydrogen atoms of an amino group with a lower alkyl group. Specific examples thereof include methylamino, ethylamino, propylamino, dimethylamino, diethylamino and ethyl(methyl)amino groups and the like.

The "lower alkylamino group substituted with a lower alkylamino group" refers to a lower alkylamino group substituted with one or a plurality of lower alkylamino groups.

The "lower alkylamino group substituted with an aryl group" refers to a lower alkylamino group substituted with one or a plurality of aryl groups.

The "lower alkyl group which may have a substituent", "lower alkenyl group which may have a substituent", "lower alkynyl group which may have a substituent" and "lower alkylene group which may have a substituent" refer to a "lower alkyl group", a "lower alkenyl group", a "lower alkynyl group" and a "lower alkylene group" which may have one or a plurality of substituents selected from the following $\alpha^1$ group, respectively.

[$\alpha^1$ Group]

A halogen atom, a lower cycloalkyl group, an aryl group, a heterocyclic group, a hydroxy group, a lower alkoxy group, an aryloxy group, a carboxy croup, a lower alkoxycarbonyl group, an aryloxycarbonyl group, a lower alkylamino group, a lower alkylamino group substituted with a lower alkylamino group, a lower alkylamino group substituted with an aryl group, a nitro group and a cyano group.

The "lower cycloalkyl group which may have a substituent", "aryl group which may have a substituent", "heterocyclic group which may have a substituent" and "aralkyl group which may have a substituent" refer to a "lower cycloalkyl group", an "aryl group", a "heterocyclic group" and an "aralkyl group" which may have one or a plurality of substituents selected from the following $\beta^1$ group, respectively.

[$\beta^1$ Group]

A halogen atom, a lower alkyl group, a lower alkyl group substituted with a halogen atom, a lower alkenyl group, a lower alkynyl group, a lower cycloalkyl group, an aryl group, a heterocyclic group, a hydroxy group, a lower alkoxy group, a lower alkoxy group substituted with a halogen atom, an aryloxy group, a carboxy group, a lower alkoxycarbonyl group, an aryloxycarbonyl group, a nitro group and a cyano group.

The term "a plurality of groups" as used in this invention means that each group may be the same or different and the number of groups is preferably 2 or 3, and 2 is particularly preferable. Further, a hydrogen atom and a halogen atom are also included in the concept of the "group".

The "glucocorticoid receptor modulator" as used in this invention refers to a modulator that exhibits a pharmaceutical action by binding to a glucocorticoid receptor. Examples thereof include glucocorticoid receptor agonists, glucocorticoid receptor antagonists and the like.

The "salt" of the present compound is not particularly limited as long as it is a pharmaceutically acceptable salt. Specific examples thereof include, salts with an inorganic acid such as hydrochloric acid, hydrobromic acid, hydroiodic acid, nitric acid, sulfuric acid, phosphoric acid or the like; salts with an organic acid such as acetic acid, fumaric acid, maleic acid, succinic acid, citric acid, tartaric acid, adipic acid, gluconic acid, glucoheptonic acid, glucuronic acid, terephthalic acid, methanesulfonic acid, lactic acid, hippuric acid, 1,2-ethanedisulfonic acid, isethionic acid, lactobionic acid, oleic acid, pamoic acid, polygalacturonic acid, stearic acid, tannic acid, trifluoromethanesulfonic acid, benzenesulfonic acid, p-toluenesulfonic acid, lauryl sulfate ester, methyl sulfate, naphthalenesulfonic acid, sulfosalicylic acid or the like; quaternary ammonium salts with methyl bromide, methyl iodide or the like; salts with a halogen ion such as a bromine ion, a chlorine ion, an iodine ion or the like; salts with an alkali metal such as lithium, sodium, potassium or the like; salts with an alkaline earth metal such as calcium, magnesium or the salts with a metal such as iron, zinc or the like; salts with ammonia; salts with an organic amine such as triethylenediamine, 2-aminoethanol, 2,2-iminobis(ethanol), 1-deoxy-1-(methylamino)-2-D-sorbitol, 2-amino-2-(hydroxymethyl)-1,3-propanediol, procaine, N,N-bis(phenylmethyl)-1,2-ethanediamine or the like.

The present compound may form hydrates or solvates.

In the case where there are geometrical isomers or optical isomers in the present compound, these isomers are also included in the scope of the present invention.

In the case where there are proton tautomers in the present compound, these tautomers are also included in the scope of the present invention.

In the case where there are polymorphism and polymorphism group (polymorphism system) in the present compound, these polymorphism and polymorphism group (polymorphism system) are also included in the scope of the present invention.

"Polymorphism group (polymorphism system)" herein means each crystal form in each step where the crystal form changes depending on conditions and states (the states also include a state of drug formulation) of manufacture, crystallization and preservation and the like, and the entire process.

(a) Examples of the present compound include compounds in which the respective groups are groups as defined below and salts thereof in the compounds represented by the general formula (1) and salts thereof.

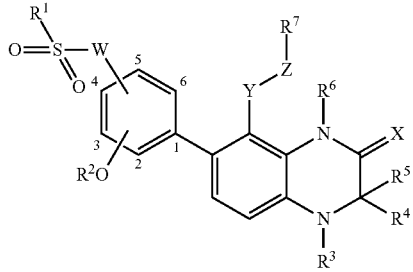

(1)

(a1) $R^1$ represents a lower alkyl group which may have a substituent, a lower cycloalkyl group which may have a substituent, an aryl group which may have a substituent, heterocyclic group which may have a substituent or an aralkyl group which may have a substituent; and/or (a2) $R^2$ represents a hydrogen atom or a lower alkyl group which may have a substituent; and/or (a3) $R^3$ represents a hydrogen atom or a lower alkyl group which may have a substituent; and/or (a4) $R^4$ and $R^5$ may be the same or different and represent a hydrogen atom or a lower alkyl group which may have a substituent; and/or (a5) $R^6$ represents a hydrogen atom or a lower alkyl group which may have a substituent; and/or (a6) $R^7$ represents a hydrogen atom, a lower alkyl group which may have a substituent, a lower alkenyl group which may have a substituent, a lower alkynyl group which have a substituent, a lower cycloalkyl group which may have a substituent, an aryl group which may have a substituent or a heterocyclic group which may have a substituent; and/or (a7) W represents an oxygen atom, a sulfur atom or $NR^8$; and/or (a8) $R^8$ represents a hydrogen atom of a lower alkyl group which may have a substituent; and/or (a9) X represents an oxygen atom or a sulfur atom; and/or (a10) Y represents a lower alkylene group which may have a substituent; and/or (a11) Z represents an oxygen atom, a sulfur atom, $NR^9$, OCO or $OSO_2$; and/or (a12) $R^9$ represents a hydrogen atom or a lower alkyl group which may have a substituent.

That is, in the compounds represented by the general formula (1), examples of the present compound include compounds that comprise a combination of the above (a1), (a2) (a3) (a4) (a5), (a6), (a7), (a8), (a9), (a10), (a11) and (a12), and salts thereof.

(b) Preferred examples of the present compound include compounds in which the respective groups are groups as defined below and salts thereof in the compounds represented by the general formula (1) and salts thereof.

(b1) $R^1$ represents a lower alkyl group, a lower cycloalkyl group, an aryl group, a heterocyclic group or an aralkyl group;

in the case where $R^1$ is a lower alkyl group, the lower alkyl group may have one or a plurality of groups selected from a halogen atom, a heterocyclic group, a carboxy group, a lower alkoxycarbonyl group, a lower alkylamino group, a lower alkylamino group substituted with a lower alkylamino group and a lower alkylamino group substituted with an aryl group as substituent(s);

in the case where $R^1$ is an aryl group, a heterocyclic group or an aralkyl group, the aryl group, heterocyclic group or aralkyl group may have one or a plurality of groups selected from a halogen atom, a lower alkyl group, a hydroxyl group and a lower alkoxy group as substituent(s); and/or (b2) $R^2$ represents a hydrogen atom or a lower alkyl group; and/or (b3) $R^3$ represents a hydrogen atom or a lower alkyl group; and/or (b4) $R^4$ and $R^5$ may be the same or different and represent a hydrogen atom or a lower alkyl group; and/or (b5) $R^5$ represents a hydrogen atom or a lower alkyl group; and/or (b6) $R^7$ represents a lower cycloalkyl group, an aryl group or a heterocyclic group;

in the case where $R^7$ is an aryl group or a heterocyclic group, the aryl group or heterocyclic group may have one or a plurality of groups selected from a halogen atom, a lower alkyl group, a hydroxyl group, a lower alkoxy group and a nitro group as substituent(s); and/or (b7) W represents an oxygen atom or $NR^8$; and/or (b8) $R^8$ represents a hydrogen atom or a lower alkyl group; and/or (b9) X represents an oxygen atom or a sulfur atom; and/or (b10) Y represents a lower alkylene group; and/or (b11) Z represents an oxygen atom, a sulfur atom, $NR^9$ or OCO; and/or (b12) $R^9$ represents a hydrogen atom or a lower alkyl group.

That is, in the compounds represented by the general formula (1), preferred examples of the present compound include compounds that comprise one or a combination of two or more selected from the above (b1), (b2), (b3), (b4), (b5), (b6), (b7), (b8), (b9), (b10), (b11) and (b12), and salts thereof. Further, the selected conditions may combined with conditions (a).

(c) More preferred examples of the present compound include compounds in which the respective groups are groups as defined below and salts thereof in the compounds represented by the general formula (1) and salts thereof.

(c1) $R^1$ represents a lower alkyl group, a lower cycloalkyl group, an aryl group, a heterocyclic group or an aralkyl group;

in the case where $R^1$ is a lower alkyl group, the lower alkyl group may have one or a plurality of groups selected from halogen atom, a heterocyclic group, a lower alkoxycarbonyl group, a lower alkylamino group, a lower alkylamino group substituted with a lower alkylamino group and a lower alkylamino group substituted with an aryl group as substituent(s);

in the case where $R^1$ is an aryl group, the aryl group may have one or a plurality of groups selected from a halogen atom, a lower alkyl group and a lower alkoxy group as substituent(s);

in the case where $R^1$ is an aralkyl group, the aralkyl group may have one or a plurality of groups selected from a halogen atom and a lower alkyl group as substituent(s); and/or (c2) $R^2$ represents a lower alkyl group; and/or (c3) $R^3$ represents a hydrogen atom; and/or (c4) $R^4$ and $R^5$ represent a lower alkyl group; and/or (c5) $R^6$ represents a lower alkyl group; and/or (c6) $R^7$ represents an aryl group or heterocyclic group;

in the case where $R^7$ is an aryl group, the aryl group may have one or a plurality of groups selected from a halogen atom, a lower alkyl group, a lower alkoxy group and a nitro group as substituent(s);

in the case where $R^7$ is a heterocyclic group, the heterocyclic group may have one or a plurality of lower alkyl group as substituent(s); and/or (c7) W represents an oxygen atom or $NR^8$; and/or (c8) $R^8$ represents a hydrogen atom; and/or (c9) X represents an oxygen atom; and/or (c10) Y represents a lower alkylene group; and/or (c11) Z represents an oxygen atom, $NR^9$ or OCO; and/or (c12) $R^9$ represents a hydrogen atom.

That is, in the compounds represented by the general formula (1), more preferred examples of the present compound include compounds that comprise one or a combination of two or more selected from the above (c1), (c2), (c3), (c4), (c5), (c6), (c7), (c8), (c9), (c10), (c11) and (c12), and salts thereof. Further, the selected conditions may combined with conditions (a) and/or (b).

(d) One of furthermore preferred examples of the present compound includes compounds which satisfy the following condition and salts thereof.

The compounds in which $R^4$ and $R^5$ are a methyl group in the general formula (1) and which satisfy the above conditions (a), (b) and/or (c), and salts thereof.

(e) One of further more preferred examples of the present compound includes compounds which satisfy the following condition and salts thereof.

The compounds in which $R^6$ is a methyl group in the general formula (1) and which satisfy the above conditions (a), (b) and/or (c), and salts thereof.

(f) One of further more preferred examples of the ent compound includes compounds which satisfy the following condition and salts thereof.

The compounds in which the heterocyclic group of $R^7$ is thiophene in the general formula (1) and which satisfy the above conditions (a), (b) and/or (c), and salts thereof.

(g) One of further more preferred examples of the present compound includes compounds which satisfy the following condition and salts thereof.

The compounds in which X is an oxygen atom in the general formula (1) and which satisfy the above conditions (a) (b) and/or (c), and salts thereof.

(h) One of further more preferred examples of the present compound includes compounds which satisfy the following condition and salts thereof.

The compounds in which Y is a methylene group in the general formula (1) and which satisfy the above conditions (a), (b) and/or (c), and salts thereof.

(i) About the substitution position of $R^1SO_2$—W— in the present compound, it is preferred that the substitution position of $R^1SO_2$—W— is 4- or 5-position of the benzene ring in the general formula (1), and it is more preferred that the substitution position is 4-position.

The compounds which satisfy this condition (i) and the above conditions (a), (b) and/or (c), and salts thereof are particularly preferred.

(j) About the substitution position of $R^2O$— in the present compound, it is preferred that the substitution position of $R^2O$— is 2-position of the benzene ring in the general formula (1).

The compounds which satisfy this condition (j) and the above conditions (a), (b) and/or (c), and salts thereof are particularly preferred.

(k) Particularly preferred specific examples of the present compound include the following compounds and salts thereof.

8-(5-Fluoro-2-methylphenoxymethyl)-7-(2-methoxy-4-methylsulfonyloxyphenyl)-1,3,3-trimethyl-3,4-dihydro-1H-quinoxalin-2-one, 8-(5-Fluoro-2-methylphenoxymethyl)-7-(2-methoxy-4-phenylsulfonyloxyphenyl)-1,3,3-trimethyl-3,4-dihydro-1H-quinoxalin-2-one, 8-(5-Fluoro-2-methylphenoxymethyl)-7-(2-methoxy-4-trifluoromethylsulfonyloxyphenyl)-1,3,3-trimethyl-3,4-dihydro-1H-quinoxalin-2-one, 8-(5-Fluoro-2-methylphenoxymethyl)-7-(2-methoxy-4-propylsulfonyloxyphenyl)-1,3,3-trimethyl-3,4-dihydro-1H-quinoxalin-2-one, 8-(5-Fluoro-2-methylphenoxymethyl)-7-[2-methoxy-4-(furan-2-ylsulfonyloxy)phenyl]-1,3,3-trimethyl-3,4-dihydro-1H-quinoxalin-2-one, 7-(2-Methoxy-4-methylsulfonyloxyphenyl)-8-(5-methylthiophen-2-ylcarbonyloxymethyl)-1,3,3-trimethyl-3,4-dihydro-1H-quinoxalin-2-one, 7-[4-(2-Chlorophenylsulfonyloxy)-2-methoxyphenyl]-8-(5-fluoro-2-methylphenoxymethyl)-1,3,3-trimethyl-3,4-dihydro-1H-quinoxalin-2-one, 7-(4-Benzylsulfonyloxy-2-methoxyphenyl)-8-(5-fluoro-2-methylphenoxymethyl)-1,3,3-trimethyl-3,4-dihydro-1H-quinoxalin-2-one, 8-(5-Fluoro-2-methylphenoxymethyl)-7-[2-methoxy-4-(2-methoxycarbonylethylsulfonyloxy)phenyl]-1,3,3-trimethyl-3,4-dihydro-1H-quinoxalin-2-one, 7-(4-Butylsulfonyloxy-2-methoxyphenyl)-8-(5-fluoro-2-methylphenoxymethyl)-1,3,3-trimethyl-3,4-dihydro-1H-quinoxalin-2-one, 7-(4-Ethylsulfonyloxy-2-methoxyphenyl)-8-(5-fluoro-2-methylphenoxymethyl)-1,3,3-trimethyl-3,4-dihydro-1H-quinoxalin-2-one, 8-(5-Fluoro-2-methylphenoxymethyl)-7-(4-isopropylsulfonyloxy-2-methoxyphenyl)-1,3,3-trimethyl-3,4-dihydro-1H-quinoxalin-2-one, 8-(5-Fluoro-2-methylphenoxymethyl)-7-[2-methoxy-4-(4-methylbenzylsulfonyloxy)phenyl]-1,3,3-trimethyl-3,4-dihydro-1H-quinoxalin-2-one, 7-[4-(4-Chlorobenzylsulfonyloxy)-2-methoxyphenyl]-8-(5-fluoro-2-methylphenoxymethyl)-1,3,3-trimethyl-3,4-dihydro-1H-quinoxalin-2-one, 8-(5-Fluoro-2-methylphenoxymethyl)-7-(4-isobutylsulfonyloxy-2-methoxyphenyl-1,3,3-trimethyl-3,4-dihydro-1H-quinoxalin-2-one, 8-(5-Fluoro-2-methylphenoxymethyl)-7-[2-methoxy-4-(3,3,3-trifluoropropylsulfonyloxy)phenyl]-1,3,3-trimethyl-3,4-dihydro-1H-quinoxalin-2-one, 7-(4-Cyclopropylsulfonyloxy-2-methoxyphenyl)-8-(5-fluoro-2-methylphenoxymethyl)-1,3,3-trimethyl-3,4-dihydro-1H-quinoxalin-2-one, 8-(5-Fluoro-2-methylphenoxymethyl)-7-(2-methoxy-4-methylsulfonylaminophenyl)-1,3,3-trimethyl-3,4-dihydro-1H-quinoxalin-2-one, 7-[4-(2-Chlorobenzylsulfonyloxy)-2-methoxyphenyl]-8-(5-fluoro-2-methylphenoxymethyl)-1,3,3-trimethyl-3,4-dihydro-1H-quinoxalin-2-one, 8-(5-Fluoro-2-methylphenoxymethyl)-7-[2-methoxy-4-(2-methylbenzylsulfonyloxy)phenyl]-1,3,3-trimethyl-3,4-dihydro-1H-quinoxalin-2-one, 7-(4-Cyclopentylsulfonyloxy-2-methoxyphenyl)-8-(5-fluoro-2-methylphenoxymethyl)-1,3,3-trimethyl-3,4-dihydro-1H-quinoxalin-2-one, 7-(4-Cyclohexylsulfonyloxy-2-methoxyphenyl)-8-(5-fluoro-2-methylphenoxymethyl)-1,3,3-trimethyl-3,4-dihydro-1H-quinoxalin-2-one, 8-(5-Fluoro-2-methylphenoxymethyl)-7-[2-methoxy-4-(3-methylbenzylsulfonyloxy)phenyl]-1,3,3-trimethyl-3,4-dihydro-1H-quinoxalin-2-one, 7-(4-Cyclopropylsulfonyloxy-2-methoxyphenyl)-8-(5-methylthiophen-2-ylcarbonyloxymethyl)-1,3,3-trimethyl-3,4-dihydro-1H-quinoxalin-2-one, 7-[2-Methoxy-4-(3,3,3-trifluoropropylsulfonyloxy)phenyl]-8-(5-methylthiophen-2-ylcarbonyloxymethyl)-1,3,3-trimethyl-3,4-dihydro-1H-quinoxalin-2-one, 7-(4-Isobutylsulfonyloxy-2-methoxyphenyl)-8-(5-methylthiophen-2-ylcarbonyloxymethyl)-1,3,3-trimethyl-3,4-dihydro-1H-quinoxalin-2-one, 7-(2-Methoxy-4-propylsulfonyloxyphenyl)-8-(5-methylthiophen-2-ylcarbonyloxymethyl)-1,3,3-trimethyl-3,4-dihydro-1H-quinoxalin-2-one, 7-(4-Isopropylsulfonyloxy-2-methoxyphenyl)-8-(5-methylthiophen-2-ylcarbonyloxymethyl)-1,3,3-trimethyl-3,4-dihydro-1H-quinoxalin-2-one, 7-(4-Cyclopentylsulfonyloxy-2-methoxyphenyl)-8-(5-methylthiophen-2-ylcarbonyloxymethyl)-1,3,3-trimethyl-3,4-dihydro-1H-quinoxalin-2-one, 7-(2-Methoxy-4-methylsulfonyloxyphenyl)-8-(2-methoxyphenylaminomethyl)-1,3,3-trimethyl-3,4-dihydro-1H-quinoxalin-2-one, 7-(4-Cyclopropylsulfonyloxy-2-methoxyphenyl)-8-(2-methoxyphenylaminomethyl)-1,3,3-trimethyl-3,4-dihydro-1H-quinoxalin-2-one, 7-(2-Methoxy-4-methylsulfonyloxyphenyl)-8-(2-methoxy-5-nitrophenoxymethyl)-1,3,3-trimethyl-3,4-dihydro-1H-quinoxalin-one, 8-(2-Methoxy-5-nitrophenoxymethyl)-7-[2-methoxy-4-(3,3,3-trifluoropropylsulfonyloxy)phenyl]-1,3,3-trimethyl-3,4-dihydro-1H-quinoxalin-2-one, 7-(4-Isopropylsulfonyloxy-2-methoxyphenyl)-8-(2-methoxy-5-nitrophenoxymethyl)-1,3,3-trimethyl-3,4-dihydro-1H-quinoxalin-2-one, 7-(4-Cyclopropylsulfonyloxy-2-methoxyphenyl)-8-(2-methoxy-5-nitrophenoxymethyl)-1,3,3-trimethyl-3,4-dihydro-1H-quinoxalin-2-one, 7-(4-Cyclopropylsulfonyloxy-2-methoxyphenyl)-8-(2-methyl-5-nitrophenoxymethyl)-1,3,3-trimethyl-3,4-dihydro-1H-quinoxalin-2-one, 7-[2-Methoxy-4-(3,3,3-trifluoropropylsulfonyloxy)phenyl]-8-(2-methyl-5-nitrophenoxymethyl)-1,3,3-trimethyl-3,4-dihydro-1H-quinoxalin-2-one, 7-(2-Methoxy-4-methylsulfonyloxyphenyl)-8-(2-methyl-5-nitrophenoxymethyl)-1,3,3-trimethyl-3,4-dihydro-1H-quinoxalin-2-one, 7-(2-Methoxy-4-propylsulfonyloxyphenyl)-8-(4-methylbenzoyloxymethyl)-1,3,3-trimethyl-3,4-dihydro-1H-quinoxalin-2-one, 8-(2-Methoxyphenylaminomethyl)-7-[2-methoxy-4-(3,3,3-trifluoropropylsulfonyloxy)phenyl]-1,3,3-trimethyl-3,4-dihydro-1H-quinoxalin-2-one, 7-(4-Isobutylsulfonyloxy-2-methoxyphenyl)-8-(2-methoxyphenylaminomethyl)-1,3,3-trimethyl-3,4-dihydro-1H-quinoxalin-2-one, 7-(4-Cyclopropylsulfonyloxy-2-methoxyphenyl)-8-(5-fluoro-2-methylphenylaminomethyl)-1,3,3-trimethyl-3,4-dihydro-1H-quinoxalin-2-one, 8-(5-Fluoro-2-methylphenylaminomethyl)-7-(2-methoxy-4-propylsulfonyloxyphenyl)-1,3,3-trimethyl-3,4-dihydro-1H-quinoxalin-2-one, 7-(4-Benzylaminopropylsulfonyloxy-2-methoxyphenyl)-8-(5-fluoro-2-methylphenoxymethyl)-1,3,3-trimethyl-3,4-dihydro-1H-quinoxalin-2-one, 8-(5-Fluoro-2-methylphenoxymethyl)-7-[2-methoxy-4-(3-propylaminopropylsulfonyloxy)phenyl]-1,3,3-trimethyl-3,4-dihydro-1H-quinoxalin-2-one, 8-(5-Fluoro-2-methylphenoxymethyl)-7-[2-methoxy-4-(morpholin-4-yl)propylsulfonyloxyphenyl]-1,3,3-trimethyl-3,4-dihydro-1H-quinoxalin-2-one, 8-(5-Fluoro-2-methylphenoxymethyl)-7-[2-methoxy-4-(piperidin-1-yl)chloropropylsulfonyloxyphenyl]-1,3,3-trimethyl-3,4-dihydro-1H-quinoxalin-2-one, 8-(5-Fluoro-2-methylphenoxymethyl)-7-[2-methoxy-4-(N-dimethylaminoethyl-N-methyl)aminopropylsulfonyloxyphenyl]-1,3,3-trimethyl-3,4-dihydro-1H-quinoxalin-2-one, and 8-(5-Fluoro-2-methylphenoxymethyl)-7-[2-methoxy-4-(N-methyl-N-methylaminoethyl)aminopropylsulfonyloxyphenyl]-1,3,3-trimethyl-3,4-dihydro-1H-quinoxalin-2-one.

The present compound can be synthesized according to the following procedures. The individual concrete preparation procedures are explained in details in the section of "Production Examples" in Examples. These examples are intended to make the present invention more clearly understandable, and do not limit the scope of the present invention. In the following synthetic routes, the hal represents a halogen atom, the Fmoc represents a 9-fluorenylmethoxycarbonyl group and the PG represents a protective group (Proective Group).

The present compound (I)-(a) (the compound in which X is an oxygen atom, Z is an oxygen atom, a sulfur atom, OCO, OSO$_2$ in the general formula (1)) can be synthesized according to the synthetic route 1. That is, the compound (I)-(a) can be given by the reaction of the compound (II) with a corresponding halide (III) in an organic solvent such as N,N-dimethylformamide (hereinafter referred to as DMF), tetrahydrofuran (hereinafter referred to as THF), 1,4-dioxane, methylene dichloride in the presence of a base such as triethylamine, potassium carbonate at 0° C. to 50° C. for 1 hour to 24 hours.

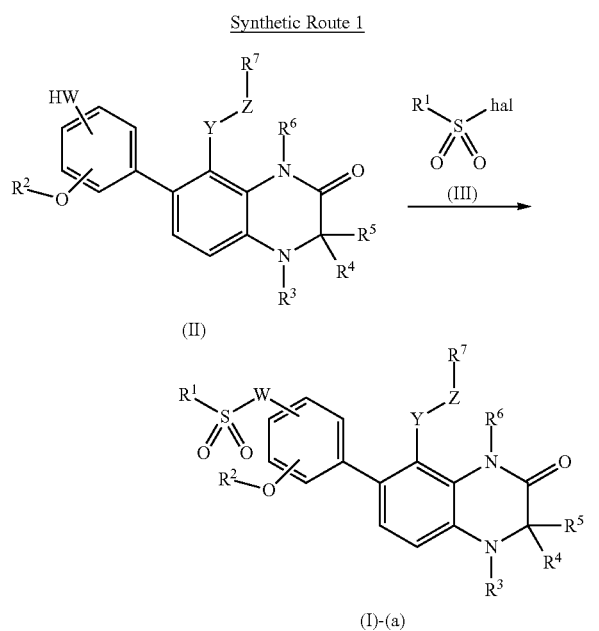

The present compound (I)-(b) (the compound in which X is an oxygen atom, Z is NR$^9$, R$^9$ is a hydrogen atom in the general formula (1)) can be synthesized according to the synthetic route 2. That is, the compound (V) can be given by the reaction of the compound (IV) with a corresponding halide (III) in an organic solvent such as DMF, THF, 1,4-dioxane, methylene dichloride in the presence of a base such as triethylamine, potassium carbonate at 0° C. to 50° C. for 1 hour to 24 hours. The present compound (I)-(b) can be given by the treatment of the obtained compound (V) in an organic solvent such as DMF, methylene dichloride in the presence of a base such as piperidine at 0° C. to 50° C. for 5 minutes to 24 hours.

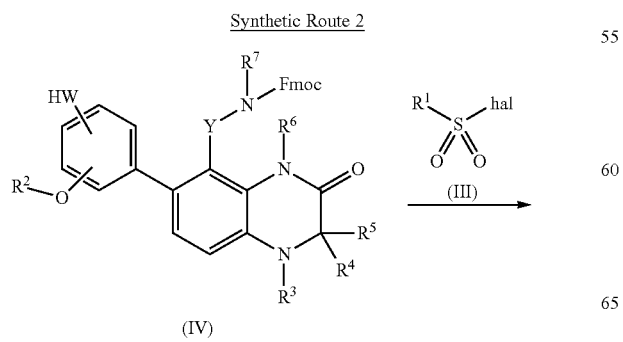

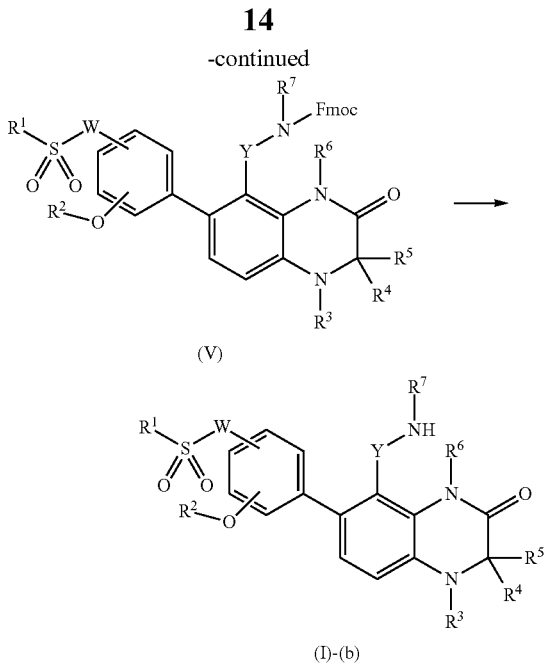

The compound (II)-(a) (the compound in which W is an oxygen atom, Y is a methylene group, Z is an oxygen atom in the above compound (II)) can be synthesized according to the synthetic route 3. That is, the compound (VIII) can be given by the reaction of the compound (VI) with a corresponding boronic acid (VII) in a solvent such as DMF, 1,4-dioxane, ethanol, toluene, water in the presence of a base such as cesium carbonate, sodium carbonate, sodium hydrogen carbonate, potassium phosphate and a catalyst such as bis(triphenylphosphine)palladium (II) dichloride, tetrakis(triphenylphosphine)palladium (0) at 50° C. to 120° C. for 10 minutes to 48 hours. The compound (II)-(a) can be given by the deprotection of the protective group in the obtained compound (VIII) in an appropriate condition.

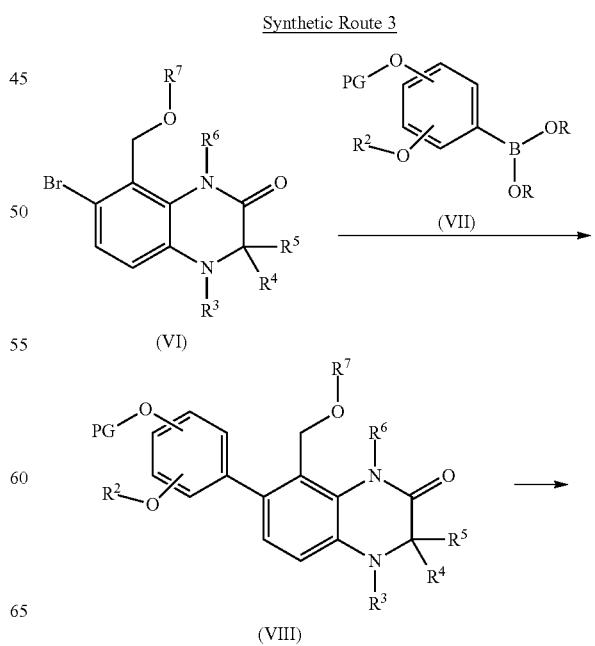

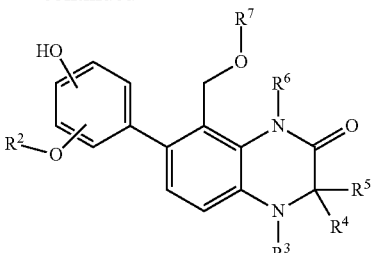

(II)-(a)

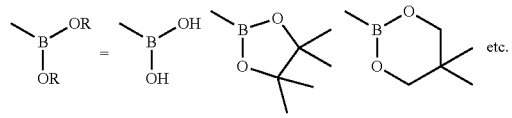

The compound (II)-(b) (the compound in which W is NH, Y is a methylene group, Z is an oxygen atom in the above compound (II)) can be synthesized according to the synthetic route 4. That is, the compound (X) can be given by the reaction of the compound (VI) with a corresponding boronic acid (IX) in solvent such as DMF, 1,4-dioxane, ethanol, toluene, water in the presence of a base such as cesium carbonate, sodium carbonate, sodium hydrogen carbonate, potassium phosphate and a catalyst such as bis(triphenylphosphine)palladium (II) dichloride, tetrakis(triphenylphosphine) palladium (0) at 50° C. to 120° C. for 10 minutes to 48 hours. The compound (II)-(b) can be given by the treatment of the obtained compound (X) in a solvent such as DMF, methanol in the presence of a reducing agent such as tin(II) chloride, iron at room temperature to 100° C. for 1 hour to 24 hours.

Synthetic Route 4

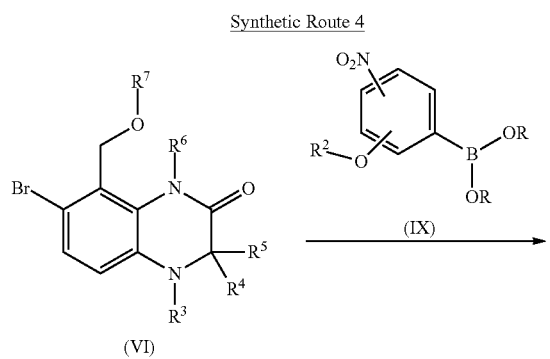

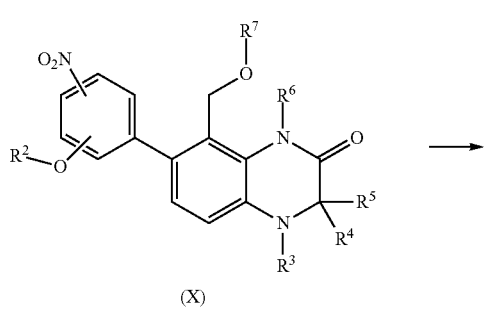

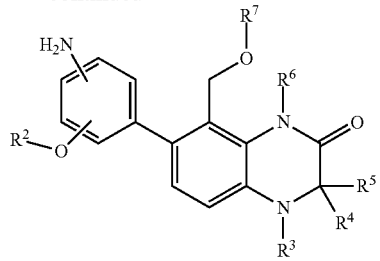

(II)-(b)

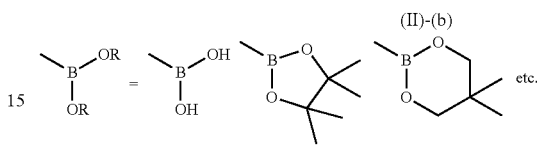

The compound (VI) can be synthesized according to the synthetic route 5. That is, the compound (VI) can be given by the reaction of the compound (XI) with a corresponding phenol (XII) in an organic solvent such as benzene, THF in the presence of a phosphine such as triphenylphosphine, tributylphosphine and a reagent such as diethylazodicarboxylate, diisopropylazodicarboxylate, 1,1'-(azodicarbonyl)dipiperidine at room temperature for hour to 2 days.

Synthetic Route 5

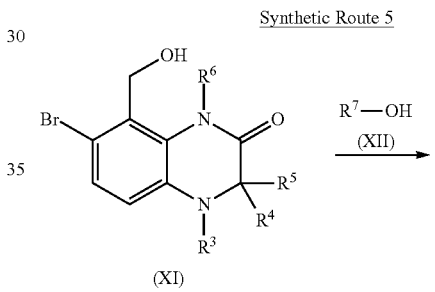

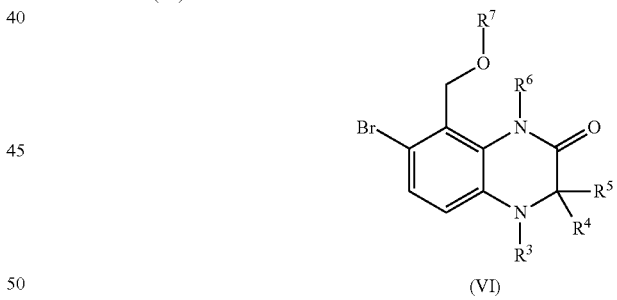

The compound (II)-(c) compound in which W is an oxygen atom, Y is a methylene group, Z is OCO in the above compound (II)) can be synthesized according to the synthetic route 6. That is, the compound (XIV) can be given by the reaction of the compound (XIII) with a corresponding boronic acid (VII) in a solvent such as DMF, 1,4-dioxane, ethanol, toluene, water in the presence of a base such as cesium carbonate, sodium carbonate, sodium hydrogen carbonate, potassium phosphate and a catalyst such as bis(triphenylphosphine)palladium (II) dichloride, tetrakis(triphenylphosphine)palladium (0) at 50° C. to 120° C. for 10 minutes to 48 hours. The compound (XV) can be given by the treatment of the obtained compound (XIV) in an organic solvent such as diethyl ether, THF in the presence of a reducing agent such lithium aluminium hydride at 0° C. to 50° C.

for 1 hour to 24 hours. The compound (XVII) can be given by the reaction of the obtained compound (XV) with methanesulfonyl chloride in an organic solvent such as methylene dichloride, THF in the presence of a base such as triethylamine, DIEA at 0° C. to room temperature for 30 minutes 24 hours followed by the reaction with a corresponding carboxylic acid (XVI) in an organic solvent such as DMF, THF, ethanol in the presence of a base such as potassium carbonate, sodium hydride at 0° C. to 100° C. for 1 hour to 48 hours. The compound (XIX) can be given by the reaction of the obtained compound (XVII) with a corresponding halide (XVIII) in an organic solvent such as DMF, THF, 1,4-dioxane, methylene dichloride in the presence of a base such as cesium carbonate, potassium carbonate at 0° C. to 50° C. for 1 hour to 24 hours. The compound (II)-(c) can be given by the deprotection of the protective group in the obtained compound (XIX) in an appropriate condition.

Synthetic Route 6

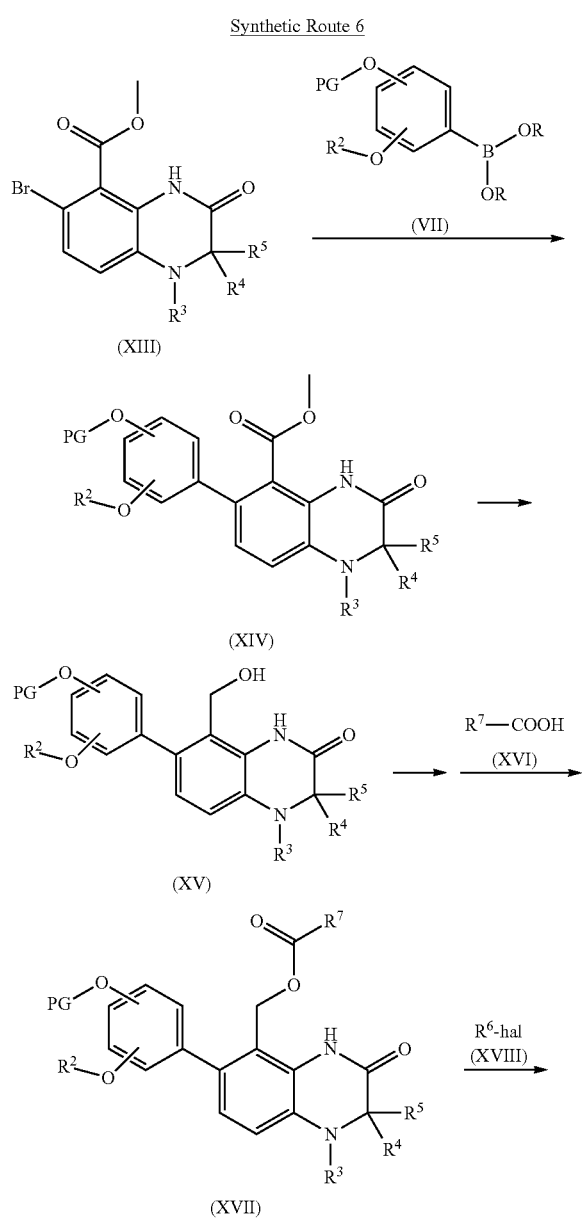

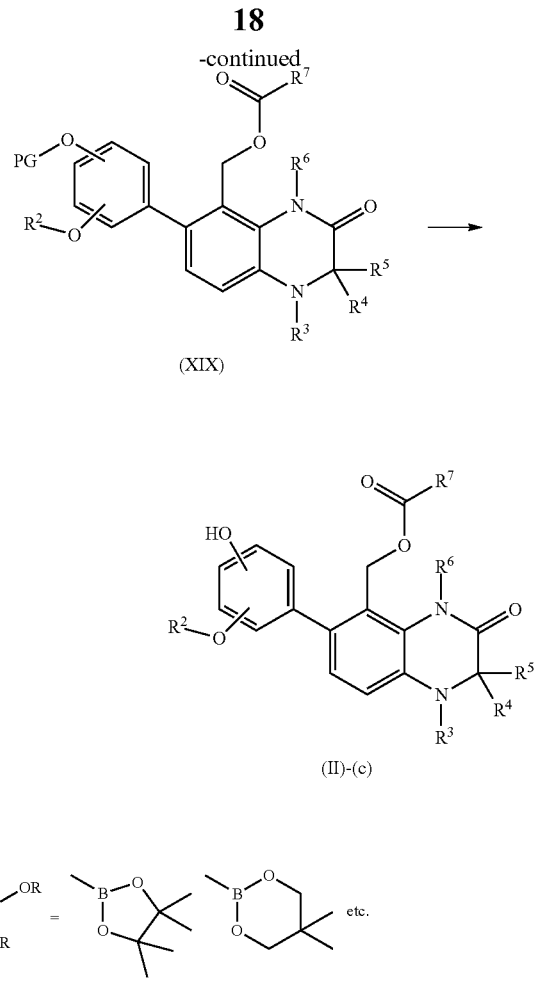

The compound (IV)-(a) (the compound in which W is an oxygen atom, Y is a methylene group in the compound (IV)) can be synthesized according to the synthetic route 7. That is, the compound (XX) can be given by the reaction of the compound (XI) with methanesulfonyl chloride in an organic solvent such as methylene dichloride, THF in the presence of a base such as triethylamine, DIEA at 0° C. to room temperature for 30 minutes to 24 hours. The compound (XXII) can be given by the reaction of the compound (XX) with a corresponding amine (XXI) in an organic solvent such as DMF, THF, ethanol in the presence of a base such as potassium carbonate, sodium hydride at 0° C. to 100° C. for 1 hour to 48 hours. The compound (XXIII) can be given by the reaction of the obtained compound (XXII) with a corresponding boronic acid (VII) in a solvent such as DMF, 1,4-dioxane, ethanol, toluene, water in the presence of a base such as cesium carbonate, sodium carbonate, sodium hydrogen carbonate, potassium phosphate and a catalyst such as bis(triphenylphosphine)palladium (II) dichloride, tetrakis(triphenylphosphine)palladium (0) at 50° C. to 120° C. for 1 hour to 48 hours. The compound (XXIV) can be given by the reaction of the obtained compound (XXIII) with 9-fluorenylmethoxycarbonyl chloride in a solvent such as 1,4-dioxane, water in the presence of a base such as sodium hydrogen carbonate at 0° C. to 50° C. for 1 hour to 24 hours. The compound (IV)-(a) can be given by the deprotection of the protective group in the obtained compound (XXIII) in an appropriate condition.

Synthetic Route 7

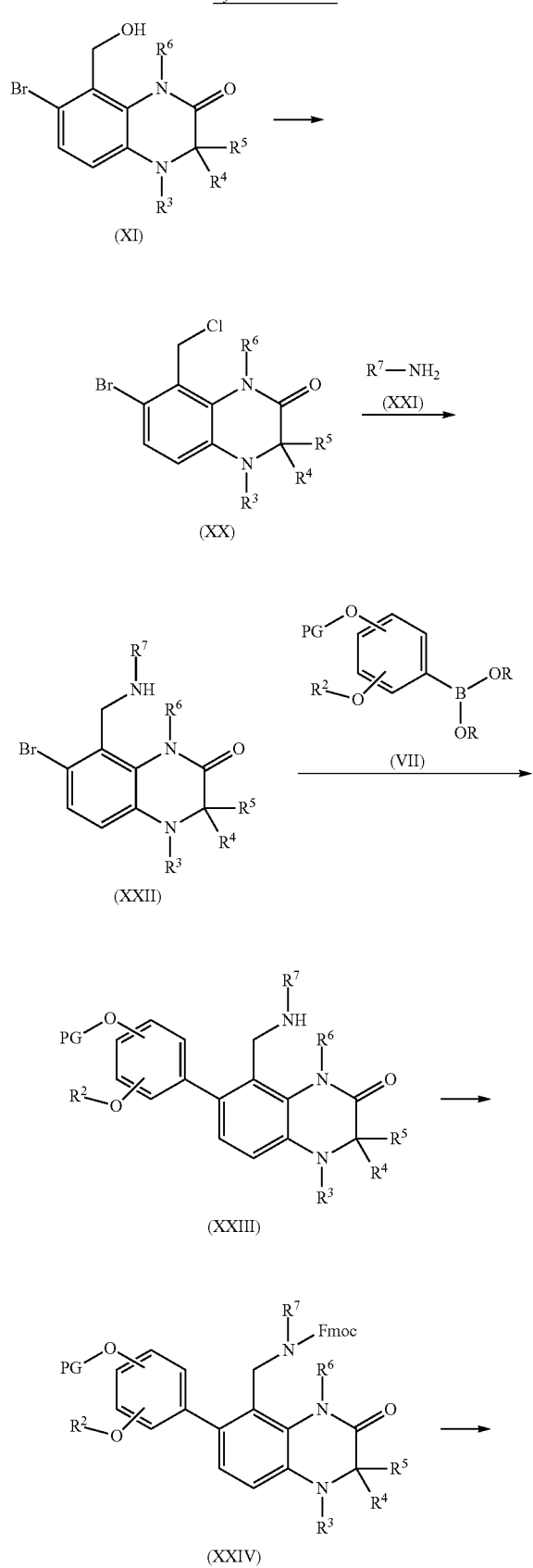

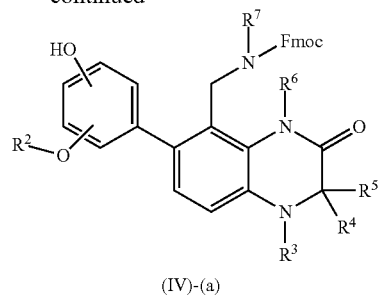

The above compound (XI)-(a) (the compound in which $R^3$ is a hydrogen atom in the above compound (XI)) and the above compound (XIII)-(a) (the compound in which $R^3$ is a hydrogen atom in the above compound (XIII)) can be synthesized according to the synthetic route 8. That is, the compound (XXVI) can be given by the treatment of the compound (XXV) in an organic solvent such as methanol, ethanol, DMF in the presence of a reducing agent such as tin(II) chloride, iron at 50° C. to 120° C. for 1 hour to 12 hours. The compound (XXVII) can be given by the treatment of the obtained compound (XXVI) with an acetylation agent such as acetyl chloride, acetic anhydride in an organic solvent such as methylene dichloride, THF in the presence of a base such as triethylamine, DIEA at 0° C. to 50° C. for 1 hour to 12 hours. The compound (XXVIII) can be given by the reaction of the obtained compound (XXVII) with nitric acid in a solvent such as water in the presence of an acid such as sulfuric acid at −20° C. to room temperature for 30 minutes to 12 hours. The compound (XXIX) can be given by the treatment of the obtained compound (XXVIII) in an organic solvent such as methanol in the presence of an acid such as boron trifluoride diethylether complex at 50° C. to the temperature under reflux for 1 hour to 12 hours. The compound (XXXI) can be given by the reaction of the obtained compound (XXIX) with a corresponding halide (XXX) in the presence of a base such as cesium carbonate, potassium carbonate at 50° C. to 120° C. for 1 hour to 120 hours. The compound (XIII)-(a) can be given by the treatment of the obtained compound (XXXI) in an organic solvent such as methanol, ethanol, DMF in the presence of a reducing agent such as tin(II) chloride, iron at 50° C. to 120° C. for 1 hour to 12 hours. The compound (XXXII) can be given by the treatment of the obtained compound (XIII)-(a) in an organic solvent such as diethyl ether, THF and in the presence of a reducing agent such as lithium aluminium hydride at 0° C. to 50° C. for 1 hour to 24 hours. The compound (XI)-(a) can be given by the reaction of the obtained compound (XXXII) with a corresponding halide (XVIII) in an organic solvent such as DMF, THF, 1,4-dioxane, methylene dichloride in the presence of base such as cesium carbonate, potassium carbonate at 0° C. to 50° C. for 1 hour to 24 hours.

Synthetic Route 8

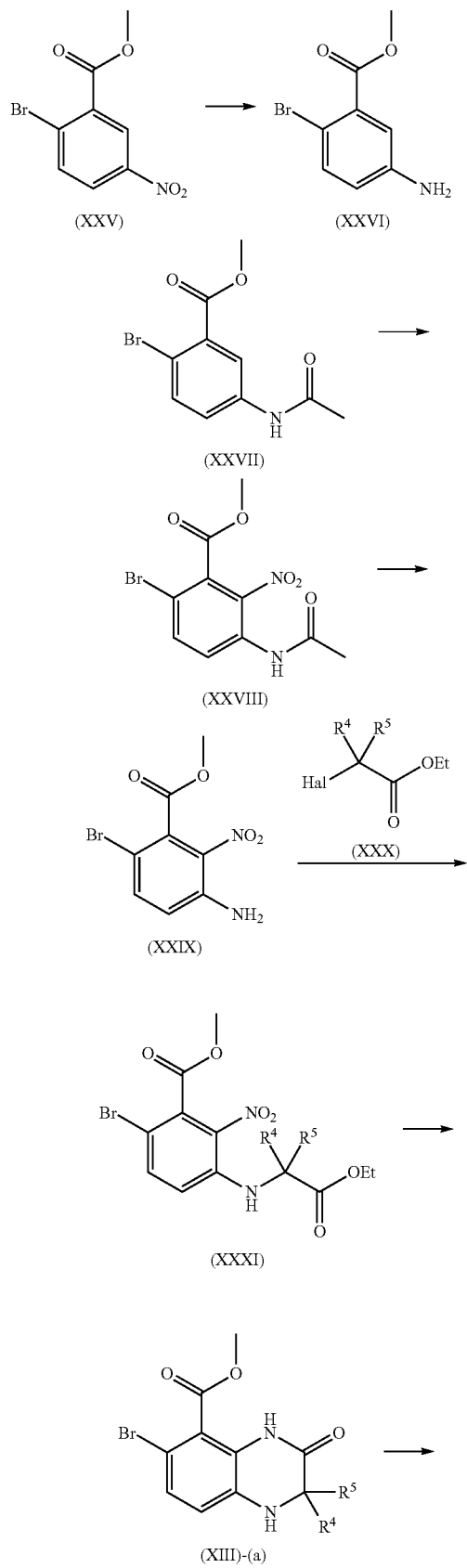

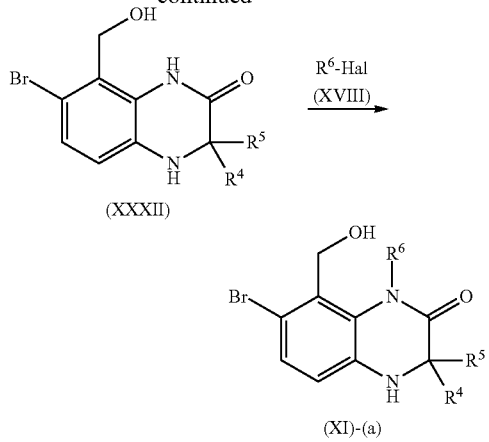

As shown in the above-mentioned, the glucocorticoid receptor is associated with the occurrence of various diseases as described above, therefore, the present compound having an excellent binding activity to the glucocorticoid receptor is useful as a glucocorticoid receptor modulator. The details of the pharmacological effect will be explained in detail in the section of "Pharmacological Test" in Examples described below.

The present compound can be administered either orally or parenterally. Examples of the dosage form include a tablet, a capsule, a granule, a powder, an injection, an eye drop, a suppository, percutaneous absorption preparation, an ointment, an aerosol (including an inhalant) and the like and such a preparation can be prepared using a commonly used technique.

For example, an oral preparation such as a tablet, a capsule, a granule or a powder can be prepared by optionally adding a necessary amount of an excipient such as lactose, mannitol, starch, crystalline cellulose, light silicic anhydride, calcium carbonate or calcium hydrogen phosphate; a lubricant such as stearic acid, magnesium stearate or talc; a binder such as starch, hydroxypropyl cellulose, hydroxypropylmethyl cellulose or polyvinylpyrrolidone; a disintegrant such as carboxymethyl cellulose, low-substituted hydroxypropylmethyl cellulose or calcium citrate; a coating agent such as hydroxypropylmethyl cellulose, macrogol or a silicone resin; a stabilizer such as ethyl p-hydroxybenzoate or benzyl alcohol; a corrigent such as a sweetener, a sour agent or a flavor, or the like.

A parenteral preparation such as an injection or an eye drop can be prepared by optionally adding a necessary amount of a tonicity agent such as sodium chloride, concentrated glycerin, propylene glycol, polyethylene glycol, potassium chloride, sorbitol or mannitol; a buffer such as sodium phosphate, sodium hydrogen phosphate, sodium acetate, citric acid, glacial acetic acid or trometamol; a surfactant such as polysorbate 80, polyoxy 40 stearate or polyoxyethylene hydrogenated castor oil 60; a stabilizer such as sodium citrate or sodium edetate; a preservative such as benzalkonium chloride, paraben, benzothonium chloride, p-hydroxybenzoate ester, sodium benzoate, chlorobutanol or sorbic acid; a pH adjusting agent such as hydrochloric acid, citric acid, phosphoric acid, glacial acetic acid, sodium hydroxide, sodium carbonate or sodium hydrogen carbonate; a soothing agent such as benzyl alcohol, or the like.

The dose of the present compound can be appropriately selected depending on symptoms, age, dosage form or the like. For example, in the case of an oral preparation, it can be administered in an amount of generally 0.01 to 1000 mg, preferably 1 to 100 mg per day in a single dose or several divided doses. Further, in the case of an eye drop, a preparation containing the present compound at a concentration of generally 0.0001% to 10% (w/v), preferably 0.01% to 5% (w/v) can be administered in a single dose or several divided doses.

Hereinafter, Production Examples of the present compound, Preparation Examples and results of Pharmacological Test will be described. However, these examples are described for the purpose of understanding the sent invention better and are not meant to limit the scope of the present invention.

Production Example

Reference Example 1

7-Bromo-8-hydroxymethyl-1,3,3-trimethyl-3,4-dihydro-1H-quinoxalin-2-one

Reference Compound No. 1

Methyl 5-amino-2-bromobenzoate

Reference Compound No. 1-(1)

Methyl 2-bromo-5-nitrobenzoate (25.3 g, 97.3 mmol) was dissolved in anhydrous methanol (500 mL), tin (II) chloride (93.3 g, 487 mmol) was added thereto, and then the reaction mixture was refluxed for 2 hours. The reaction mixture was cooled down, ethyl acetate (500 mL) and water (100 mL) were added thereto, the mixture was neutralized with 4N aqueous sodium hydroxide solution, and then filtered on celite. The filtrate was concentrated under reduced pressure, ethyl acetate (200 mL) was added thereto, and then the mixture was washed with saturated aqueous sodium hydrogen carbonate solution (200 mL, twice), water (200 mL), and saturated brine (200 mL) successively. The organic layer was dried over anhydrous magnesium sulfate and the solvent was removed under reduced pressure to give the titled reference compound (21.0 g) as a pale yellow oil. (Yield 94%)

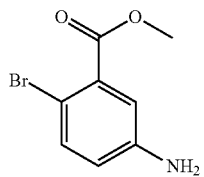

$^1$H-NMR (400 MHz, DMSO-$d_6$) δ 3.80 (s, 3H), 5.55 (s, 2H), 6.63 (dd, J = 8.8, 2.8 Hz, 1H), 6.94 (d, J = 2.8 Hz, 1H), 7.29 (d, J = 8.8 Hz, 1H)

Methyl 5-acetylamino-2-bromobenzoate

Reference Compound No. 1-(2)

Methy 5-amino-2-bromobenzoate (Reference Compound No. 1-(1), 21.0 g, 91.2 mmol) and triethylamine (19.0 mL, 137 mmol) were dissolved in anhydrous dichloromethane (450 mL) acetyl chloride (13.0 mL, 182 mmol) was added dropwise over 30 minutes under ice cooling, and then the mixture was stirred at 0° C. for 2 hours. The reaction mixture was washed with water (200 mL, twice), saturated aqueous sodium hydrogen carbonate solution (200 mL, twice), and saturated brine (200 mL) successively, dried over anhydrous magnesium sulfate, and then the solvent was removed under reduced pressure. The obtained residue was filtered with hexane-ethyl acetate (20:1) to give the titled reference compound (24.2 g) as a pale yellow solid. (Yield 98%)

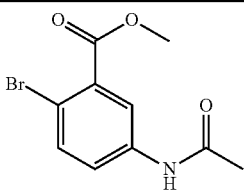

$^1$H-NMR (400 MHz, DMSO-$d_6$) δ 2.06 (s, 3H), 3.86 (s, 3H), 7.63-7.66 (m, 2H), 8.07 (s, 1H), 10.25 (s, 1H)

Methyl 3-acetylamino-6-bromo-2-nitrobenzoate

Reference Compound No. 1-(3)

To conc. sulfuric acid (150 mL), methyl 5-acetylamino-2-bromobenzoate (Reference Compound No. 1-(2), 18.5 g, 68.1 mmol) was added portionwise at 0° C., and conc. nitric acid (150 mL) was added dropwise thereto over 1 hour. The reaction mixture was stirred for 30 minutes, poured into iced water (1 L), and then the whole was extracted with ethyl acetate (500 mL, twice). The organic layer was washed with water (1 L, twice), saturated aqueous sodium hydrogen carbonate solution (1 L), and saturated brine (1 L) successively, dried over anhydrous magnesium sulfate, and then the solvent was removed under reduced pressure. The obtained residue was purified by silica gel column chromatography (hexane-ethyl acetate) to give the titled reference compound (13.4 g) as a yellow solid. (Yield 62%)

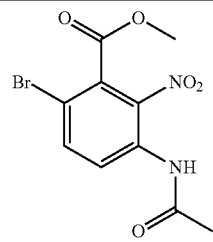

$^1$H-NMR (400 MHz, DMSO-$d_6$) δ 2.05 (s, 3H), 3.87 (s, 3H), 7.55 (d, J = 8.8 Hz, 1H), 8.02 (d, J = 8.8 Hz, 1H), 10.48 (s, 1H)

Methyl 3-amino-6-bromo-2-nitrobenzoate

Reference Compound No. 1-(4)

Methyl 3-acetylamino-6-bromo-2-nitrobenzoate (Reference. Compound No. 1-(3), 13.4 g, 42.2 mmol) was dissolved in methanol (240 mL), boron trifluoride diethyl etherate complex (24.0 mL, 190 mmol) was added thereto, and then the mixture was refluxed for 2.5 hours. After the reaction mixture was neutralized with sodium hydrogen carbonate (48 g), the mixture was concentrated under reduced pressure. After ethyl acetate (500 mL) and water (700 mL) were added thereto and the mixture was partitioned, the ethyl acetate layer was washed with water (700 mL) and saturated brine (700 mL) successively, dried over anhydrous magnesium sulfate, and then the solvent was removed under reduced pressure to give the titled reference compound (11.6 g) as an orange solid. (Yield 100%)

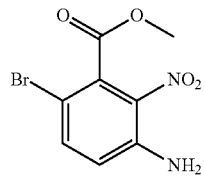

¹H-NMR (500 MHz, CDCl₃) δ 3.98 (s, 3H), 6.15 (br s, 2H), 6.78 (d, J = 9.2 Hz, 1H), 7.48 (d, J = 9.2 Hz, 1H)

Methyl 6-bromo-3-[(2-ethoxycarbonyl)propan-2-yl]amino-2-nitrobenzoate

Reference Compound No. 1-(5)

A mixture of methyl 3-amino-6-bromo-2-nitrobenzoate (Reference Compound No. 1-(4), 11.6 g, 42.0 mmol), ethyl 2-bromoisobutyrate (60.4 mL, 412 mmol), potassium iodide (7.76 g, 46.2 mmol) and cesium carbonate (56.1 g, 172 mmol) was stirred at 85° C. for 4 days. After cooling down, ethyl acetate (500 mL) and water (500 mL) were added thereto, the mixture was partitioned, and then the water layer was extracted with ethyl acetate (300 mL). The organic layer was combined, washed with water (1 L, twice) and saturated brine (1 L) successively, dried over anhydrous magnesium sulfate, and then the solvent was removed under reduced pressure. The obtained residue was purified by silica gel column chromatography (hexane-ethyl acetate) to give the titled reference compound (5.08 g) as an orange oil. (Yield 31%)

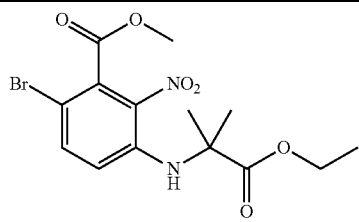

¹H-NMR (400 MHz, CDCl₃) δ 1.22 (t, J = 7.1 Hz, 3H), 1.65 (s, 6H), 3.98 (s, 3H), 4.20 (d, J = 7.1 Hz, 2H), 6.56 (d, J = 9.4 Hz, 1H), 7.49 (d, J = 9.4 Hz, 1H), 8.31 (s, 1H)

7-Bromo-8-methoxycarbonyl-3,3-dimethyl-3,4-dihydro-1H-quinoxalin-2-one

Reference Compound No. 1-(6)

Methyl 6-bromo-3-[(2-ethoxycarbonyl)propan-2-yl]amino-2-nitrobenz oate (Reference Compound No. 1-(5), 105 mg, 0.26 mmol) was dissolved in anhydrous ethanol (4.5 mL), tin (II) chloride (247 mg, 1.30 mmol) was added thereto, and then the reaction mixture was refluxed for 5 hours. After the reaction mixture was cooled down, ethyl acetate (25 mL) was added thereto, the mixture was neutralized with aqueous sodium hydrogen carbonate solution, and then filtered on celite. After the filtrate was partitioned, the water layer was extracted with ethyl acetate (10 mL, twice), the combined organic layer was washed with water (50 mL, twice) and saturated brine (50 mL) successively, dried aver anhydrous magnesium sulfate, and then the solvent, was removed under reduced pressure. The obtained residue was purified by silica gel column chromatography (hexane-ethyl acetate) to give the titled reference compound (56.3 mg) as a pale yellow solid. (Yield 70%)

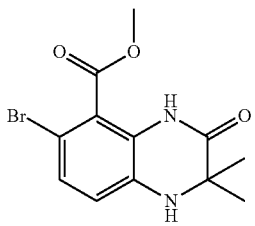 [SMILES: COC(=O)c1c(Br)ccc2c1NC(=O)C(C)(C)N2]

¹H-NMR (400 MHz, CDCl₃) δ 1.39 (s, 6H), 3.86 (s, 1H), 3.98 (s, 3H), 6.62 (d, J = 8.5 Hz, 1H), 7.13 (d, J = 8.5 Hz, 1H), 8.89 (s, 1H)

7-Bromo-8-hydroxymethyl-3,3-dimethyl-3,4-dihydro-1H-quinoxalin-2-one

Reference Compound No. 1-(7)

Lithium aluminium hydride (38.5 mg, 1.01 mmol) was suspended in anhydrous tetrahydrofuran (0.5 mL) under nitrogen atmosphere. An anhydrous tetrahydrofuran solution (1.5 mL) of 7-bromo-8-methoxycarbonyl-3,3-dimethyl-3,4-dihydro-1H-quinoxalin-2-one (Reference Compound No. 1, 101 mg, 0.323 mmol) was added dropwise thereto at 0° C., and the mixture was stirred for 1 hour at the same temperature. Ethyl acetate (10 mL), water (10 mL), and 1N aqueous hydrochloride solution (2 mL) were added thereto successively and the mixture was partitioned. The organic layer was washed with saturated brine (10 mL), dried over anhydrous magnesium sulfate, and then the solvent, was removed under reduced pressure. The obtained residue was purified by silica gel column chromatography (hexane-ethyl acetate) to give trio titled reference compound (67.4 mg) as an orange amorphous product. (Yield 74%)

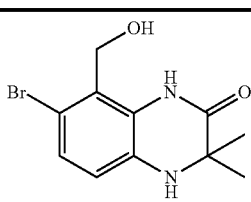

¹H-NMR (400 MHz, CDCl₃) δ 1.39 (s, 6H), 3.18 (br s, 1H), 3.75 (s, 1H), 4.99 (d, J = 9.5 Hz, 2H), 6.51 (d, J = 8.3 Hz, 1H), 7.07 (d, J = 8.3 Hz, 1H), 9.40 (s, 1H)

7-Bromo-8-hydroxymethyl-1,3,3-trimethyl-3,4-dihydro-1H-quinoxalin-2-one

Reference Compound No. 1

A mixture of 7-bromo-8-hydroxymethyl-3,3-dimethyl-3,4-dihydro-1H-quinoxalin-2-one (Reference Compound No. 1-(7), 62.7 mg, 0.220 mmol), methyl iodide (68.6 µL, 1.10 mmol), and cesium carbonate (180 mg, 0.552 mmol) was suspended in anhydrous N,N-dimethylformamide (1 mL) and stirred at room temperature for 2.5 hours. Ethyl acetate (10 mL) and water (10 mL) were added to the reaction mixture and partitioned. The organic layer was washed with saturated brine (10 mL), dried over anhydrous magnesium sulfate, and then the solvent was removed under reduced pressure. The obtained residue was purified by silica eel column chromatography (hexane-ethyl acetate) to give the titled reference compound (45.5 mg) as an orange amorphous product. (Yield 69%)

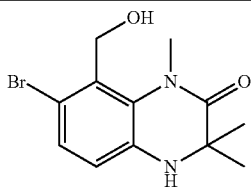

¹H-NMR (400 MHz, CDCl₃) δ 1.31 (s, 6H), 3.56 (s, 3 H), 3.77 (br s, 1H), 4.73 (d, J = 7.1 Hz, 2H), 6.57 (d, J = 8.4 Hz, 1H), 7.17 (d, J = 8.4 Hz, 1H)

Reference Example 2

7-Bromo-8-chloromethyl-1,3,3-trimethyl-3,4-dihydro-1H-quinoxalin-2-one

Reference Compound No. 2

7-Bromo-8-hydroxymethyl-1,3,3-trimethyl-3,4-dihydro-1H-quinoxalin-2-one (Reference Compound No. 1, 37.5 mg, 0.125 mmol) was dissolved in anhydrous dichloromethane (1 mL), and triethylamine (20.9 µL, 0.150 mmol) and methanesulfonyl chloride (10.7 µL, 0.138 mmol) were added thereto successively. The reaction mixture was stirred at room temperature overnight. Ethyl acetate (10 mL) and water (10 mL) were added to the reaction mixture and partitioned. The organic layer was washed with saturated brine (10 mL), dried over anhydrous magnesium sulfate, and then the solvent was removed under reduced pressure. The obtained residue was purified by silica gel column chromatography (hexane-ethyl acetate) to give the titled reference compound (28.7 mg) as an orange amorphous product. (Yield 72%)

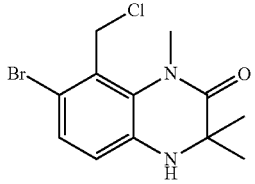

¹H-NMR (400 MHz, CDCl₃) δ 1.30 (s, 6H), 3.55 (s, 3 H), 3.76 (br s, 1H), 4.76 (s, 2H), 6.61 (d, J = 8.4 Hz, 1 H), 7.23 (d, J = 8.4 Hz, 1H)

Reference Example 3

7-Bromo-8-(5-fluoro-2-methylphenoxymethyl)-1,3,3-trimethyl-3,4-dihydro-1H-quinoxalin-2-one Reference Compound No. 3-1

A mixture of 7-bromo-8-hydroxymethyl-1,3,3-trimethyl-3,4-dihydro-1H-quinoxalin-2-one (Reference Compound No. 1, 805 mg, 2.69 mmol), 5-fluoro-2-methylphenol (382 µL, 3.50 mmol), and tri-n-butylphosphine (874 µL, 3.50 mmol) was dissolved in anhydrous tetrahydrofuran (25 mL), 1,1'-(azodicarbonyl)dipiperidine (883 mg, 3.50 mmol) was added thereto, and then the mixture was stirred at room temperature for 1 hour. 5-Flue 2-methylphenol (382 µL, 3.50 mmol), tri-n-butylphosphine (874 µL, 3.50 mmol), and 1,1'-(azodicarbonyl)dipiperidine (890 mg, 3.53 mmol) were added thereto and it was furthermore stirred for 20 minutes. After hexane (15 mL) was added to the reaction mixture and the precipitated solids were filtered out the filtrate was concentrated under reduced pressure and the obtained residue was purified by silica gel column chromatography (hexane-ethyl acetate) to give the titled reference compound (900 mg) as a colorless solid. (Yield 82%)

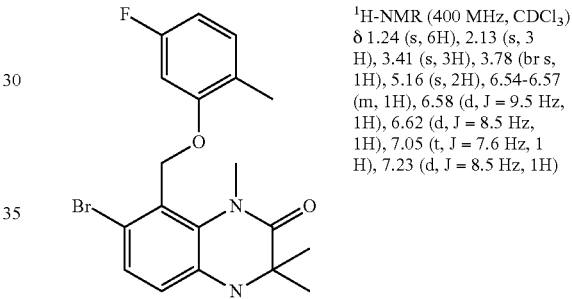

¹H-NMR (400 MHz, CDCl₃) δ 1.24 (s, 6H), 2.13 (s, 3 H), 3.41 (s, 3H), 3.78 (br s, 1H), 5.16 (s, 2H), 6.54-6.57 (m, 1H), 6.58 (d, J = 9.5 Hz, 1H), 6.62 (d, J = 8.5 Hz, 1H), 7.05 (t, J = 7.6 Hz, 1 H), 7.23 (d, J = 8.5 Hz, 1H)

Using any compounds among Reference Compounds No. 1, 12-1, and available compounds, the following Reference Compounds (No. 3-2~3-4) were obtained by a method similar to that of Reference Compound No. 3-1.

| 7-Bromo-8-(2-methoxy-5-nitrophenoxymethyl)-1,3,3-trimethyl-3,4-dihydro-1H-quinoxalin-2-one (Reference Compound No. 3-2) 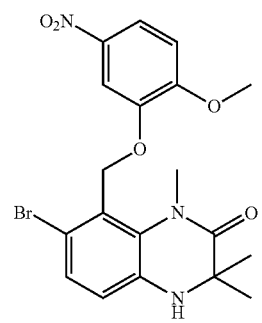 | ¹H-NMR (500 MHz, CDCl₃) δ 1.25 (s, 6H), 3.46 (s, 3 H), 3.78 (s, 1H), 3.94 (s, 3 H), 5.26 (s, 2H), 6.63 (d, J = 8.4 Hz, 1H), 6.93 (d, J = 9.1 Hz, 1H), 7.24 (d, J = 8.4 Hz, 1H), 7.85 (d, J = 2.5 Hz, 1H), 7.95 (dd, J = 9.1, 2.5 Hz, 1H) |
|---|---|

-continued

| | |
|---|---|
| 7-Bromo-8-(2-methyl-5-nitro-phenoxymethyl)-1,3,3-trimethyl-3,4-dihydro-1H-quinoxalin-2-one (Reference Compound No. 3-3)<br>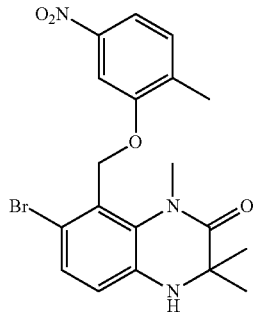 [SMILES: Cc1ccc([N+](=O)[O-])cc1OCc1c(Br)ccc2c1N(C)C(=O)C(C)(C)N2] | $^1$H-NMR (400 MHz, CDCl$_3$) δ 1.25 (s, 6H), 2.28 (s, 3H), 3.41 (s, 3H), 3.81 (s, 1H), 5.29 (s, 2H), 6.64 (d, J = 8.3 Hz, 1H), 7.26 (d, J = 8.3 Hz, 1H), 7.28 (d, J = 8.3 Hz, 1H), 7.72 (d, J = 2.2 Hz, 1H), 7.79 (dd, J = 8.3, 2.2 Hz, 1H) |
| 7-(2-Methoxy-4-methoxymethoxy-phenyl)-8-(4-methylbenzoyl-oxymethyl)-1,3,3-trimethyl-3,4-dihydro-1H-quinoxalin-2-one (Reference Compound No. 3-4)<br>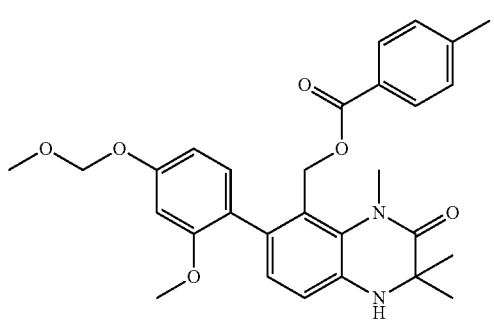 | $^1$H-NMR (400 MHz, CDCl$_3$) δ 1.19 (s, 3H), 1.42 (s, 3H), 2.36 (s, 3H), 3.45 (s, 3H), 3.50 (s, 3H), 3.74 (s, 3H), 3.76 (s, 1H), 5.18 (d, J = 13.3 Hz, 1H), 5.18 (s, 2H), 5.33 (d, J = 13.3 Hz, 1H), 6.62 (d, J = 2.4 Hz, 1H), 6.65 (dd, J = 8.2, 2.4 Hz, 1H), 6.75 (d, J = 7.8 Hz, 1H), 6.87 (d, J = 7.8 Hz, 1H), 7.16 (d, J = 8.0 Hz, 2H), 7.16 (d, J = 8.2 Hz, 1H), 7.73 (d, J = 8.0 Hz, 2H) |

Reference Example 4

7-Bromo-8-(2-methoxyphenylaminomethyl)-1,3,3-trimethyl-3,4-dihydro-1H-quinoxalin-2-one Reference Compound No. 4-1

7-Bromo-8-chloromethyl-1,3,3-trimethyl-3,4-dihydro-1H-quinoxalin-2-one (Reference Compound No. 2, 1.82 g, 5.73 mmol), 2-methoxyaniline (728 μL, 6.46 mmol), and potassium carbonate (1.19 g, 8.61 mmol) were suspended in anhydrous N,N-dimethylformamide (30 mL) and the mixture was stirred at 80° C. overnight. After cooling down, ethyl acetate (100 mL) and diethylether (100 mL) were added. The organic layer was washed with water (200 mL, 100 mL) and saturated brine (100 mL), dried over anhydrous magnesium sulfate, and then the solvent was removed under reduced pressure. The obtained residue was purified by silica gel column chromatography (hexane-ethyl acetate) to give the titled reference compound (1.45 g) as a pale yellow amorphous product. (Yield 63%)

Using any compounds among Reference Compounds No. 2 and available compounds, the following Reference Compound (No. 4-2) was obtained by a method similar to that of Reference Compound No. 4-1.

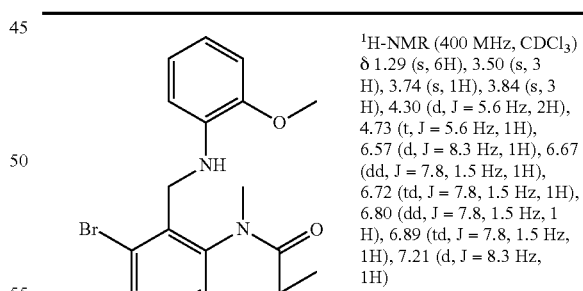

$^1$H-NMR (400 MHz, CDCl$_3$) δ 1.29 (s, 6H), 3.50 (s, 3H), 3.74 (s, 1H), 3.84 (s, 3H), 4.30 (d, J = 5.6 Hz, 2H), 4.73 (t, J = 5.6 Hz, 1H), 6.57 (d, J = 8.3 Hz, 1H), 6.67 (dd, J = 7.8, 1.5 Hz, 1H), 6.72 (td, J = 7.8, 1.5 Hz, 1H), 6.80 (dd, J = 7.8, 1.5 Hz, 1H), 6.89 (td, J = 7.8, 1.5 Hz, 1H), 7.21 (d, J = 8.3 Hz, 1H)

| 7-Bromo-8-(5-fluoro-2-methyl-phenylaminomethyl)-1,3,3-tri-methyl-3,4-dihydro-1H-quinoxalin-2-one (Reference Compound No. 4-2) | ¹H-NMR (500 MHz, CDCl₃) δ 1.30 (s, 6H), 2.11 (s, 3 H), 3.47 (s, 3H), 3.78 (s, 1 H), 4.12 (br s, 1H), 4.30 (d, J = 5.5 Hz, 2H), 6.35-6.40 (m, 2H), 6.60 (d, J = 8.6 Hz, 1H), 6.98 (t, J = 7.2 Hz, 1 H), 7.22 (d, J = 8.6 Hz, 1H) |
|---|---|
| 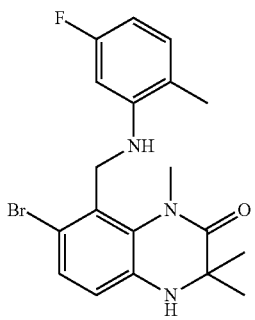 | |

Reference Example 5

5-Hydroxy-2-iodoanisole

Reference Compound No. 5

A mixture of 3-methoxyphenol (600 mg, 4.63 mmol) and N-iodosuccinimide (1.09 g, 4.84 mmol) was dissolved in anhydrous N,N-dimethylformamide (25 mL), and the mixture was stirred at room temperature overnight. Ethyl acetate (100 mL) and diethylether (100 mL) were added. The organic layer was washed with 1% aqueous sodium thiosulfate solution (200 mL) water (100 mL), and saturated brine (50 mL), dried over anhydrous magnesium sulfate, and then the solvent was removed under reduced pressure. The obtained residue was purified by silica gel column chromatography (hexane-ethyl acetate) to give the titled reference compound (167 mg) as a colorless (Yield 14%)

| 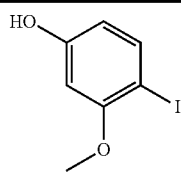 | ¹H-NMR (400 MHz, CDCl₃) δ 3.85 (s, 3H), 4.82 (s, 1 H), 6.25 (dd, J = 8.4, 2.7 Hz, 1H), 6.40 (d, J = 2.7 Hz, 1H), 7.56 (d, J = 8.4 Hz, 1H) |
|---|---|

Reference Example 6

2-Iodo-5-methoxymethoxyanisole

Reference Compound No. 6

A mixture of 5-hydroxy-2-iodoanisole (Reference Compound No. 5, 4.30 g, 17.2 mmol), chlorodimethylether (2.46 mL, 32.4 mmol), and potassium carbonate (5.94 g, 43.0 mmol) was suspended in anhydrous N,N-dimethylformamide (80 mL) and stirred at 50° C. for 1.5 hours. After cooling down, the reaction mixture was diluted with ethyl acetate (100 mL) and diethylether (200 mL). It was washed with water (300 mL), then the aqueous layer was extracted with diethylether (100 mL). After the organic layers were combined, washed with water (200 mL, twice) and saturated brine (100 mL) successively, dried over anhydrous magnesium sulfate, and then the solvent was removed under reduced pressure. The obtained residue was purified by silica gel column chromatography (hexane-ethyl acetate) to give the titled reference compound (958 mg) as a colorless oil. (Yield 19%)

| 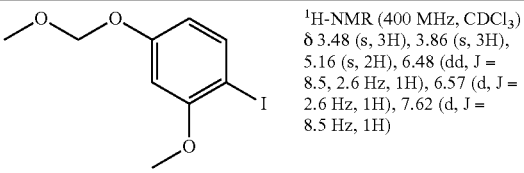 | ¹H-NMR (400 MHz, CDCl₃) δ 3.48 (s, 3H), 3.86 (s, 3H), 5.16 (s, 2H), 6.48 (dd, J = 8.5, 2.6 Hz, 1H), 6.57 (d, J = 2.6 Hz, 1H), 7.62 (d, J = 8.5 Hz, 1H) |
|---|---|

Reference Example 7

2-Methoxy-4-methoxymethoxyphenylboronic acid

Reference Compound No. 7-1

A mixture of 2-iodo-5-methoxymethoxyanisole (Reference Compound No. 6, 100 mg, 0.340 mmol), bis(neopentylglycolate)diborane (115 mg, 0.509 mmol), potassium acetate (66.7 mg, 0.680 mmol), and [1,1'-bis(diphenylphosphino)ferrocene]palladium(II)dichloride dichloromethane complex (1:1) (27.8 mg, 0.034 mmol) was suspended in dimethylsulfoxide (1.5 mL), and the mixture was stirred at 80° C. for 2.5 hours. After cooling down, ethyl acetate (100 mL) and water (100 mL) were added to the reaction mixture and partitioned. The organic layer was washed with saturated brine (50 mL), dried over anhydrous magnesium sulfate, and then the solvent was removed under reduced pressure. The obtained residue was purified by silica gel column chromatography (hexane-ethyl acetate) to give the titled reference compound (57.6 mg) as a colorless solid. (Yield 80)

| 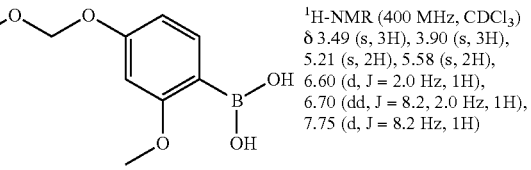 | ¹H-NMR (400 MHz, CDCl₃) δ 3.49 (s, 3H), 3.90 (s, 3H), 5.21 (s, 2H), 5.58 (s, 2H), 6.60 (d, J = 2.0 Hz, 1H), 6.70 (dd, J = 8.2, 2.0 Hz, 1H), 7.75 (d, J = 8.2 Hz, 1H) |
|---|---|

Using available compounds, the following Reference Compound (No. 7-2) was obtained by a method similar to that of Reference Compound No. 7-1.

| 2-(5,5-Dimethyl[1,3,2]dioxaborinan-2-yl)-5-nitroanisole (Reference Compound No. 7-2) 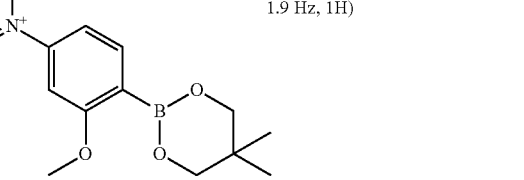 | ¹H-NMR (500 MHz, DMSO-d₆) δ 0.98 (s, 6H), 3.47 (s, 4H), 3.86 (s, 3H), 7.67 (d, J = 1.9 Hz, 1H), 7.69 (d, J = 8.0 Hz, 1H), 7.77 (dd, J = 8.0, 1.9 Hz, 1H) |
|---|---|

Reference Example 8

8-(5-Fluoro-2-methylphenoxymethyl)-7-(2-methoxy-4-methoxymethoxyphenyl)-1,3,3-trimethyl-3,4-dihydro-1H-quinoxalin-2-one

Reference Compound No. 8-1

Under argon atmosphere, a mixture 7-bromo-8-(5-fluoro-2-methylphenoxymethyl)-1,3,3-trimethyl-3,4-dihydro-1H-quinoxalin-2-one (Reference Compound No. 3-1, 2.32 g, 5.70 mmol), 2-methoxy-4-methoxymethoxyphenylboronic acid (Reference Compound No. 7-1, 2.43 g, 11.5 mmol), cesium carbonate (9.46 g, 29.0 mmol), and bis(triphenylphosphine)palladium (II) dichloride (415 mg, 0.591 mmol) was suspended in anhydrous N,N-dimethylformamide (25 ml) and the mixture was stirred at 80° C. for 5 hours. After cooling down, ethyl acetate (150 mL) and water (150 mL) were added and partitioned. The organic layer was washed with saturated brine (150 mL), dried over anhydrous magnesium sulfate, and then the solvent was removed under reduced pressure. The obtained residue was purified by silica gel column chromatography (hexane-ethyl acetate) to give the titled reference compound (2.73 g) as a colorless solid. (Yield 97%)

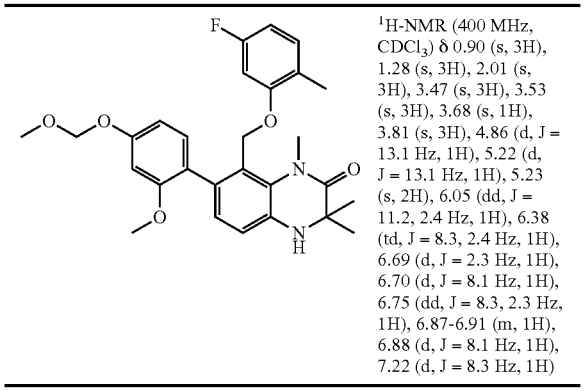

¹H-NMR (400 MHz, CDCl₃) δ 0.90 (s, 3H), 1.28 (s, 3H), 2.01 (s, 3H), 3.47 (s, 3H), 3.53 (s, 3H), 3.68 (s, 1H), 3.81 (s, 3H), 4.86 (d, J = 13.1 Hz, 1H), 5.22 (d, J = 13.1 Hz, 1H), 5.23 (s, 2H), 6.05 (dd, J = 11.2, 2.4 Hz, 1H), 6.38 (td, J = 8.3, 2.4 Hz, 1H), 6.69 (d, J = 2.3 Hz, 1H), 6.70 (d, J = 8.1 Hz, 1H), 6.75 (dd, J = 8.3, 2.3 Hz, 1H), 6.87-6.91 (m, 1H), 6.88 (d, J = 8.1 Hz, 1H), 7.22 (d, J = 8.3 Hz, 1H)

Using any compounds among Reference Compounds No. 1-(6), 3-1~3-3, 4-1, 4-2, 7-1, 7-2 and available compounds, the following Reference Compounds (No. 8-2~8-7) were obtained by a method similar to that of Reference Compound No. 8-1.

7-(2-Methoxy-4-methoxymethoxyphenyl)-8-(2-methoxy-5-nitrophenoxymethyl)-1,3,3-trimethyl-3,4-dihydro-1H-quinoxalin-2-one (Reference Compound No. 8-2)

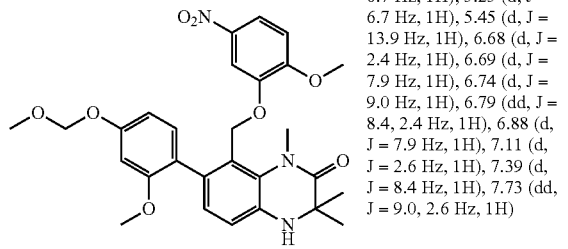

¹H-NMR (400 MHz, CDCl₃) δ 0.68 (s, 3H), 1.33 (s, 3H), 3.53 (s, 6H), 3.65 (s, 1H), 3.81 (s, 3H), 3.85 (s, 3H), 5.00 (d, J = 13.9 Hz, 1H), 5.22 (d, J = 6.7 Hz, 1H), 5.25 (d, J = 6.7 Hz, 1H), 5.45 (d, J = 13.9 Hz, 1H), 6.68 (d, J = 2.4 Hz, 1H), 6.69 (d, J = 7.9 Hz, 1H), 6.74 (d, J = 9.0 Hz, 1H), 6.79 (dd, J = 8.4, 2.4 Hz, 1H), 6.88 (d, J = 7.9 Hz, 1H), 7.11 (d, J = 2.6 Hz, 1H), 7.39 (d, J = 8.4 Hz, 1H), 7.73 (dd, J = 9.0, 2.6 Hz, 1H)

7-(2-Methoxy-4-methoxymethoxyphenyl)-8-(2-methyl-5-nitrophenoxymethyl)-1,3,3-trimethyl-3,4-dihydro-1H-quinoxalin-2-one (Reference Compound No. 8-3)

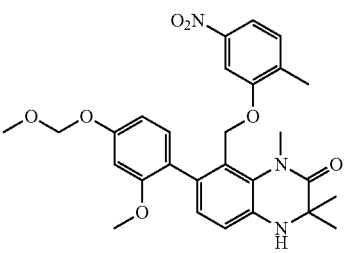

¹H-NMR (400 MHz, CDCl₃) δ 0.61 (s, 3H), 1.36 (s, 3H), 2.17 (s, 3H), 3.51 (s, 3H), 3.53 (s, 3H), 3.66 (s, 1H), 3.83 (s, 3H), 4.99 (d, J = 14.1 Hz, 1H), 5.22 (d, J = 6.8 Hz, 1H), 5.25 (d, J = 6.8 Hz, 1H), 5.45 (d, J = 14.1 Hz, 1H), 6.69 (d, J = 2.3 Hz, 1H), 6.70 (d, J = 8.1 Hz, 1H), 6.83 (dd, J = 8.4, 2.3 Hz, 1H), 6.91 (d, J = 8.1 Hz, 1H), 7.03 (d, J = 2.2 Hz, 1H), 7.09 (d, J = 8.1 Hz, 1H), 7.45 (d, J = 8.4 Hz, 1H), 7.57 (dd, J = 8.1, 2.2 Hz, 1H)

7-(2-Methoxy-4-methoxymethoxyphenyl)-8-(2-methoxyphenylaminomethyl)-1,3,3-trimethyl-3,4-dihydro-1H-quinoxalin-2-one (Reference Compound No. 8-4)

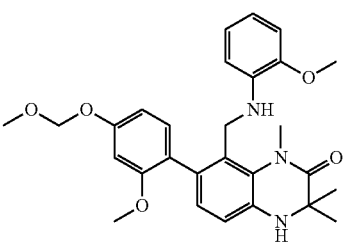

¹H-NMR (500 MHz, CDCl₃) δ 1.16 (s, 3H), 1.42 (s, 3H), 3.46 (s, 3H), 3.50 (s, 3H), 3.70 (s, 1H), 3.73 (s, 3H), 3.77 (s, 3H), 4.13 (d, J = 5.3 Hz, 2H), 4.52 (t, J = 5.3 Hz, 1H), 5.19 (s, 2H), 6.34 (dd, J = 7.6, 1.5 Hz, 1H), 6.56 (td, J = 7.6, 1.5 Hz, 1H), 6.61 (d, J = 2.4 Hz, 1H), 6.65-6.67 (m, 2H), 6.68 (d, J = 7.9 Hz, 1H), 6.72 (td, J = 7.6, 1.5 Hz, 1H), 6.80 (d, J = 7.9 Hz, 1H), 7.07 (d, J = 8.2 Hz, 1H)

8-(5-Fluoro-2-methylphenylaminomethyl)-7-(2-methoxy-4-methoxymethoxyphenyl)-1,3,3-trimethyl-3,4-dihydro-1H-quinoxalin-2-one (Reference Compound No. 8-5)

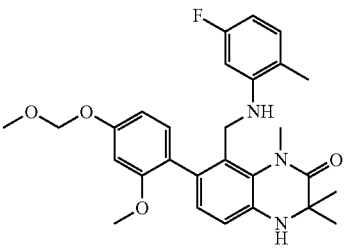

¹H-NMR (400 MHz, CDCl₃) δ 1.17 (s, 3H), 1.40 (s, 3H), 1.85 (s, 3H), 3.42 (s, 3H), 3.51 (s, 3H), 3.73 (s, 1H), 3.77 (s, 3H), 3.83 (br s, 1H), 4.13-4.23 (m, 2H), 5.20 (s, 2H), 6.03 (dd, J = 11.7, 2.5 Hz, 1H), 6.22 (td, J = 8.4, 2.5 Hz, 1H), 6.65 (d, J = 2.3 Hz, 1H), 6.70 (d, J = 7.8 Hz, 1H), 6.71 (dd, J = 8.3, 2.3 Hz, 1H), 6.81-6.85 (m, 1H), 6.83 (d, J = 7.8 Hz, 1H), 7.11 (d, J = 8.3 Hz, 1H)

8-(5-Fluoro-2-methylphenoxymethyl)-7-(2-methoxy-4-nitrophenyl)-1,3,3-trimethyl-3,4-dihydro-1H-quinoxalin-2-one (Reference Compound No. 8-6)

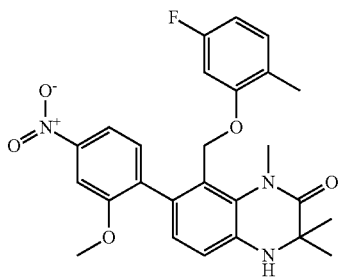

¹H-NMR (400 MHz, CDCl₃) δ 1.05 (s, 3H), 1.31 (s, 3H), 1.99 (s, 3H), 3.45 (s, 3H), 3.85 (s, 1H), 3.93 (s, 3H), 4.75 (d, J = 13.2 Hz, 1H), 5.15 (d, J = 13.2 Hz, 1H), 6.05 (dd, J = 11.0, 2.4 Hz, 1H), 6.43 (td, J = 8.3, 2.4 Hz, 1H), 6.76 (d, J = 8.1 Hz, 1H), 6.86 (d, J = 8.1 Hz, 1H), 6.92 (t, J = 7.6 Hz, 1H), 7.47 (d, J = 8.2 Hz, 1H), 7.83 (d, J = 2.2 Hz, 1H), 7.93 (dd, J = 8.2, 2.2 Hz, 1H)

| 8-Methoxycarbonyl-7-(2-methoxy-4-methoxymethoxyphenyl)-3,3-dimethyl-3,4-dihydro-1H-quinoxalin-2-one (Reference Compound No. 8-7) 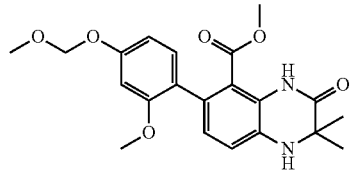 | ¹H-NMR (500 MHz, CDCl₃) δ 1.42 (br s, 6H), 3.52 (s, 3H), 3.54 (s, 3H), 3.70 (s, 3H), 3.81 (br s, 1H), 5.21 (s, 2H), 6.57 (d, J = 2.1 Hz, 1H), 6.69 (dd, J = 8.2, 2.1 Hz, 1H), 6.79 (d, J = 8.2 Hz, 1H), 6.82 (d, J = 6.2 Hz, 1H), 7.12 (d, J = 8.2 Hz, 1H), 9.51 (s, 1H) |

Reference Example 9

8-Hydroxymethyl-7-(2-methoxy-4-methoxymethoxyphenyl)-3,3-dimethyl-3,4-dihydro-1H-quinoxalin-2-one Reference Compound No. 9

Lithium aluminium hydride (753 mg, 19.8 mmol) was suspended in anhydrous tetrahydrofuran (60 mL) under nitrogen atmosphere. An anhydrous tetrahydrofuran solution (20 mL) of 8-methoxycarbonyl-7-(2-methoxy-4-methoxymethoxyphenyl)-3,3-dimethyl-3,4-dihydro-1H-quinoxalin-2-one (Reference Compound No. 8-7, 4.87 g, 12.2 mmol) was added dropwise thereto at −10° C., and stirred for 40 minutes at the same temperature. After ethyl acetate (10 mL), water (10 mL), and 2N aqueous hydrochloride solution (15 mL) were added to the reaction mixture successively, ethyl acetate (300 mL) were added thereto. Water (300 mL) was added and the whole was partitioned. The organic layer was washed with saturated brine (400 mL), dried over anhydrous magnesium sulfate, and then the solvent was removed under reduced pressure. The obtained residue was purified by silica gel column chromatography (hexane-ethyl acetate) to give the titled reference compound. (1.86 g) as a yellow solid. (Yield 41%)

| 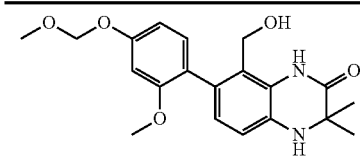 | ¹H-NMR (400 MHz, CDCl₃) δ 1.38 (s, 3H), 1.49 (s, 3H), 2 13 (t, J = 6.9 Hz, 1H), 3.53 (s, 3H), 3.75 (s, 4H), 4.45 (d, J = 6.9 Hz, 2H), 5.22 (s, 2H), 6.67 (d, J = 2.7 Hz, 1H), 6.67 (d, J = 8.1 Hz, 1H), 6.72 (dd, J = 8.0, 2.7 Hz, 1H), 6.72 (d, J = 8.0 Hz, 1H), 7.07 (d, J = 8.1 Hz, 1H), 8.57 (s, 1H) |

Reference Example 10

8-Chloromethyl-7-(2-methoxy-4-methoxymethoxyphenyl)-3,3-dimethyl-3,4-dihydro-1H-quinoxalin-2-one Reference Compound No. 10

8-Hydroxymethyl-7-(2-methoxy-4-methoxymethoxyphenyl)-3,3-dimethyl-3,4-dihydro-1H-quinoxalin-2-one (Reference Compound No. 9, 495 mg, 1.33 mmol) was dissolved in anhydrous dichloromethane (10 mL), and triethylamine (250 μL, 1.80 mmol) and methanesulfonyl chloride (113 μL, 1.46 mmol) were added thereto successively. The reaction mixture was stirred at room temperature overnight. The reaction mixture was concentrated under reduced pressure. The obtained residue was purified by silica gel column chromatography (hexane-ethyl acetate) to give the titled reference compound (239 mg) as a yellow amorphous product. (Yield 46%)

| 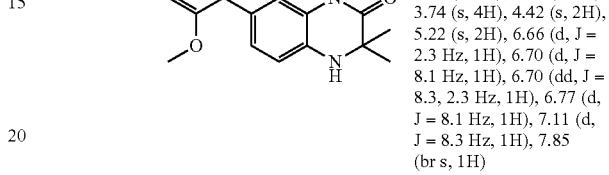 | ¹H-NMR (400 MHz, CDCl₃) δ 1.44 (s, 3H), 1.45 (s, 3H), 3.53 (s, 3H), 3.74 (s, 4H), 4.42 (s, 2H), 5.22 (s, 2H), 6.66 (d, J = 2.3 Hz, 1H), 6.70 (d, J = 8.1 Hz, 1H), 6.70 (dd, J = 8.3, 2.3 Hz, 1H), 6.77 (d, J = 8.1 Hz, 1H), 7.11 (d, J = 8.3 Hz, 1H), 7.85 (br s, 1H) |

Reference Example 11

7-(2-Methoxy-4-methoxymethoxyphenyl)-8-(5-methylthiophen-2-ylcarbonyloxymethyl)-3,3-dimethyl-3,4-dihydro-1H-quinoxalin-2-one Reference Compound No. 11

A mixture of 8-chloromethyl-7-(2-methoxy-4-methoxymethoxyphenyl)-3,3-dimethyl-3,4-dihydro-1H-quinoxalin-2-one (Reference Compound No. 10, 238 mg, 0.609 mmol), 5-methyl-2-thiophenecarboxylic acid (133 mg, 0.936 mmol), and potassium carbonate (261 mg, 1.89 mmol) was suspended in anhydrous N,N-dimethylformamide (5 ml) and stirred at 80° C. for 2 hours. The reaction mixture was diluted with ethyl acetate (100 mL). It was washed with water (100 mL) and saturated brine (100 mL) successively, dried over anhydrous magnesium sulfate, and then the solvent was removed under reduced pressure. The obtained residue was purified by silica gel, column chromatography (hexane-ethyl acetate) to give the titled reference compound (264 mg) as a yellow amorphous product. (Yield 87%)

| 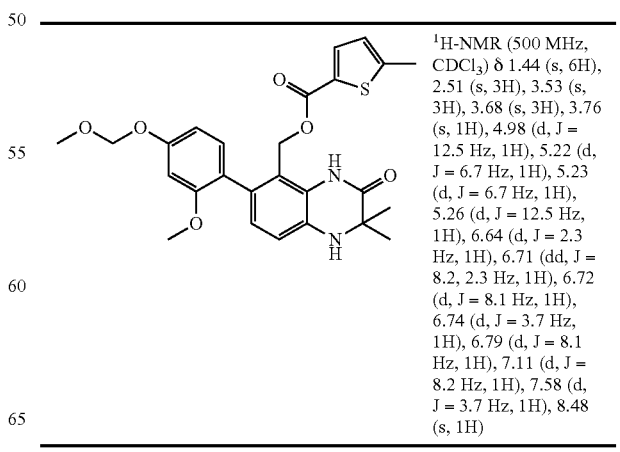 | ¹H-NMR (500 MHz, CDCl₃) δ 1.44 (s, 6H), 2.51 (s, 3H), 3.53 (s, 3H), 3.68 (s, 3H), 3.76 (s, 1H), 4.98 (d, J = 12.5 Hz, 1H), 5.22 (d, J = 6.7 Hz, 1H), 5.23 (d, J = 6.7 Hz, 1H), 5.26 (d, J = 12.5 Hz, 1H), 6.64 (d, J = 2.3 Hz, 1H), 6.71 (dd, J = 8.2, 2.3 Hz, 1H), 6.72 (d, J = 8.1 Hz, 1H), 6.74 (d, J = 3.7 Hz, 1H), 6.79 (d, J = 8.1 Hz, 1H), 7.11 (d, J = 8.2 Hz, 1H), 7.58 (d, J = 3.7 Hz, 1H), 8.48 (s, 1H) |

Reference Example 12

7-(2-Methoxy-4-methoxymethoxyphenyl)-8-(5-methylthiophen-2-ylcarbonyloxymethyl)-1,3,3-trimethyl-3,4-dihydro-1H-quinoxalin-2-one Reference Compound No. 12-1

A mixture of 7-(2-methoxy-4-methoxymethoxyphenyl)-8-(5-methylthiophen-2-ylcarbonyloxymethyl)-3,3-dimethyl-3,4-dihydro-1H-quinoxalin-2-one (Reference Compound No. 11, 1.58 g, 3.18 mmol), methyl iodide (400 μL, 6.43 mmol), and cesium carbonate (2.24 g, 6.87 mmol) was suspended in anhydrous N,N-dimethylformamide (30 mL) and stirred at room temperature for 2 hours. The reaction mixture was diluted with ethyl acetate (150 mL), washed with water (150 mL) and saturated brine (150 mL) successively, dried over anhydrous magnesium sulfate, and then the solvent was removed under reduced pressure. The obtained residue was purified by silica gel column chromatography (hexane-ethyl acetate) to give the titled reference compound (1.38 g) as a pale yellow amorphous product. (Yield 85%)

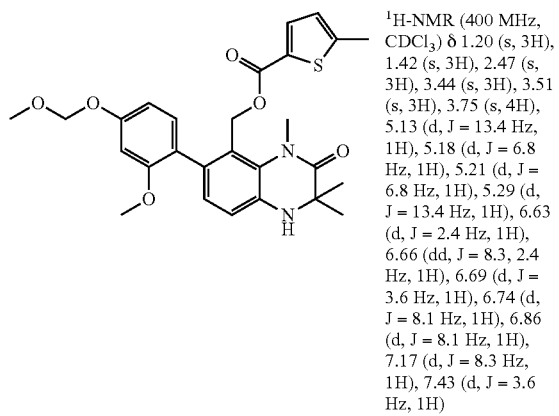

¹H-NMR (400 MHz, CDCl₃) δ 1.20 (s, 3H), 1.42 (s, 3H), 2.47 (s, 3H), 3.44 (s, 3H), 3.51 (s, 3H), 3.75 (s, 4H), 5.13 (d, J = 13.4 Hz, 1H), 5.18 (d, J = 6.8 Hz, 1H), 5.21 (d, J = 6.8 Hz, 1H), 5.29 (d, J = 13.4 Hz, 1H), 6.63 (d, J = 2.4 Hz, 1H), 6.66 (dd, J = 8.3, 2.4 Hz, 1H), 6.69 (d, J = 3.6 Hz, 1H), 6.74 (d, J = 8.1 Hz, 1H), 6.86 (d, J = 8.1 Hz, 1H), 7.17 (d, J = 8.3 Hz, 1H), 7.43 (d, J = 3.6 Hz, 1H)

Using any compounds among Reference Compound No. 9 and available compounds, the following Reference Compound (No. 12-2) was obtained by a method similar to that of Reference Compound No. 12-1.

| 8-Hydroxymethyl-7-(2-methoxy-4-methoxyphenyl)-1,3,3-trimethyl-3,4-dihydro-1H-quinoxalin-2-one (Reference Compound No. 12-2) 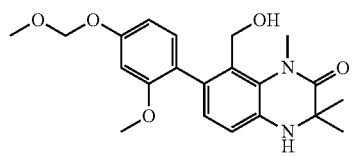 | ¹H-NMR (400 MHz, CDCl₃) δ 1.21 (s, 3H), 1.46 (s, 3H), 2.85 (dd, J = 8.9, 3.6 Hz, 1H), 3.54 (s, 3H), 3.65 (s, 3H), 3.72 (br s, 1H), 3.78 (s, 3H), 4.35 (dd, J = 12.3, 3.6 Hz, 1H), 4.44 (dd, J = 12.3, 8.9 Hz, 1H), 5.23 (s, 2H), 6.71 (d, J = 7.8 Hz, 1H), 6.72 (d, J = 2.0 Hz, 1H), 6.74 (dd, J = 8.0, 2.0 Hz, 1H), 6.78 (d, J = 7.8 Hz, 1H), 7.05 (d, J = 8.0 Hz, 1H) |

Reference Example 13

8-[N-(9-Fluorenylmethoxycarbonyl)-N-(2-methoxyphenyl)aminomethyl]-7-(2-methoxy-4-methoxymethoxyphenyl)-1,3,3-trimethyl-3,4-dihydro-1H-quinoxalin-2-one Reference Compound No. 13

7-(2-Methoxy-4-methoxymethoxyphenyl)-8-(2-methoxyphenylaminomethyl)-1,3,3-trimethyl-3,4-dihydro-1H-quinoxalin-2-one (Reference Compound No. 8-4, 104 mg, 0.212 mmol) and sodium hydrogen carbonate (22.0 mg, 0.262 mmol) were dissolved in mixed solvent of 1,4-dioxane (1.5 mL) and water (1 mL), and 9-fluorenylmethoxycarbonyl chloride (60.3 mg, 0.233 mmol) was added thereto. After the reaction mixture was stirred at room temperature for 30 minutes, the mixture was diluted with ethyl acetate (50 mL). The mixture was washed with water (50 mL) and saturated brine (50 mL) successively, dried over anhydrous magnesium sulfate, and then the solvent was removed under reduced pressure. The obtained residue was purified by silica gel column chromatography (hexane-ethyl acetate) to give the titled reference compound (149 mg) a colorless amorphous product. (Yield 99%)

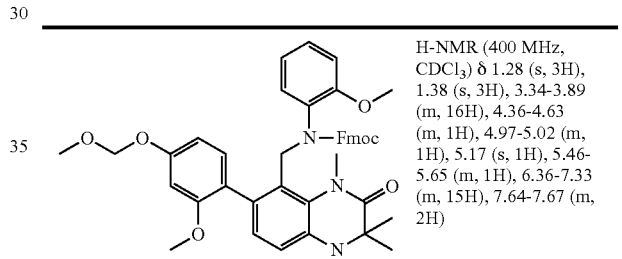

H-NMR (400 MHz, CDCl₃) δ 1.28 (s, 3H), 1.38 (s, 3H), 3.34-3.89 (m, 16H), 4.36-4.63 (m, 1H), 4.97-5.02 (m, 1H), 5.17 (s, 1H), 5.46-5.65 (m, 1H), 6.36-7.33 (m, 15H), 7.64-7.67 (m, 2H)

Reference Example 14

8-(5-Fluoro-2-methylphenoxymethyl)-7-(4-hydroxy-2-methoxyphenyl)-1,3,3-trimethyl-3,4-dihydro-1H-quinoxalin-2-one Reference Compound No. 14-1

8-(5-Fluoro-2-methylphenoxymethyl)-7-(2-methoxy-4-methoxymethoxyphenyl)-1,3,3-trimethyl-3,4-dihydro-1H-quinoxalin-2-one (Reference Compound No. 8-1, 2.73 g, 5.52 mmol) was dissolved in a mixed solution of 1,4-dioxane (25 mL) and methanol (5 mL), and 4N hydrochloride/1,4-dioxane solution (7.0 mL, 28 mmol) was added thereto. After the reaction mixture was stirred at room temperature for 1 hour, the mixture as diluted with ethyl acetate (130 mL). The mixture was washed with aqueous sodium hydrogen carbonate solution (130 mL) and saturated brine (100 mL) successively, dried over anhydrous magnesium sulfate, and then the solvent was removed under reduced pressure to give the titled reference compound (2.41 g) as a pale yellow solid. (Yield 97%)

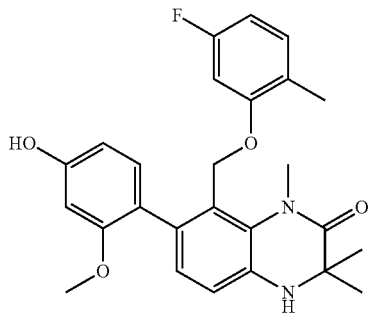 [SMILES: COc1cc(O)ccc1-c1ccc2c(c1COc1cc(F)ccc1C)N(C)C(=O)C(C)(C)N2]

¹H-NMR (400 MHz, CDCl₃) δ 0.91 (s, 3H), 1.28 (s, 3H), 2.02 (s, 3H), 3.47 (s, 3H), 3.68 (br s, 1H), 3.80 (s, 3H), 4.85 (d, J = 13.4 Hz, 1H), 4.92 (s, 1H), 5.21 (d, J = 13.4 Hz, 1H), 6.05 (dd, J = 11.4, 2.5 Hz, 1H), 6.38 (td, J = 8.4, 2.5 Hz, 1H), 6.50-6.53 (m, 2H), 6.70 (d, J = 8.1 Hz, 1H), 6.87 (d, J = 8.1 Hz, 1H), 6.87-6.91 (m, 1H), 7.16 (d, J = 8.3 Hz, 1H)

Using any compounds among Reference Compounds No. 3-4, 8-2, 8-3, 8-5, 12-1 and 13, the following Reference Compounds (No. 14-2~14-7) were obtained by a method similar to that of Reference Compound No. 14-1.

7-(4-Hydroxy-2-methoxyphenyl)-8-(2-methoxy-5-nitrophenoxymethyl)-1,3,3-trimethyl-3,4-dihydro-1H-quinoxalin-2-one (Reference Compound No. 14-2)

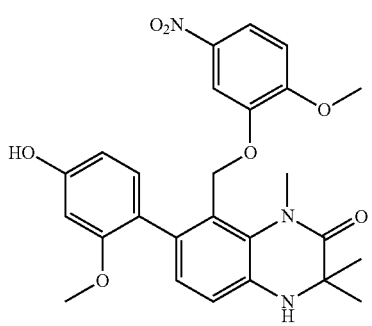

¹H-NMR (400 MHz, CDCl₃) δ 0.67 (s, 3H), 1.34 (s, 3H), 3.54 (s, 3H), 3.64 (s, 1H), 3.81 (s, 3H), 3.85 (s, 3H), 4.99 (d, J = 14.0 Hz, 1H), 5.10 (s, 1H), 5.45 (d, J = 14.0 Hz, 1H), 6.53 (d, J = 2.4 Hz, 1H), 6.57 (dd, J = 8.2, 2.4 Hz, 1H), 6.69 (d, J = 7.9 Hz, 1H), 6.74 (d, J = 9.0 Hz, 1H), 6.88 (d, J = 7.9 Hz, 1H), 7.09 (d, J = 2.7 Hz, 1H), 7.34 (d, J = 8.2 Hz, 1H), 7.72 (dd, J = 9.0, 2.7 Hz, 1H)

7-(4-Hydroxy-2-methoxyphenyl)-8-(2-methyl-5-nitrophenoxymethyl)-1,3,3-trimethyl-3,4-dihydro-1H-quinoxalin-2-one (Reference Compound No. 14-3)

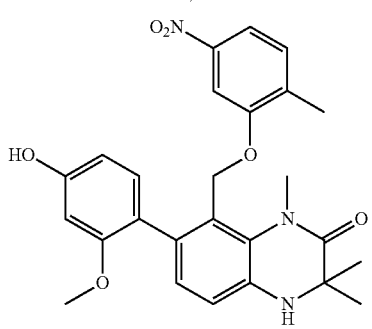

¹H-NMR (500 MHz, CDCl₃) δ 0.60 (s, 3H), 1.37 (s, 3H), 2.17 (s, 3H), 3.40-3.70 (m, 1H), 3.52 (s, 3H), 3.82 (s, 3H), 4.96 (s, 1H), 4.99 (d, J = 14.1 Hz, 1H), 5.45 (d, J = 14.1 Hz, 1H), 6.53 (d, J = 2.4 Hz, 1H), 6.60 (dd, J = 8.2, 2.4 Hz, 1H), 6.69 (d, J = 8.1 Hz, 1H), 6.90 (d, J = 8.1 Hz, 1H), 7.01 (d, J = 2.1 Hz, 1H), 7.09 (d, J = 8.2 Hz, 1H), 7.40 (d, J = 8.2 Hz, 1H), 7.57 (dd, J = 8.2, 2.1 Hz, 1H)

7-(4-Hydroxy-2-methoxyphenyl)-8-(5-methylthiophen-2-ylcarbonyloxymethyl)-1,3,3-trimethyl-3,4-dihydro-1H-quinoxalin-2-one (Reference Compound No. 14-4)

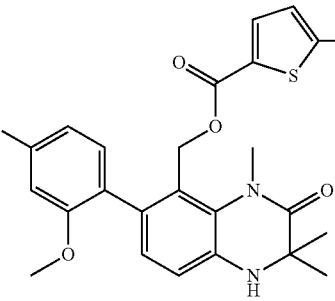

¹H-NMR (400 MHz, CDCl₃) δ 1.20 (s, 3H), 1.42 (s, 3H), 2.47 (s, 3H), 3.45 (s, 3H), 3.73 (s, 3H), 3.76 (s, 1H), 5.14 (d, J = 13.3 Hz, 1H), 5.17 (s, 1H), 5.27 (d, J = 13.3 Hz, 1H), 6.42 (dd, J = 8.2, 2.3 Hz, 1H), 6.46 (d, J = 2.3 Hz, 1H), 6.69 (d, J = 3.9 Hz, 1H), 6.74 (d, J = 8.0 Hz, 1H), 6.86 (d, J = 8.0 Hz, 1H), 7.11 (d, J = 8.2 Hz, 1H), 7.45 (d, J = 3.9 Hz, 1H)

7-(4-Hydroxy-2-methoxyphenyl)-8-(4-methylbenzoyloxymethyl)-1,3,3-trimethyl-3,4-dihydro-1H-quinoxalin-2-one (Reference Compound No. 14-5)

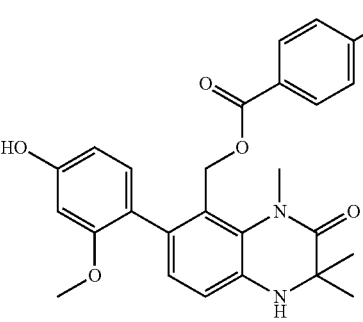

¹H-NMR (400 MHz, CDCl₃) δ 1.20 (s, 3H), 1.42 (s, 3H), 2.37 (s, 3H), 3.46 (s, 3H), 3.72 (s, 3H), 3.76 (s, 1H), 4.89 (s, 1H), 5.17 (d, J = 13.4 Hz, 1H), 5.31 (d, J = 13.4 Hz, 1H), 6.40 (dd, J = 8.1, 2.3 Hz, 1H), 6.45 (d, J = 2.3 Hz, 1H), 6.75 (d, J = 8.1 Hz, 1H), 6.87 (d, J = 8.1 Hz, 1H), 7.10 (d, J = 8.1 Hz, 1H), 7.16 (d, J = 8.2 Hz, 2H), 7.74 (d, J = 8.2 Hz, 2H)

8-[N-(9-Fluorenylmethoxycarbonyl)-N-(2-methoxyphenyl)-aminomethyl]-7-(4-hydroxy-2-methoxyphenyl)-1,3,3-trimethyl-3,4-dihydro-1H-quinoxalin-2-one (Reference Compound No. 14-6)

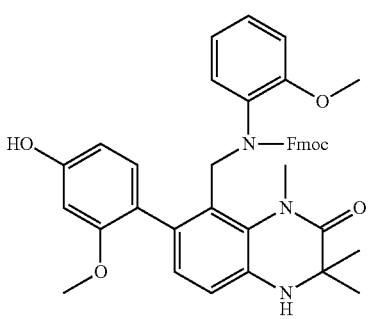

¹H-NMR (400 MHz, CDCl₃) δ 1.27 (s, 3H), 1.38 (s, 3H), 3.32 (s, 3H), 3.49-4.15 (m, 10H), 4.39-4.59 (m, 1H), 5.23-5.90 (m, 2H), 6.29-7.33 (m, 15H), 7.62-7.66 (m, 2H)

| | |
|---|---|
| 8-[N-(5-Fluoro-2-methylphenyl)-aminomethyl]-7-(4-hydroxy-2-methoxyphenyl)-1,3,3-trimethyl-3,4-dihydro-1H-quinoxalin-2-one (Reference Compound No. 14-7)<br />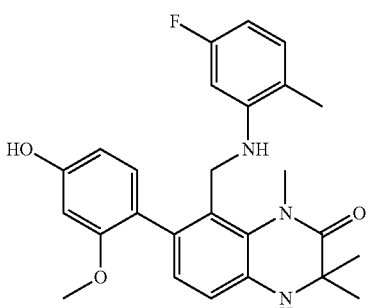 | ¹H-NMR (500 MHz, CDCl₃) δ 1.16 (s, 3H), 1.40 (s, 3H), 1.86 (s, 3H), 3.43 (s, 3H), 3.73 (s, 1H), 3.76 (s, 3H), 3.82-3.85 (m, 1H), 4.13 (dd, J = 13.9, 5.5 Hz, 1H), 4.20 (dd, J = 13.9, 5.0 Hz, 1H), 5.01 (s, 1H), 6.02 (dd, J = 11.8, 2.6 Hz, 1H), 6.22 (td, J = 8.3, 2.6 Hz, 1H), 6.47 (dd, J = 8.0, 2.4 Hz, 1H), 6.49 (d, J = 2.4 Hz, 1H), 6.70 (d, J = 7.9 Hz, 1H), 6.81-6.85 (m, 1H), 6.82 (d, J = 7.9 Hz, 1H), 7.05 (d, J = 8.0 Hz, 1H) |

Reference Example 15

7-(4-Amino-2-methoxyphenyl)-8-(5-fluoro-2-methylphenoxymethyl)-1,3,3-trimethyl-3,4-dihydro-1H-quinoxalin-2-one

Reference Compound No. 15

A mixture of 8-(5-fluoro-2-methylphenoxymethyl)-7-(2-methoxy-4-nitrophenyl)-1,3,3-trimethyl-3,4-dihydro-1H-quinoxalin-2-one (Reference Compound No. 8-6, 26.1 mg, 0.0544 mmol) and tin chloride (II) (64.8 mg, 0.342 mmol) was suspended in mixed solvent of anhydrous N,N-dimethylformamide (0.25 ml) and anhydrous ethanol (0.5 mL), and stirred at 80° C. for 3 days. After cooling down, the reaction mixture was diluted with ethyl acetate (10 mL) and saturated aqueous sodium hydrogen carbonate solution was added thereto until the pH became 9. After the precipitated solids were filtered out, the filtrate was washed with water (50 mL) and saturated brine (50 mL) successively, dried over anhydrous magnesium sulfate, and then the solvent was removed under reduced pressure. The obtained residue was purified by silica gel column chromatography (hexane-ethyl acetate) to give the titled reference compound (12.1 mg) as a brown solid. (Yield 50%)

| | |
|---|---|
| 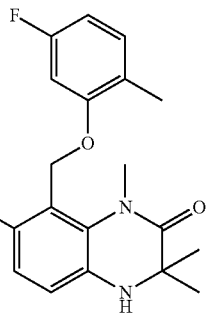 | ¹H-NMR (400 MHz, CDCl₃) δ 0.87 (s, 3H), 1.28 (s, 3H), 2.01 (s, 3H), 3.47 (s, 3H), 3.64 (s, 1H), 3.78 (s, 3H), 4.89 (d, J = 13.7 Hz, 1H), 5.23 (d, J = 13.7 Hz, 1H), 6.05 (dd, J = 11.2, 2.4 Hz, 1H), 6.33 (d, J = 2.2 Hz, 1H), 6.37 (td, J = 8.4, 2.4 Hz, 1H), 6.40 (dd, J = 8.0, 2.2 Hz, 1H), 6.68 (d, J = 8.1 Hz, 1H), 6.88 (d, J = 8.1 Hz, 1H), 6.88 (t, J = 7.6 Hz, 1H), 7.10 (d, J = 8.0 Hz, 1H) |

EXAMPLES

Example 1

8-(5-Fluoro-2-methylphenoxymethyl)-7-(2-methoxy-4-methylsulfonyloxyphenyl)-1,3,3-trimethyl-3,4-dihydro-1H-quinoxalin-2-one

Compound No. 1-1

8-(5-Fluoro-2-methylphenoxymethyl)-7-(4-hydroxy-2-methoxyphenyl)-1,3,3-trimethyl-3,4-dihydro-1H-quinoxalin-2-one (Reference Compound No. 14-1, 61.1 mg, 0.136 mmol) was dissolved in anhydrous dichloromethane (1 mL), and triethylamine (44 µL, 0.319 mmol) and methanesulfonyl chloride (13 µL, 0.168 mmol) were added thereto successively. The reaction mixture was stirred at room temperature for 3 hours and 15 minutes. The reaction mixture was purified by silica gel column chromatography (hexane-ethyl acetate) to give the titled compound (68.3 mg) as a colorless amorphous product. (Yield 98%)

| | |
|---|---|
| 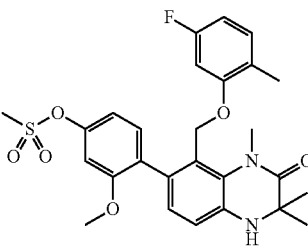 | ¹H-NMR (400 MHz, CDCl₃) δ 1.00 (s, 3H), 1.29 (s, 3H), 2.02 (s, 3H), 3.19 (s, 3H), 3.47 (s, 3H), 3.76 (s, 1H), 3.85 (s, 3H), 4.80 (d, J = 13.4 Hz, 1H), 5.17 (d, J = 13.4 Hz, 1H), 6.06 (dd, J = 1.2, 2.4 Hz, 1H), 6.42 (td, J = 8.3, 2.4 Hz, 1H), 6.74 (d, J = 8.1 Hz, 1H), 6.87 (d, J = 8.1 Hz, 1H), 6.90-6.93 (m, 1H), 6.94 (d, J = 2.2 Hz, 1H), 6.97 (dd, J = 8.2, 2.2 Hz, 1H), 7.34 (d, J = 8.2 Hz, 1H) |

Using any compounds among Reference Compounds No. 14-1~14-5, 14-7 and available compounds, the following Compounds (No. 1-2~1-58) were obtained by a method similar to that of Compound No. 1-1.

| Compound | NMR |
|---|---|
| 8-(5-Fluoro-2-methylphenoxymethyl)-7-(2-methoxy-4-phenylsulfonyloxyphenyl)-1,3,3-trimethyl-3,4-dihydro-1H-quinoxalin-2-one (Compound No. 1-2) 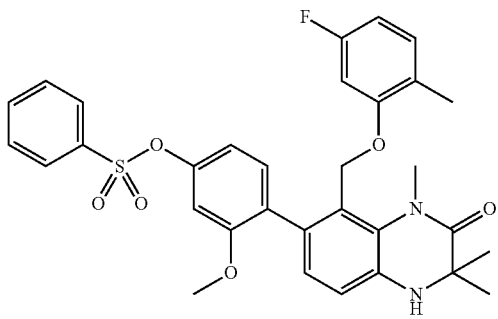 | $^1$H-NMR (400 MHz, CDCl$_3$) δ 0.99 (s, 3H), 1.28 (s, 3H), 2.00 (s, 3H), 3.43 (s, 3H), 3.68 (s, 3H), 3.74 (s, 1H), 4.69 (d, J = 13.2 Hz, 1H), 5.09 (d, J = 13.2 Hz, 1H), 6.01 (dd, J = 11.1, 2.4 Hz, 1H), 6.43 (td, J = 8.3, 2.4 Hz, 1H), 6.61-6.63 (m, 2H), 6.71 (d, J = 8.1 Hz, 1H), 6.83 (d, J = 8.1 Hz, 1H), 6.91-6.95 (m, 1H), 7.19 (d, J = 8.8 Hz, 1H), 7.47-7.52 (m, 2H), 7.64-7.68 (m, 1H), 7.83-7.85 (m, 2H) |
| 8-(5-Fluoro-2-methylphenoxymethyl)-7-(2-methoxy-4-trifluoromethylsulfonyloxyphenyl)-1,3,3-trimethyl-3,4-dihydro-1H-quinoxalin-2-one (Compound No. 1-3) 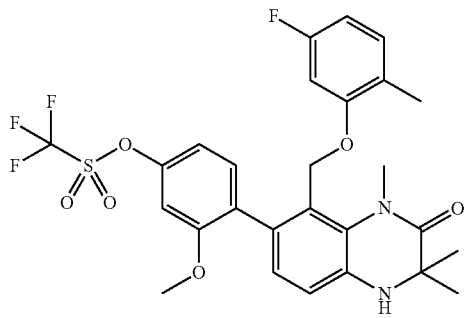 | $^1$H-NMR (500 MHz, CDCl$_3$) δ 1.02 (s, 3H), 1.28 (s, 3H), 2.00 (s, 3H), 3.45 (s, 3H), 3.77 (s, 1H), 3.84 (s, 3H), 4.77 (d, J = 13.3 Hz, 1H), 5.13 (d, J = 13.3 Hz, 1H), 6.05 (dd, J = 11.0, 2.4 Hz, 1H), 6.42 (td, J = 8.2, 2.4, 1H), 6.74 (d, J = 8.1 Hz, 1H), 6.85 (d, J = 8.1 Hz, 1H), 6.87 (d, J = 2.3 Hz, 1H), 6.90-6.93 (m, 1H), 6.96 (dd, J = 8.3, 2.3 Hz, 1H), 7.36 (d, J = 8.3 Hz, 1H) |
| 8-(5-Fluoro-2-methylphenoxymethyl)-7-(2-methoxy-4-propylsulfonyloxyphenyl)-1,3,3-trimethyl-3,4-dihydro-1H-quinoxalin-2-one (Compound No. 1-4) 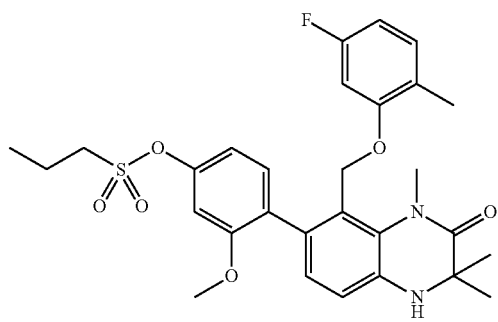 | $^1$H-NMR (400 MHz, CDCl$_3$) δ 0.97 (s, 3H), 1.15 (t, J = 7.5 Hz, 3H), 1.27 (s, 3H), 2.01 (s, 3H), 2.02-2.09 (m, 2H), 3.25-3.29 (m, 2H), 3.46 (s, 3H), 3.75 (s, 1H), 3.84 (s, 3H), 4.80 (d, J = 13.4 Hz, 1H), 5.17 (d, J = 13.4 Hz, 1H), 6.05 (dd, J = 11.1, 2.4 Hz, 1H), 6.40 (td, J = 8.3, 2.4, 1H), 6.73 (d, J = 8.1 Hz, 1H), 6.66 (d, J = 8.1 Hz, 1H), 6.89-6.93 (m, 2H), 6.95 (d, J = 2.2 Hz, 1H), 7.32 (d, J = 8.3 Hz, 1H) |

| | |
|---|---|
| 8-(5-Fluoro-2-methylphenoxy-methyl)-7-[2-methoxy-4-(furan-2-ylsulfonyloxy)phenyl]-1,3,3-trimethyl-3,4-dihydro-1H-quinoxalin-2-one (Compound No. 1-5)<br/>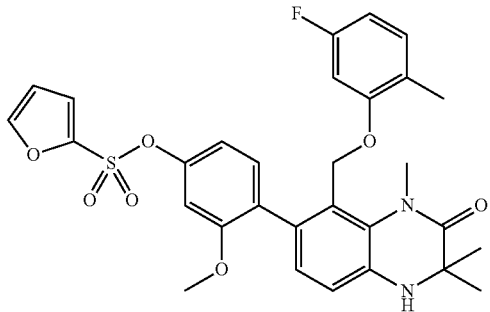 | $^1$H-NMR (500 MHz, CDCl$_3$) δ 1.01 (s, 3H), 1.28 (s, 3H), 2.00 (s, 3H), 3.44 (s, 3H), 3.75 (s, 4H), 4.70 (d, J = 13.1 Hz, 1H), 5.09 (d, J = 13.1 Hz, 1H), 6.02 (dd, J = 11.0, 2.4 Hz, 1H), 6.43 (td, J = 8.2, 2.4 Hz, 1H), 6.50 (dd, J = 3.7, 1.8 Hz, 1H), 6.68-6.70 (m, 2H), 6.72 (d, J = 8.1 Hz, 1H), 6.83 (d, J = 8.1 Hz, 1H), 6.92-6.95 (m, 1H), 7.01 (dd, J = 3.7, 0.9 Hz, 1H), 7.23 (dd, J = 7.6, 0.9 Hz, 1H), 7.66 (dd, J = 1.8, 0.9 Hz, 1H) |
| 7-(2-Methoxy-4-methylsulfonyl-oxyphenyl)-8-(5-methylthio-phen-2-ylcarbonyloxymethyl)-1,3,3-trimethyl-3,4-dihydro-1H-quinoxalin-2-one (Compound No. 1-6)<br/>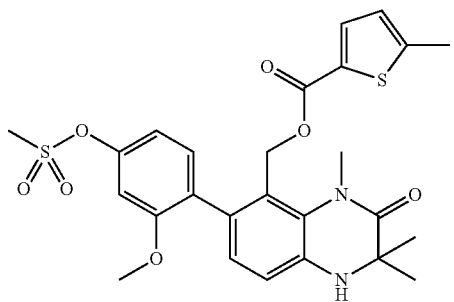 | $^1$H-NMR (400 MHz, CDCl$_3$) δ 1.23 (s, 3H), 1.41 (s, 3H), 2.48 (s, 3H), 3.16 (s, 3H), 3.46 (s, 3H), 3.75 (s, 3H), 3.81 (s, 1H), 5.08 (d, J = 13.3 Hz, 1H), 5.23 (d, J = 13.3 Hz, 1H), 6.70 (d, J = 3.8 Hz, 1H), 6.76 (d, J = 8.1 Hz, 1H), 6.84 (d, J = 8.1 Hz, 1H), 6.87 (s, 1H), 6.87-6.89 (m, 1H), 7.26-7.29 (m, 1H), 7.42 (d, J = 3.8 Hz, 1H) |
| 7-(2-methoxy-4-phenylsulfonyl-oxyphenyl)-8-(5-methylthio-phen-2-ylcarbonyloxymethyl)-1,3,3-trimethyl-3,4-dihydro-1H-quinoxalin-2-one (Compound No. 1-7)<br/>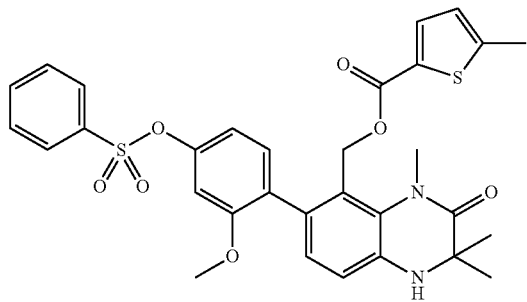 | $^1$H-NMR (400 MHz, CDCl$_3$) δ 1.23 (s, 3H), 1.40 (s, 3H), 2.48 (s, 3H), 3.43 (s, 3H), 3.60 (s, 3H), 3.80 (s, 1H), 4.98 (d, J = 13.1 Hz, 1H), 5.19 (d, J = 13.1 Hz, 1H), 6.51 (d, J = 2.2 Hz, 1H), 6.57 (dd, J = 8.3, 2.2 Hz, 1H), 6.71 (d, J = 3.8 Hz, 1H), 6.74 (d, J = 8.0 Hz, 1H), 6.81 (d, J = 8.0 Hz, 1H), 7.15 (d, J = 8.3 Hz, 1H), 7.44 (d, J = 3.8 Hz, 1H), 7.53 (t, J = 7.5 Hz, 2H), 7.65 (t, J = 7.5 Hz, 1H), 7.85 (d, J = 7.5 Hz, 2H) |

| Compound | ¹H-NMR |
|---|---|
| 7-[4-(2-Chlorophenylsulfonyl-oxy)-2-methoxyphenyl]-8-(5-fluoro-2-methylphenoxymethyl)-1,3,3-trimethyl-3,4-dihydro-1H-quinoxalin-2-one (Compound No. 1-8)<br />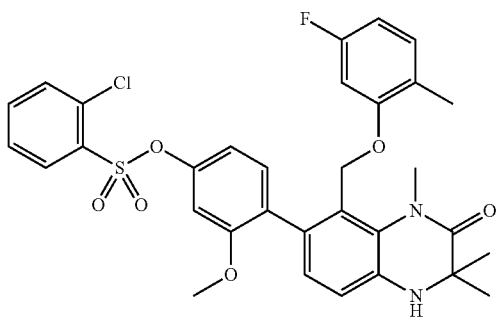 | ¹H-NMR (400 MHz, CDCl₃) δ 0.98 (s, 3H), 1.28 (s, 3H), 1.99 (s, 3H), 3.42 (s, 3H), 3.72 (s, 1H), 3.74 (s, 3H), 4.66 (d, J = 13.2 Hz, 1H), 5.07 (d, J = 13.2 Hz, 1H), 5.97 (dd, J = 11.2, 2.5 Hz, 1H), 6.43 (td, J = 8.4, 2.5 Hz, 1H), 6.70 (d, J = 8.1 Hz, 1H), 6.77 (dd, J = 8.3, 2.6 Hz, 1H), 6.79 (d, J = 2.6 Hz, 1H), 6.81 (d, J = 8.1 Hz, 1H), 6.90-6.94 (m, 1H), 7.19 (d, J = 8.3 Hz, 1H), 7.32 (ddd, J = 8.0, 7.3, 1.4 Hz, 1H), 7.56 (ddd, J = 8.0, 7.3, 1.4 Hz, 1H), 7.62 (dd, J = 8.0, 1.4 Hz, 1H), 7.94 (dd, J = 8.0, 1.4 Hz, 1H) |
| 7-(4-Benzylsulfonyloxy-2-methoxyphenyl)-8-(5-fluoro-2-methylphenoxymethyl)-1,3,3-trimethyl-3,4-dihydro-1H-quinoxalin-2-one (Compound No. 1-9)<br />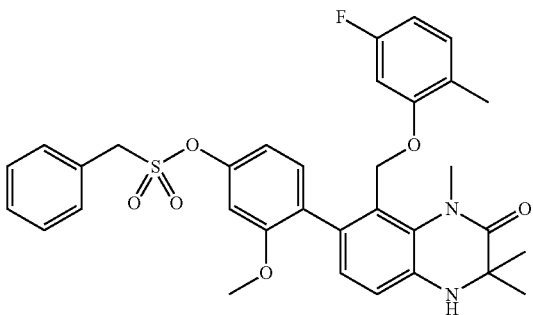 | ¹H-NMR (500 MHz, CDCl₃) δ 0.97 (s, 3H), 1.26 (s, 3H), 2.01 (s, 3H), 3.45 (s, 3H), 3.73 (s, 1H), 3.74 (s, 3H), 4.56 (s, 2H), 4.78 (d, J = 13.4 Hz, 1H), 5.14 (d, J = 13.4 Hz, 1H), 6.04 (dd, J = 11.3, 2.4 Hz, 1H), 6.40 (td, J = 8.2, 2.4 Hz, 1H), 6.67 (d, J = 2.2 Hz, 1H), 6.71 (d, J = 7.9 Hz, 1H), 6.80 (dd, J = 8.3, 2.2 Hz, 1H), 6.83 (d, J = 7.9 Hz, 1H), 6.89-6.92 (m, 1H), 7.27 (d, J = 8.3 Hz, 1H), 7.42-7.45 (m, 3H), 7.47-7.50 (m, 2H) |
| 8-(5-Fluoro-2-methylphenoxymethyl)-7-[2-methoxy-4-(2-methoxycarbonylethylsulfonyloxy)-phenyl]-1,3,3-trimethyl-3,4-dihydro-1H-quinoxalin-2-one (Compound No. 1-10)<br />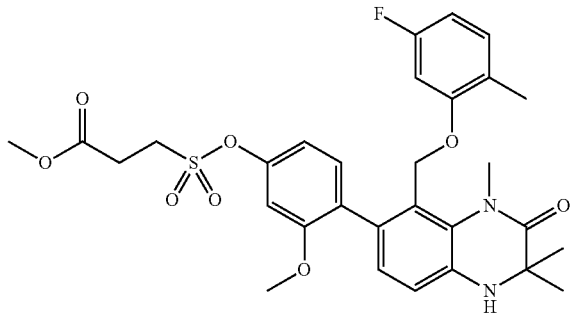 | ¹H-NMR (500 MHz, CDCl₃) 0.98 (s, 3H), 1.27 (s, 3H), 2.01 (s, 3H), 3.02 (t, J = 7.6 Hz, 2H), 3.46 (s, 3H), 3.65 (t, J = 7.6 Hz, 2H), 3.75 (s, 1H), 3.77 (s, 3H), 3.84 (s, 3H), 4.80 (d, J = 13.4 Hz, 1H), 5.16 (d, J = 13.4 Hz, 1H), 6.05 (dd, J = 11.3, 2.4 Hz, 1H), 6.40 (td, J = 8.2, 2.4 Hz, 1H), 6.73 (d, J = 7.9 Hz, 1H), 6.85 (d, J = 7.9 Hz, 1H), 6.89-6.92 (m, 1H), 6.92 (d, J = 2.3 Hz, 1H), 6.95 (dd, J = 8.2, 2.3 Hz, 1H), 7.33 (d, J = 8.2 Hz, 1H) |

| | |
|---|---|
| 8-(5-Fluoro-2-methylphenoxymethyl)-7-[2-methoxy-4-(2-methylphenylsulfonyloxy)phenyl]-1,3,3-trimethyl-3,4-dihydro-1H-quinoxalin-2-one (Compound No. 1-11) 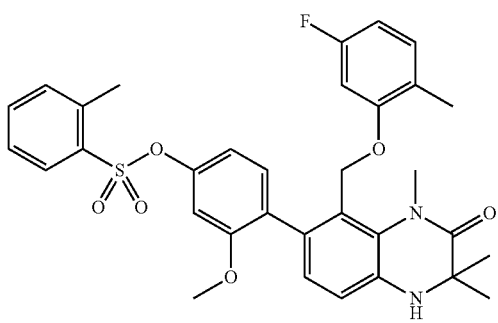 | $^1$H-NMR (400 MHz, CDCl$_3$) δ 0.98 (s, 3H), 1.28 (s, 3H), 1.99 (s, 3H), 2.77 (s, 3H), 3.42 (s, 3H), 3.68 (s, 3H), 3.70 (s, 1H), 4.69 (d, J = 13.3 Hz, 1H), 5.08 (d, J = 13.3 Hz, 1H), 5.99 (dd, J = 11.2, 2.4 Hz, 1H), 6.42 (td, J = 8.3, 2.4 Hz, 1H), 6.61 (dd, J = 8.1, 2.1 Hz, 1H), 6.63 (d, J = 2.1 Hz, 1H), 6.70 (d, J = 8.1 Hz, 1H), 6.81 (d, J = 8.1 Hz, 1H), 6.90-6.94 (m, 1H), 7.17 (d, J = 8.1 Hz, 1H), 7.23-7.28 (m, 1H), 7.40 (d, J = 7.6 Hz, 1H), 7.53 (td, J = 7.6, 1.3 Hz, 1H), 7.83 (dd, J = 8.1, 1.3 Hz, 1H) |
| 7-(4-Butylsulfonyloxy-2-methoxyphenyl)-8-(5-fluoro-2-methylphenoxymethyl)-1,3,3-trimethyl-3,4-dihydro-1H-quinoxalin-2-one (Compound No. 1-12) 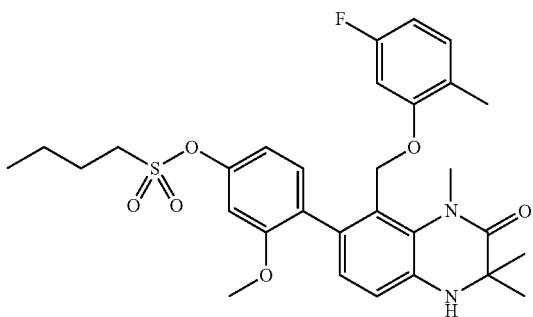 | $^1$H-NMR (500 MHz, CDCl$_3$) δ 0.97 (s, 3H), 1.00 (t, J = 7.3 Hz, 3H), 1.27 (s, 3H), 1.50-1.59 (m, 2H), 1.96-2.03 (m, 2H), 2.01 (s, 3H), 3.27-3.34 (m, 2H), 3.46 (s, 3H), 3.74 (s, 1H), 3.83 (s, 3H), 4.80 (d, J = 13.3 Hz, 1H), 5.17 (d, J = 13.3 Hz, 1H), 6.05 (dd, J = 11.0, 2.4 Hz, 1H), 6.40 (td, J = 8.3, 2.4 Hz, 1H), 6.73 (d, J = 7.9 Hz, 1H), 6.86 (d, J = 7.9 Hz, 1H), 6.89-6.92 (m, 2H), 6.94 (dd, J = 8.2, 2.3 Hz, 1H), 7.32 (d, J = 8.2 Hz, 1H) |
| 7-(4-Ethylsulfonyloxy-2-methoxyphenyl)-8-(5-fluoro-2-methylphenoxymethyl)-1,3,3-trimethyl-3,4-dihydro-1H-quinoxalin-2-one (Compound No. 1-13) 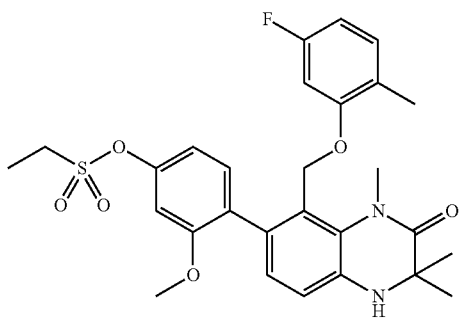 | $^1$H-NMR (400 MHz, CDCl$_3$) δ 0.98 (s, 3H), 1.28 (s, 3H), 1.57 (t, J = 7.4 Hz, 3H), 2.01 (s, 3H), 3.32 (q, J = 7.4 Hz, 2H), 3.46 (s, 3H), 3.75 (s, 1H), 3.84 (s, 3H), 4.80 (d, J = 13.4 Hz, 1H), 5.17 (d, J = 13.4 Hz, 1H), 6.05 (dd, J = 11.5, 2.4 Hz, 1H), 6.41 (td, J = 8.3, 2.4 Hz, 1H), 6.73 (d, 2 = 8.1 Hz, 1H), 6.86 (d, J = 81 Hz, 1H), 6.89-6.94 (m, 1H), 6.93 (d, J = 2.3 Hz, 1H), 6.95 (dd, J = 8.1, 2.3 Hz, 1H), 7.32 (d, J = 8.1 Hz, 1H) |

| | |
|---|---|
| 8-(5-Fluoro-2-methylphenoxy-methyl)-7-(4-isopropylsulfonyl-oxy-2-methoxyphenyl)-1,3,3-trimethyl-3,4-dihydro-1H-quinoxalin-2-one (Compound No. 1-14)<br>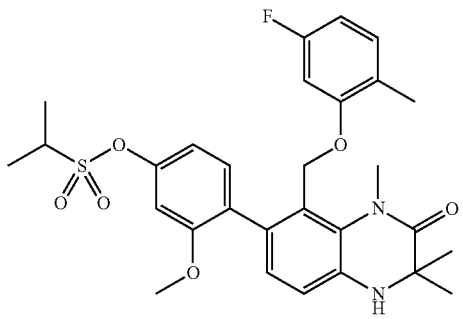 | $^1$H-NMR (400 MHz, CDCl$_3$) δ 0.97 (s, 3H), 1.28 (s, 3H), 1.59 (d, J = 6.9 Hz, 6H), 2.01 (s, 3H), 3.46 (s, 3H), 3.50 (septet, J = 6.9 Hz, 1H), 3.74 (s, 1H), 3.84 (s, 3H), 4.80 (d, J = 13.4 Hz, 1H), 5.17 (d, J = 13.4 Hz, 1H), 6.05 (dd, J = 11.2, 2.4 Hz, 1H), 6.40 (td, J = 8.3, 2.4 Hz, 1H), 6.73 (d, J = 8.0 Hz, 1H), 6.89 (d, J = 8.0 Hz, 1H), 6.89-6.93 (m, 1H), 6.92 (d, J = 2.3 Hz, 1H), 6.95 (dd, J = 8.3, 2.3 Hz, 1H), 7.32 (d, J = 6.3 Hz, 1H) |
| 8-(5-Fluoro-2-methylphenoxy-methyl)-7-[2-methoxy-4-(3-methoxyphenylsulfonyloxy)phenyl]-1,3,3-trimethyl-3,4-dihydro-1H-quinoxalin-2-one (Compound No. 1-15)<br>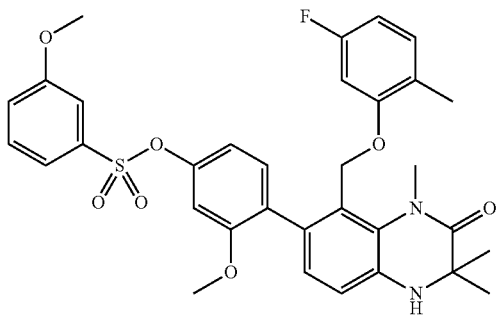 | $^1$H-NMR (400 MHz, CDCl$_3$) δ 0.96 (s, 3H), 1.28 (s, 3H), 2.00 (s, 3H), 3.44 (s, 3H), 3.71 (s, 3H), 3.74 (s, 1H), 3.80 (s, 3H), 4.72 (d, J = 13.4 Hz, 1H), 5.13 (d, J = 13.4 Hz, 1H), 5.99 (dd, J = 11.0, 2.4 Hz, 1H), 6.41 (td, J = 8.3, 2.4 Hz, 1H), 6.64 (dd, J = 8.2, 2.3 Hz, 1H), 6.67 (d, J = 2.3 Hz, 1H), 6.71 (d, J = 8.1 Hz, 1H), 6.82 (d, J = 8.1 Hz, 1H), 6.90-6.93 (m, 1H), 7.16-7.19 (m, 1H), 7.20 (d, J = 8.2 Hz, 1H), 7.38-7.41 (m, 3H) |
| 7-[4-(3-Chlorophenylsulfonyl-oxy)-2-methoxyphenyl]-8-(5-fluoro-2-methylphenoxymethyl)-1,3,3-trimethyl-3,4-dihydro-1H-quinoxalin-2-one (Compound No. 1-16)<br>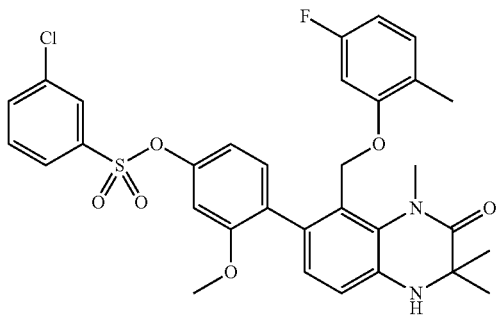 | $^1$H-NMR (500 MHz, CDCl$_3$) δ 0.99 (s, 3H), 1.28 (s, 3H), 2.00 (s, 3H), 3.44 (s, 3H), 3.73 (s, 3H), 3.74 (s, 1H), 4.72 (d, J = 13.3 Hz, 1H), 5.11 (d, J = 13.3 Hz, 1H), 6.01 (dd, J = 21.3, 2.4 Hz, 1H), 6.42 (td, J = 8.2, 2.4 Hz, 1H), 6.64 (dd, J = 8.2, 2.4 Hz, 1H), 6.67 (d, J = 2.4 Hz, 1H), 6.71 (d, J = 7.9 Hz, 1H), 6.83 (d, J = 7.9 Hz, 1H), 6.91-6.94 (m, 1H), 7.22 (d, J = 8.2 Hz, 1H), 7.42 (t, J = 7.9 Hz, 1H), 7.64 (ddd, J = 7.9, 1.8, 1.0 Hz, 1H), 7.70 (ddd, J = 7.9, 1.8, 1.0 Hz, 1H), 7.90 (t, J = 1.8 Hz, 1H) |

| | | |
|---|---|---|
| 7-[4-(4-Chlorophenylsulfonyl-oxy)-2-methoxyphenyl]-8-(5-fluoro-2-methylphenoxymethyl)-1,3,3-trimethyl-3,4-dihydro-1H-quinoxalin-2-one (Compound No. 1-17) | 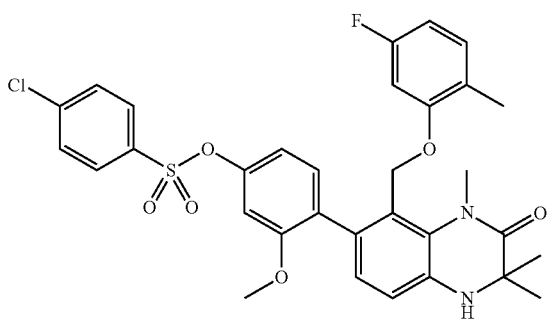 | $^1$H-NMR (500 MHz, CDCl$_3$) δ 1.00 (s, 3H), 1.28 (s, 3H), 2.00 (s, 3H), 3.44 (s, 3H), 3.73 (s, 3H), 3.75 (s, 1H), 4.70 (d, J = 13.1 Hz, 1H), 5.10 (d, J = 13.1 Hz, 1H), 6.03 (dd, J = 11.3, 2.4 Hz, 1H), 6.44 (td, J = 8.2, 2.4 Hz, 1H), 6.57 (dd, J = 8.2, 2.1 Hz, 1H), 6.67 (d, J = 2.1 Hz, 1H), 6.72 (d, J = 7.9 Hz, 1H), 6.82 (d, J = 7.9 Hz, 1H), 6.92-6.95 (m, 1H), 7.20 (d, J = 8.2 Hz, 1H), 7.46 (d, J = 8.9 Hz, 2H), 7.76 (t, J = 8.9 Hz, 2H) |
| 7-[4-(3-Chlorobenzylsulfonyl-oxy)-2-methoxyphenyl]-8-(5-fluoro-2-methylphenoxymethyl)-1,3,3-trimethyl-3,4-dihydro-1H-quinoxalin-2-one (Compound No. 1-18) | 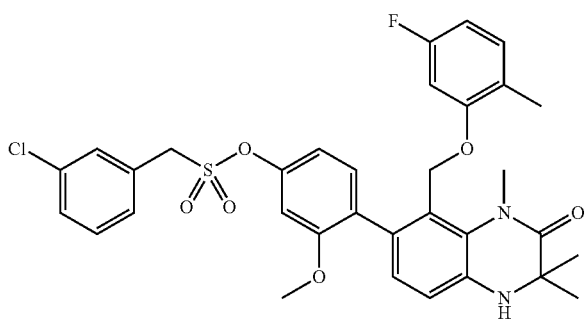 | $^1$H-NMR (400 MHz, CDCl$_3$) δ 0.98 (s, 3H), 1.27 (s, 3H), 2.01 (s, 3H), 3.45 (s, 3H), 3.75 (s, 1H), 3.78 (s, 3H), 4.51 (s, 2H), 4.78 (d, J = 13.4 Hz, 1H), 5.15 (d, J = 13.4 Hz, 1H), 6.04 (dd, J = 11.2, 2.4 Hz, 1H), 6.40 (td, J = 8.3, 2.4 Hz, 1H), 6.72 (d, J = 7.9 Hz, 1H), 6.72 (d, J = 2.3 Hz, 1H), 6.84 (d, J = 7.9 Hz, 1H), 6.84 (dd, J = 8.2, 2.3 Hz, 1H), 6.89-6.93 (m, 1H), 7.29 (d, J = 8.2 Hz, 1H), 7.36-7.43 (m, 3H), 7.48 (s, 1H) |
| 8-(5-Fluoro-2-methylphenoxy-methyl)-7-[2-methoxy-4-(4-methylbenzylsulfonlyoxy)phenyl]-1,3,3-trimethyl-3,4-dihydro-1H-quinoxalin-2-one (Compound No. 1-19) | 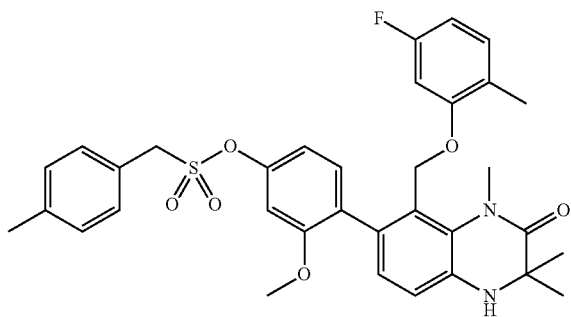 | $^1$H-NMR (400 MHz, CDCl$_3$) δ 0.96 (s, 3H), 1.26 (s, 3H), 2.01 (s, 3H), 2.38 (s, 3H), 3.45 (s, 3H), 3.75 (s, 4H), 4.52 (s, 2H), 4.78 (d, J = 13.3 Hz, 1H), 5.15 (d, J = 13.3 Hz, 1H), 6.04 (dd, J = 11.2, 2.4 Hz, 1H), 6.40 (td, J = 8.3, 2.4 Hz, 1H), 6.67 (d, J = 2.4 Hz, 1H), 6.71 (d, J = 8.1 Hz, 1H), 6.82 (dd, J = 8.1, 2.4 Hz, 1H), 6.83 (d, J = 8.1 Hz, 1H), 6.88-6.92 (m, 1H), 7.24 (d, J = 8.0 Hz, 2H), 7.27 (d, J = 8.1 Hz, 1H), 7.37 (d, J = 8.0 Hz, 2H) |

| | |
|---|---|
| 7-[4-(4-Chlorobenzylsulfonyl-oxy)-2-methoxyphenyl]-8-(5-fluoro-2-methylphenoxymethyl)-1,3,3-trimethyl-3,4-dihydro-1H-quinoxalin-2-one (Compound No. 1-20) 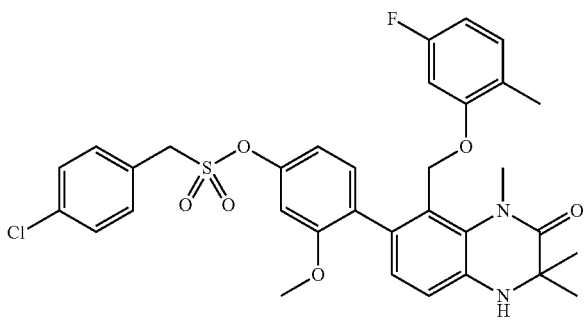 | $^1$H-NMR (500 MHz, CDCl$_3$) δ 0.98 (s, 3H), 1.27 (s, 3H), 2.01 (s, 3H), 3.45 (s, 3H), 3.74 (s, 1H), 3.77 (s, 3H), 4.51 (s, 2H), 4.77 (d, J = 13.3 Hz, 1H), 5.14 (d, J = 13.3 Hz, 1H), 6.04 (dd, J = 11.3, 2.4 Hz, 1H), 6.40 (td, J = 8.2, 2.4 Hz, 1H), 6.68 (d, J = 2.4 Hz, 1H), 6.72 (d, J = 8.1 Hz, 1H), 6.82 (dd, J = 8.3, 2.4 Hz, 1H), 6.84 (d, J = 8.1 Hz, 1H), 6.89-6.92 (m, 1H), 7.29 (d, J = 8.3 Hz, 1H), 7.42 (s, 4H) |
| 8-(5-Fluoro-2-methylphenoxy-methyl)-7-(4-isobutylsulfonyl-oxy-2-methoxyphenyl)-1,3,3-trimethyl-3,4-dihydro-1H-quinoxalin-2-one (Compound No. 1-21) 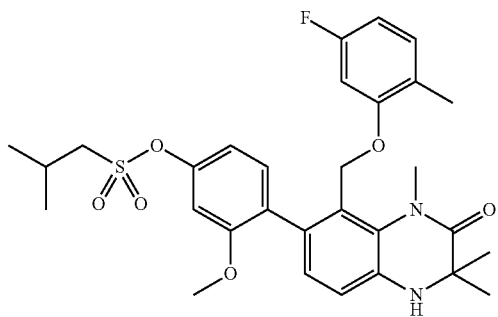 | $^1$H-NMR (400 MHz, CDCl$_3$) δ 0.97 (s, 3H), 1.19 (d, J = 6.6 Hz, 6H), 1.28 (s, 3H), 2.01 (s, 3H), 2.43-2.50 (m, 1H), 3.20 (d, J = 6.6 Hz, 2H), 3.46 (s, 3H), 3.75 (s, 1H), 3.84 (s, 3H), 4.80 (d, J = 13.4 Hz, 1H), 5.17 (d, J = 13.4 Hz, 1H), 6.05 (dd, J = 11.2, 2.4 Hz, 1H), 6.40 (td, J = 8.3, 2.4 Hz, 1H), 6.73 (d, J = 8.0 Hz, 1H), 6.86 (d, J = 8.0 Hz, 1H), 6.89-6.92 (m, 1H), 6.92 (d, J = 2.3 Hz, 1H), 6.94 (dd, J = 8.3, 2.3 Hz, 1H), 7.32 (d, J = 8.3 Hz, 1H) |
| 8-(5-Fluoro-2-methylphenoxy-methyl)-7-[2-methoxy-4-(3,3,3-trifluoropropylsulfonyloxy)-phenyl]-1,3,3-trimethyl-3,4-dihydro-1H-quinoxalin-2-one (Compound No. 1-22) 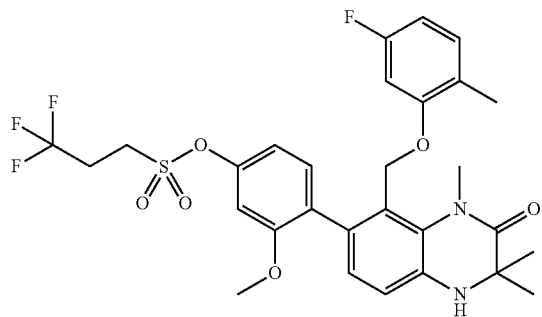 | $^1$H-NMR (400 MHz, CDCl$_3$) δ 1.00 (s, 3H), 1.28 (s, 3H), 2.01 (s, 3H), 2.79-2.90 (m, 2H), 3.46 (s, 3H), 3.50-3.54 (m, 2H), 3.76 (s, 1H), 3.84 (s, 3H), 4.79 (d, J = 13.4 Hz, 1H), 5.16 (d, J = 13.4 Hz, 1H), 6.05 (dd, J = 11.2, 2.5 Hz, 1H), 6.47 (td, J = 8.3, 2.5 Hz, 1H), 6.73 (d, J = 8.1 Hz, 1H), 6.86 (d, J = 8.1 Hz, 1H), 6.89 (d, J = 2.4 Hz, 1H), 6.89-6.93 (m, 1H), 6.93 (dd, J = 8.2, 2.4 Hz, 1H), 7.35 (d, J = 8.2 Hz, 1H) |

| Compound | NMR |
|---|---|
| 7-(4-Cyclopropylsulfonyloxy-2-methoxyphenyl)-8-(5-fluoro-2-methylphenoxymethyl)-1,3,3-trimethyl-3,4-dihydro-1H-quinoxalin-2-one (Compound No. 1-23)<br>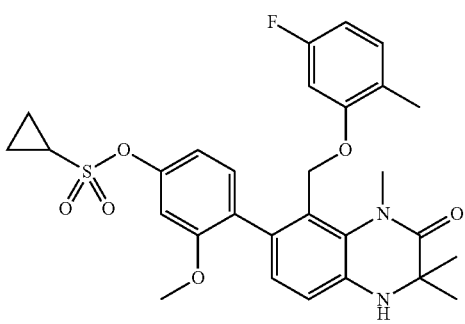 | $^1$H-NMR (400 MHz, CDCl$_3$) δ 0.99 (s, 3H), 1.10-1.13 (m, 2H), 1.28 (s, 3H), 1.28-1.32 (m, 2H), 2.02 (s, 3H), 2.60 (tt, J = 7.9, 4.7 Hz, 1H), 3.46 (s, 3H), 3.75 (s, 1H), 3.83 (s, 3H), 4.77 (d, J = 13.3 Hz, 1H), 5.15 (d, J = 13.3 Hz, 1H), 6.05 (dd, J = 11.2, 2.5 Hz, 1H), 6.40 (td, J = 8.3, 2.5 Hz, 1H), 6.73 (d, J = 8.0 Hz, 1H), 6.67 (d, J = 8.0 Hz, 1H), 6.89-6.93 (m, 1H), 6.94 (d, J = 2.4 Hz, 1H), 6.99 (dd, J = 8.3, 2.4 Hz, 1H), 7.32 (d, J = 8.3 Hz, 1H) |
| 8-(5-Fluoro-2-methylphenoxymethyl)-7-(2-methoxy-4-phenylsulfonylaminophenyl)-1,3,3-trimethyl-3,4-dihydro-1H-quinoxalin-2-one (Compound No. 1-24)<br>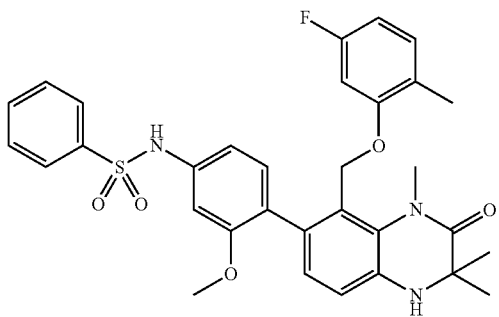 | $^1$H-NMR (500 MHz, CDCl$_3$) δ 0.95 (s, 3H), 1.29 (s, 3H), 2.00 (s, 3H), 3.43 (s, 3H), 3.71 (s, 1H), 3.75 (s, 3H), 4.70 (d, J = 13.3 Hz, 1H), 5.11 (d, J = 13.3 Hz, 1H), 5.97 (dd, J = 11.3, 2.4 Hz, 1H), 6.42 (td, J = 8.2, 2.4 Hz, 1H), 6.49 (s, 1H), 6.62 (dd, J = 8.0, 2.1 Hz, 1H), 6.70 (d, J = 8.1 Hz, 1H), 6.81 (d, J = 8.1 Hz, 1H), 6.81 (d, J = 2.1 Hz, 1H), 6.90-6.93 (m, 1H), 7.14 (d, J = 8.0 Hz, 1H), 7.40-7.54 (m, 3H), 7.78-7.80 (m, 2H) |
| 8-(5-Fluoro-2-methylphenoxymethyl)-7-(2-methoxy-4-methylsulfonylaminophenyl)-1,3,3-trimethyl-3,4-dihydro-1H-quinoxalin-2-one (Compound No. 1-25)<br>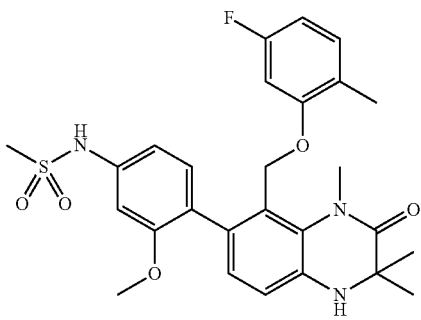 | $^1$H-NMR (500 MHz, CDCl$_3$) δ 0.97 (s, 3H), 1.29 (s, 3H), 2.01 (s, 3H), 3.04 (s, 3H), 3.47 (s, 3H), 3.73 (s, 1H), 3.83 (s, 3H), 4.79 (d, J = 13.3 Hz, 1H), 5.18 (d, J = 13.3 Hz, 1H), 6.05 (dd, J = 11.0, 2.4 Hz, 1H), 6.40 (td, J = 8.4, 2.4 Hz, 1H), 6.45 (s, 1H), 6.73 (d, J = 7.9 Hz, 1H), 6.82 (dd, J = 8.1, 2.1 Hz, 1H), 6.86 (d, J = 7.9 Hz, 1H), 6.89-6.92 (m, 1H), 6.93 (d, J = 2.1 Hz, 1H), 7.28 (d, J = 8.1 Hz, 1H) |

| | | |
|---|---|---|
| 8-(5-Fluoro-2-methylphenoxy-methyl)-7-[4-(2-fluorophenyl-sulfonyloxy)-2-methoxyphenyl]-1,3,3-trimethyl-3,4-dihydro-1H-quinoxalin-2-one (Compound No. 1-26) 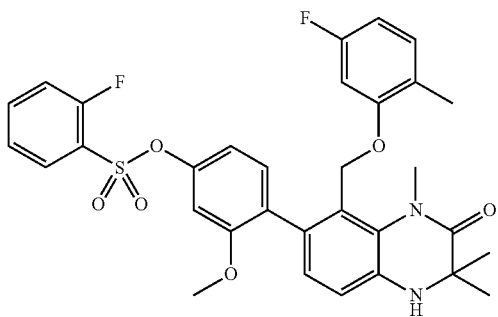 | $^1$H-NMR (500 MHz, CDCl$_3$) δ 0.99 (s, 3H), 1.28 (s, 3H), 1.99 (s, 3H), 3.43 (s, 3H), 3.74 (s, 3H), 4.68 (d, J = 13.1 Hz, 1H), 5.08 (d, J = 13.1 Hz, 1H), 5.98 (dd, J = 11.0, 2.4 Hz, 1H), 6.43 (td, J = 8.3, 2.4 Hz, 1H), 6.70 (d, J = 7.9 Hz, 1H), 6.75 (dd, J = 8.3, 2.3 Hz, 1H), 6.79 (d, J = 2.3 Hz, 1H), 6.82 (d, J = 7.9 Hz, 1H), 6.91-6.94 (m, 1H), 7.21 (d, J = 8.3 Hz, 1H), 7.21-7.24 (m, 2H), 7.63-7.68 (m, 1H), 7.79-7.81 (m, 1H) | |
| 7-[4-(2-Chlorobenzylsulfonyl-oxy)-2-methoxyphenyl]-8-(5-fluoro-2-methylphenoxymethyl)-1,3,3-trimethyl-3,4-dihydro-1H-quinoxalin-2-one (Compound No. 1-27) 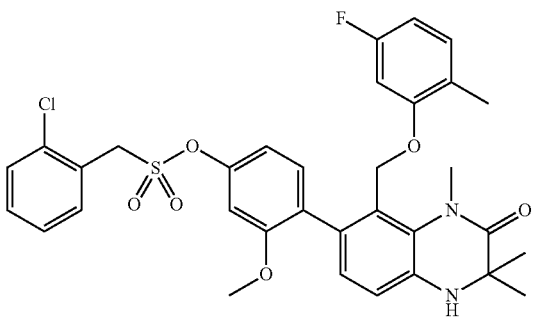 | $^1$H-NMR (500 MHz, CDCl$_3$) δ 0.96 (s, 3H), 1.26 (s, 3H), 2.01 (s, 3H), 3.45 (s, 3H), 3.73 (s, 3H), 3.77 (s, 3H), 4.77 (d, J = 13.4 Hz, 1H), 4.82 (s, 2H), 5.15 (d, J = 13.4 Hz, 1H), 6.03 (dd, J = 11.3, 2.4 Hz, 1H), 6.39 (td, J = 8.2, 2.4 Hz, 1H), 6.71 (d, J = 8.1 Hz, 1H), 6.76 (d, J = 2.3 Hz, 1H), 6.83 (d, J = 8.1 Hz, 1H), 6.84 (dd, J = 7.6, 2.3 Hz, 1H), 6.89-6.92 (m, 1H), 7.29 (d, J = 7.6 Hz, 1H), 7.33-7.38 (m, 2H), 7.48 (dd, J = 7.5, 1.7 Hz, 1H), 7.63 (dd, J = 7.2, 2.3 Hz, 1H) | |
| 8-(5-Fluoro-2-methylphenoxy-methyl)-7-[2-methoxy-4-(2-methylbenzylsulfonyloxy)phenyl]-1,3,3-trimethyl-3,4-dihydro-1H-quinoxalin-2-one (Compound No. 1-28) 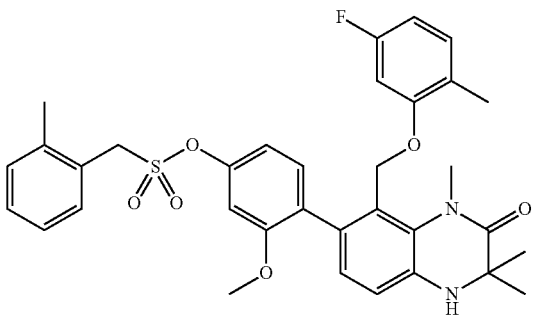 | $^1$H-NMR (500 MHz, CDCl$_3$) δ 0.96 (s, 3H), 1.26 (s, 3H), 2.00 (s, 3H), 2.47 (s, 3H), 3.44 (s, 3H), 3.73 (s, 4H), 4.64 (s, 2H), 4.77 (d, J = 13.4 Hz, 1H), 5.14 (d, J = 13.4 Hz, 1H), 6.03 (dd, J = 11.0, 2.4 Hz, 1H), 6.40 (td, J = 8.2, 2.4 Hz, 1H), 6.64 (d, J = 2.1 Hz, 1H), 6.71 (d, J = 7.9 Hz, 1H), 6.79 (dd, J = 8.2, 2.1 Hz, 1H), 6.83 (d, J = 7.9 Hz, 1H), 6.89-6.92 (m, 1H), 7.26-7.34 (m, 4H), 7.45 (d, J = 7.6 Hz, 1H) | |

| | |
|---|---|
| 8-(4-Cyclopentylsulfonyloxy-2-methoxyphenyl)-8-(5-fluoro-2-methylphenoxymethyl)-1,3,3-trimethyl-3,4-dihydro-1H-quinoxalin-2-one (Compound No. 1-29) 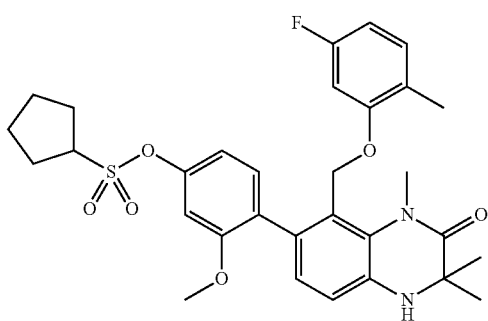 | $^1$H-NMR (400 MHz, CDCl$_3$) δ 0.97 (s, 3H), 1.27 (s, 3H), 1.69-1.76 (m, 2H), 1.88-1.94 (m, H), 2.01 (s, 3H), 2.11-2.20 (m, 2H), 2.24-2.29 (m, 2H), 3.46 (s, 3H), 3.68-3.76 (m, 1H), 3.74 (s, 1H), 3.83 (s, 3H), 4.80 (d, J = 13.4 Hz, 1H), 5.17 (d, J = 13.4 Hz, 1H), 6.05 (dd, J = 11.2, 2.5 Hz, 1H), 6.40 (td, J = 8.4, 2.5 Hz, 1H), 6.72 (d, J = 8.1 Hz, 1H), 6.86 (d, J = 8.1 Hz, 1H), 6.89-6.93 (m, 1H), 6.93 (d, J = 2.2 Hz, 1H), 6.94 (dd, J = 8.1, 2.2 Hz, 1H), 7.31 (d, J = 8.1 Hz, 1H) |
| 7-(4-Cyclohexylsulfonyloxy-2-methoxyphenyl)-8-(5-fluoro-2-methylphenoxymethyl)-1,3,3-trimethyl-3,4-dihydro-1H-quinoxalin-2-one (Compound No. 1-30) 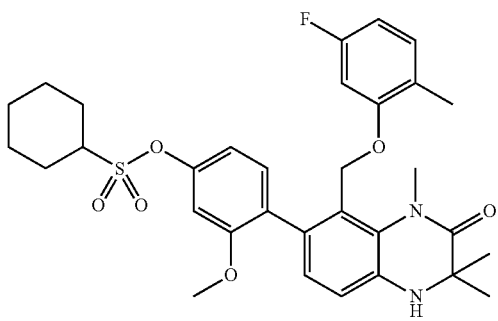 | $^1$H-NMR (500 MHz, CDCl$_3$) δ 0.97 (s, 3H), 1.27 (s, 3H), 1.29-1.39 (m, 3H), 1.72-1.80 (m, 3H), 1.96-1.99 (m, 2H), 2.01 (s, 3H), 2.37-2.39 (m, 2H), 3.25 (tt, J = 12.1, 3.5 Hz, 1H), 3.46 (s, 3H), 3.74 (s, 1H), 3.83 (s, 3H), 4.81 (d, J = 13.4 Hz, 1H), 5.17 (d, J = 13.4 Hz, 1H), 6.05 (dd, J = 11.2, 2.4 Hz, 1H), 6.40 (td, J = 8.2, 2.4 Hz, 1H), 6.72 (d, J = 7.9 Hz, 1H), 6.86 (d, J = 7.9 Hz, 1H), 6.89-6.92 (m, 1H), 6.91 (d, J = 2.4 Hz, 1H), 6.93 (dd, J = 8.1, 2.4 Hz, 1H), 7.31 (d, J = 8.1 Hz, 1H) |
| 8-(5-Fluoro-2-methylphenoxymethyl)-7-[2-methoxy-4-(3-methylbenzylsulfonyloxy)phenyl]-1,3,3-trimethyl-3,4-dihydro-1H-quinoxalin-2-one (Compound No. 1-31) 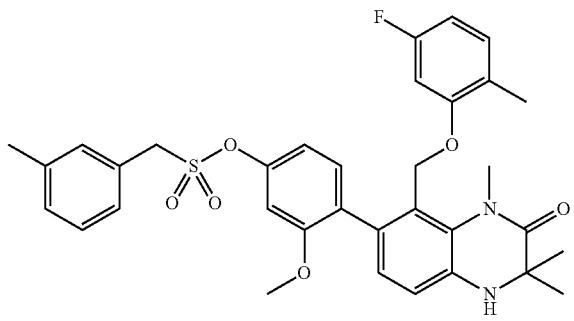 | $^1$H-NMR (400 MHz, CDCl$_3$) δ 0.96 (s, 3H), 1.26 (s, 3H), 2.01 (s, 3H), 2.38 (s, 3H), 3.45 (s, 3H), 3.74 (s, 1H), 3.75 (s, 3H), 4.52 (s, 2H), 4.78 (d, J = 13.6 Hz, 1H), 5.15 (d, J = 13.6 Hz, 1H), 6.04 (dd, J = 11.2, 2.4 Hz, 1H), 6.39 (td, J = 8.3, 2.4 Hz, 1H), 6.69 (d, J = 2.2 Hz, 1H), 6.71 (d, J = 8.0 Hz, 1H), 6.82 (dd, J = 8.3, 2.2 Hz, 1H), 6.84 (d, J = 8.0 Hz, 1H), 6.88-6.92 (m, 1H), 7.22-7.34 (m, 4H), 7.28 (d, J = 8.3 Hz, 1H) |

| | |
|---|---|
| 7-(4-Cyclopropylsulfonyloxy-2-methoxyphenyl)-8-(5-methyl-thiophen-2-ylcarbonyloxymeth-yl)-1,3,3-trimethyl-3,4-dihydro-1H-quinoxalin-2-one (Compound No. 1-32) 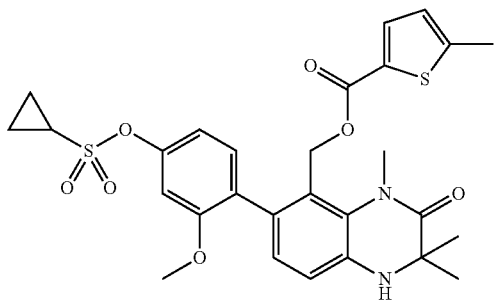 | $^1$H-NMR (400 MHz, CDCl$_3$) δ 1.09-1.15 (m, 2H), 1.23 (s, 3H), 1.28-1.33 (m, 2H), 1.41 (s, 3H), 2.48 (s, 3H), 2.60 (tt, J = 7.9, 4.8 Hz, 1H), 3.46 (s, 3H), 3.75 (s, 3H), 3.81 (s, 1H), 5.07 (d, J = 13.2 Hz, 1H), 5.23 (d, J = 13.2 Hz, 1H), 6.70 (d, J = 3.6 Hz, 1H), 6.76 (d, J = 8.1 Hz, 1H), 6.84 (d, J = 8.1 Hz, 1H), 6.89 (d, J = 2.3 Hz, 1H), 6.91 (dd, J = 7.7, 2.3 Hz, 1H), 7.27 (d, J = 7.7 Hz, 1H), 7.43 (d, J = 3.6 Hz, 1H) |
| 7-[2-Methoxy-4-(3,3,3-trifluoro-propylsulfonyloxy)phenyl]-8-(5-methylthiophen-2-yl-carbonyloxymethyl)-1,3,3-tri-methyl-3,4-dihydro-1H-quinoxalin-2-one (Compound No. 1-33) 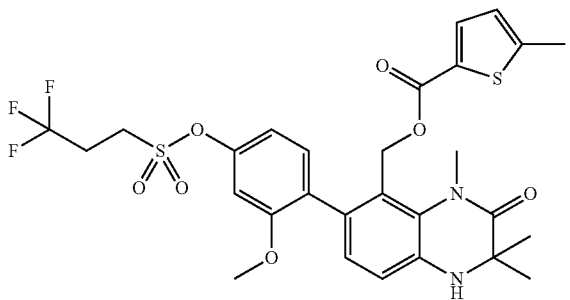 | $^1$H-NMR (400 MHz, CDCl$_3$) δ 1.23 (s, 3H), 1.41 (s, 3H), 2.48 (s, 3H), 2.77-2.89 (m, 2H), 3.46 (s, 3H), 3.49-3.53 (m, 2H), 3.76 (s, 3H), 3.82 (s, 1H), 5.07 (d, J = 13.2 Hz, 1H), 5.24 (d, J = 13.2 Hz, 1H), 6.70 (d, J = 3.7 Hz, 1H), 6.76 (d, J = 8.1 Hz, 1H), 6.83 (d, J = 2.4 Hz, 1H), 6.84 (d, J = 8.1 Hz, 1H), 6.85 (dd, J = 8.3, 2.4 Hz, 1H), 7.30 (d, J = 8.3 Hz, 1H), 7.43 (d, J = 3.7 Hz, 1H) |
| 7-(4-Isobutylsulfonyloxy-2-methoxyphenyl)-8-(5-methylthio-phen-2-ylcarbonyloxymethyl)-1,3,3-trimethyl-3,4-dihydro-1H-quinoxalin-2-one (Compound No. 1-34) 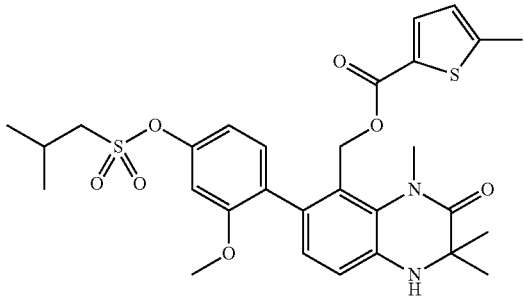 | $^1$H-NMR (500 MHz, CDCl$_3$) δ 1.18 (d, J = 6.8 Hz, 3H), 1.19 (d, J = 6.8 Hz, 3H), 1.22 (s, 3H), 1.41 (s, 3H), 2.41-2.51 (m, 1H), 2.48 (s, 3H), 3.18 (d, J = 6.7 Hz, 2H), 3.46 (s, 3H), 3.75 (s, 3H), 3.81 (s, 1H), 5.08 (d, J = 13.1 Hz, 1H), 3.23 (d, J = 13.1 Hz, 1H), 6.70 (d, J = 3.7 Hz, 1H), 6.76 (d, J = 7.9 Hz, 1H), 6.84 (d, J = 7.9 Hz, 1H), 6.86 (s, 1H), 6.87 (d, J = 7.9 Hz, 1H), 7.28 (d, J = 7.9 Hz, 1H), 7.43 (d, J = 3.7 Hz, 1H) |

| Compound | NMR |
|---|---|
| 7-(2-Methoxy-4-propylsulfonyl-oxyphenyl)-8-(5-methylthio-phen-2-ylcarbonyloxymethyl)-1,3,3-trimethyl-3,4-dihydro-1H-quinoxalin-2-one (Compound No. 1-35) 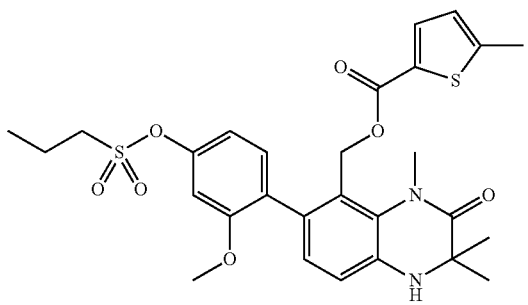 | $^1$H-NMR (400 MHz, CDCl$_3$) δ 1.14 (t, J = 7.6 Hz, 3H), 1.22 (s, 3H), 1.41 (s, 3H), 1.99-2.08 (m, 2H), 2.48 (s, 3H), 3.23-3.27 (m, 2H), 3.46 (s, 3H), 3.76 (s, 3H), 3.81 (s, 1H), 5.08 (d, J = 13.2 Hz, 1H), 5.25 (d, J = 13.2 Hz, 1H), 6.70 (d, J = 3.8 Hz, 1H), 6.76 (d, J = 8.1 Hz, 1H), 6.84 (d, J = 8.1 Hz, 1H), 6.86 (d, J = 1.7 Hz, 1H), 6.87 (dd, J = 7.3, 1.7 Hz, 1H), 7.28 (d, J = 7.3 Hz, 1H), 7.43 (d, J = 3.8 Hz, 1H) |
| 7-(4-Isopropylsulfonyloxy-2-methoxyphenyl)-8-(5-methyl-thiophen-2-ylcarbonyloxymethyl)-1,3,3-trimethyl-3,4-dihydro-1H-quinoxalin-2-one (Compound No. 1-36) 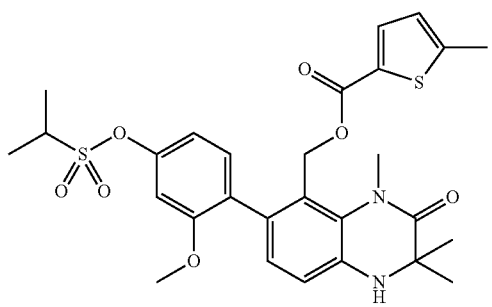 | $^1$H-NMR (500 MHz, CDCl$_3$) δ 1.21 (s, 3H), 1.41 (s, 3H), 1.56 (d, J = 7.3 Hz, 3H), 1.57 (d, J = 7.3 Hz, 3H), 2.48 (s, 3H), 3.45 (s, 3H), 3.47-3.52 (m, 1H), 3.76 (s, 3H), 3.80 (s, 1H), 5.08 (d, J = 13.1 Hz, 1H), 5.25 (d, J = 13.1 Hz, 1H), 6.70 (d, J = 3.9 Hz, 1H), 6.76 (d, J = 7.9 Hz, 1H), 6.84 (d, J = 7.9 Hz, 1H), 6.86 (d, J = 2.4 Hz, 1H), 6.87 (dd, J = 9.1, 2.4 Hz, 1H), 7.27 (d, J = 9.1 Hz, 1H), 7.43 (d, J = 3.9 Hz, 1H) |
| 7-(4-Cyclopentylsulfonyloxy-2-methoxyphenyl)-8-(5-methyl-thiophen-2-ylcarbonyloxymeth-yl)-1,3,3-trimethyl-3,4-dihydro-1H-quinoxalin-2-one (Compound No. 1-37) 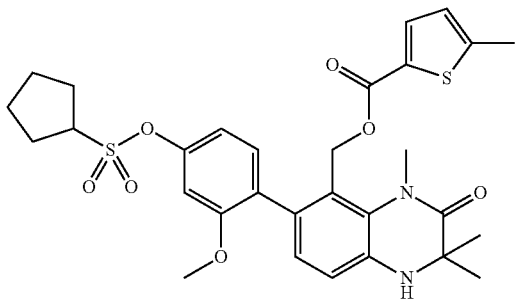 | $^1$H-NMR (400 MHz, CDCl$_3$) δ 1.22 (s, 3H), 1.41 (s, 3H), 1.68-1.72 (m, 2H), 1.88-1.93 (m, 2H), 2.12-2.15 (m, 2H), 2.21-2.30 (m, 2H), 2.48 (s, 3H), 3.45 (s, 3H), 3.67-3.74 (m, 1H), 3.76 (s, 3H), 3.81 (s, 1H), 5.08 (d, J = 13.3 Hz, 1H), 5.25 (d, J = 13.3 Hz, 1H), 6.70 (d, J = 3.7 Hz, 1H), 6.76 (d, J = 8.0 Hz, 1H), 6.84 (d, J = 8.0 Hz, 1H), 6.86 (d, J = 2.1 Hz, 1H), 6.87 (dd, J = 7.8, 2.1 Hz, 1H), 7.27 (d, J = 7.8 Hz, 1H), 7.43 (d, J = 3.7 Hz, 1H) |

| | |
|---|---|
| 7-(2-Methoxy-4-methylsulfonyl-oxyphenyl)-8-(2-methoxy-5-nitrophenoxymethyl)-1,3,3-tri-methyl-3,4-dihydro-1H-quinoxalin-2-one (Compound No. 1-38)<br>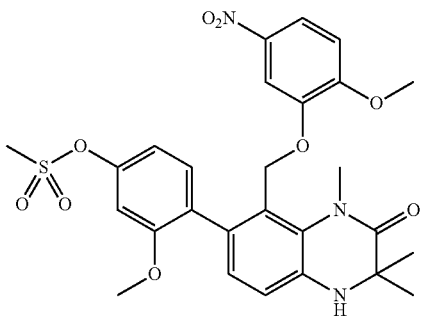 | $^1$H-NMR (500 MHz, CDCl$_3$) δ 0.76 (s, 3H), 1.33 (s, 3H), 3.20 (s, 3H), 3.53 (s, 3H), 3.71 (s, 1H), 3.84 (s, 3H), 3.86 (s, 3H), 4.92 (d, J = 13.7 Hz, 1H), 5.41 (d, J = 13.7 Hz, 1H), 6.71 (d, J = 7.9 Hz, 1H), 6.76 (d, J = 8.9 Hz, 1H), 6.85 (d, J = 7.9 Hz, 1H), 6.92 (d, J = 2.3 Hz, 1H), 7.00 (dd, J = 8.2, 2.3 Hz, 1H), 7.11 (d, J = 2.4 Hz, 1H), 7.49 (d, J = 8.2 Hz, 1H), 7.74 (dd, J = 8.9, 2.4 Hz, 1H) |
| 8-(2-Methoxy-5-nitrophenoxy-methyl)-7-[2-methoxy-4-(3,3,3-trifluoropropylsulfonyloxy)-phenyl]-1,3,3-trimethyl-3,4-dihydro-1H-quinoxalin-2-one (Compound No. 1-39)<br>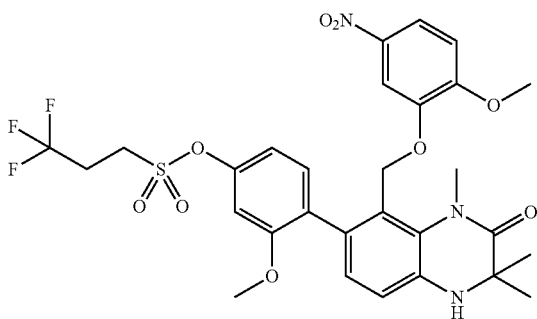 | $^1$H-NMR (500 MHz, CDCl$_3$) δ 0.79 (s, 3H), 1.33 (s, 3H), 2.80-2.89 (m, 2H), 3.51-3.55 (m, 2H), 3.53 (s, 3H), 3.73 (s, 1H), 3.84 (s, 3H), 3.86 (s, 3H), 4.90 (d, J = 13.7 Hz, 1H), 5.39 (d, J =13.7 Hz, 1H), 6.72 (d, J = 8.1 Hz, 1H), 6.76 (d, J = 9.1 Hz, 1H), 6.85 (d, J = 8.1 Hz, 1H), 6.88 (d, J = 2.3 Hz, 1H), 6.97 (dd, J = 8.2, 2.3 Hz, 1H), 7.12 (d, J = 2.5 Hz, 1H), 7.51 (d, J = 8.2 Hz, 1H), 7.75 (dd, J = 9.1, 2.5 Hz, 1H) |
| 7-(4-Isobutylsulfonyloxy-2-methoxyphenyl)-8-(2-methoxy-5-nitrophenoxymethyl)-1,3,3-trimethyl-3,4-dihydro-1H-quinoxalin-2-one (Compound No. 1-40)<br>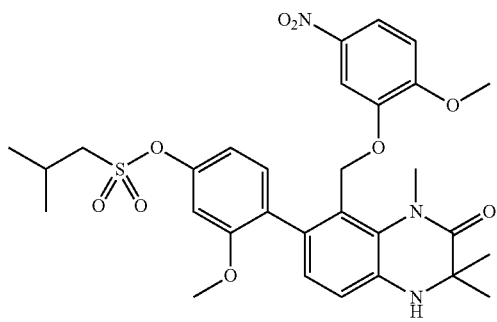 | $^1$H-NMR (400 MHz, CDCl$_3$) δ 0.74 (s, 3H), 1.19 (d, J = 6.8 Hz, 6H), 1.33 (s, 3H), 2.43-2.50 (m, 1H), 3.21 (d, J = 6.8 Hz, 2H), 3.53 (s, 3H), 3.71 (br s, 1H), 3.84 (s, 3H), 3.85 (s, 3H), 4.93 (d, J = 13.7 Hz, 1H), 5.42 (d, J = 13.7 Hz, 1H), 6.71 (d, J = 7.9 Hz, 1H), 6.75 (d, J = 9.0 Hz, 1H), 6.86 (d, J = 7.9 Hz, 1H), 6.91 (d, J = 2.3 Hz, 1H), 6.98 (dd, J = 8.3, 2.3 Hz, 1H), 7.11 (d, J = 2.6 Hz, 1H), 7.48 (d, J = 8.3 Hz, 1H), 7.74 (dd, J = 9.0, 2.6 Hz, 1H) |

| | |
|---|---|
| 7-(4-Cyclopentylsulfonyloxy-2-methoxyphenyl)-8-(2-methoxy-5-nitrophenoxymethyl)-1,3,3-trimethyl-3,4-dihydro-1H-quinoxalin-2-one (Compound No. 1-41)<br>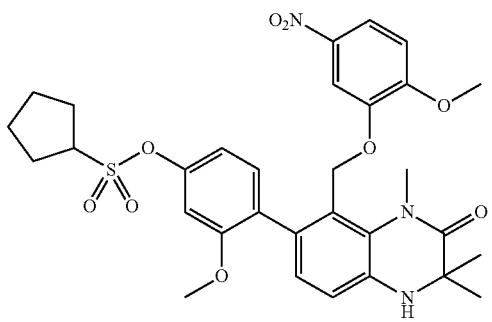 | $^1$H-NMR (400 MHz, CDCl$_3$) δ 0.74 (s, 3H), 1.33 (s, 3H), 1.69-1.74 (m, 2H), 1.88-1.92 (m, 2H), 2.14-2.19 (m, 2H), 2.25-2.30 (m, 2H), 3.53 (s, 3H), 3.71 (br s, 1H), 3.73-3.77 (m, 1H), 3.84 (s, 3H), 3.86 (s, 3H), 4.93 (d, J = 13.8 Hz, 1H), 5.42 (d, J = 13.8 Hz, 1H), 6.71 (d, J = 8.1 Hz, 1H), 6.75 (d, J = 9.0 Hz, 1H), 6.85 (d, J = 8.1 Hz, 1H), 6.92 (d, J = 2.3 Hz, 1H), 6.98 (dd, J = 8.2, 2.3 Hz, 1H), 7.11 (d, J = 2.6 Hz, 1H), 7.47 (d, J = 8.2 Hz, 1H), 7.74 (dd, J = 9.0, 2.6 Hz, 1H) |
| 7-(4-Isopropylsulfonyloxy-2-methoxyphenyl)-8-(2-methoxy-5-nitrophenoxymethyl)-1,3,3-trimethyl-3,4-dihydro-1H-quinoxalin-2-one (Compound No. 1-42)<br>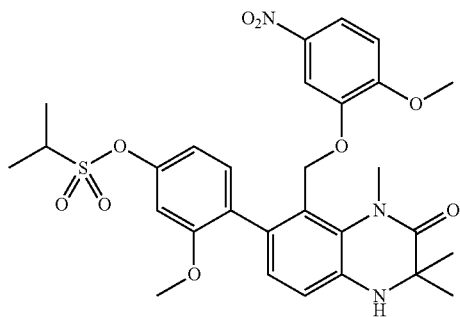 | $^1$H-NMR (500 MHz, CDCl$_3$) δ 0.75 (s, 3H), 1.33 (s, 3H), 1.59 (d, J = 7.0 Hz, 6H), 3.50-3.56 (m, 1H), 3.53 (s, 3H), 3.70 (br s, 1H), 3.84 (s, 3H), 3.85 (s, 3H), 4.93 (d, J = 13.7 Hz, 1H), 5.41 (d, J = 13.7 Hz, 1H), 6.71 (d, J = 8.1 Hz, 1H), 6.75 (d, J = 8.9 Hz, 1H), 6.85 (d, J = 8.1 Hz, 1H), 6.91 (d, J = 2.1 Hz, 1H), 6.98 (dd, J = 8.2, 2.1 Hz, 1H), 7.12 (d, J = 2.6 Hz, 1H), 7.48 (d, J = 8.2 Hz, 1H), 7.74 (dd, J = 8.9, 2.6 Hz, 1H) |
| 7-(4-Cyclopropylsulfonyloxy-2-methoxyphenyl)-8-(2-methoxy-5-nitrophenoxymethyl)-1,3,3-trimethyl-3,4-dihydro-1H-quinoxalin-2-one (Compound No. 1-43)<br>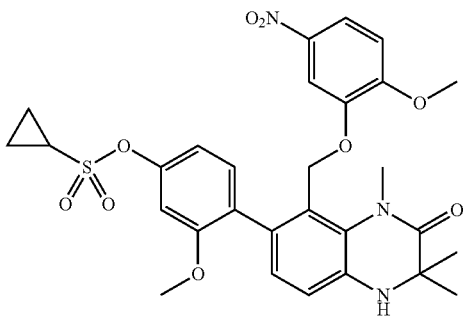 | $^1$H-NMR (400 MHz, CDCl$_3$) δ 0.75 (s, 3H), 1.14-1.18 (m, 2H), 1.29-1.32 (m, 2H), 1.34 (s, 3H), 2.61-2.68 (m, 1H), 3.53 (s, 3H), 3.71 (br s, 1H), 3.84 (s, 3H), 3.86 (s, 3H), 4.91 (d, J = 13.8 Hz, 1H), 5.41 (d, J = 13.8 Hz, 1H), 6.71 (d, J = 7.9 Hz, 1H), 6.76 (d, J = 8.9 Hz, 1H), 6.86 (d, J = 7.9 Hz, 1H), 6.93 (d, J = 2.2 Hz, 1H), 7.04 (dd, J = 8.3, 2.2 Hz, 1H), 7.11 (d, J = 2.6 Hz, 1H), 7.48 (d, J = 8.3 Hz, 1H), 7.74 (dd, J = 8.9, 2.6 Hz, 1H) |

| | |
|---|---|
| 8-(2-Methoxy-5-nitrophenoxymethyl-7-(2-methoxy-4-propylsulfonyloxyphenyl)-1,3,3-trimethyl-3,4-dihydro-1H-quinoxalin-2-one (Compound No. 1-44)<br />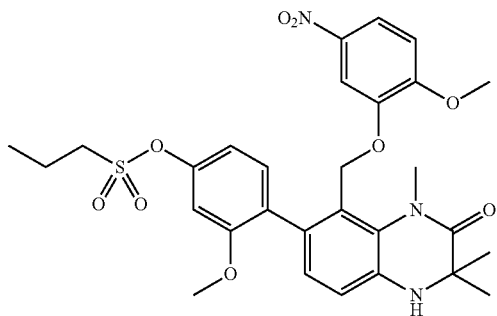 | $^1$H-NMR (400 MHz, DMSO-d$_6$) δ 0.73 (s, 3H), 1.02 (t, J = 7.5 Hz, 3H), 1.16 (s, 3H), 1.84 (sextet, J = 7.5 Hz, 2H), 3.37 (s, 3H), 3.50 (t, J = 7.5 Hz, 2H), 3.79 (s, 3H), 3.79 (s, 3H), 4.82 (d, J = 13.7 Hz, 1H), 5.39 (d, J = 13.7 Hz, 1H), 6.15 (s, 1H), 6.80 (s, 2H), 6.97 (dd, J = 8.2, 2.3 Hz, 1H), 7.00 (d, J = 2.3 Hz, 1H), 7.04 (d, J = 9.0 Hz, 1H), 7.13 (d, J = 2.7 Hz, 1H), 7.39 (d, J = 8.2 Hz, 1H), 7.76 (dd, J = 9.0, 2.7 Hz, 1H) |
| 7-(4-Cyclopropylsulfonyloxy-2-methoxyphenyl)-8-(2-methyl-5-nitrophenoxymethyl)-1,3,3-trimethyl-3,4-dihydro-1H-quinoxalin-2-one (Compound No. 1-45)<br />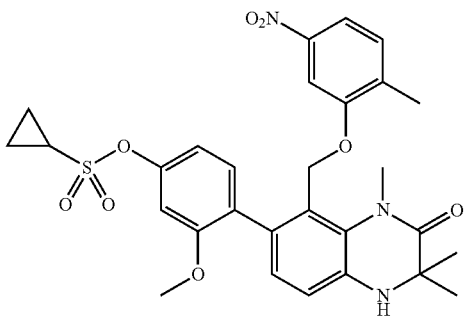 | $^1$H-NMR (500 MHz, CDCl$_3$) δ 0.65 (s, 3H), 1.12-1.33 (m, 4H), 1.37 (s, 3H), 2.17 (s, 3H), 2.63-2.68 (m, 1H), 3.52 (s, 3H), 3.72 (s, 1H), 3.86 (s, 3H), 4.93 (d, J =14.1 Hz, 1H), 5.44 (d, J = 14.1 Hz, 1H), 6.72 (d, J = 8.2 Hz, 1H), 6.89 (d, J = 8.2 Hz, 1H), 6.96 (d, J = 2.1 Hz, 1H), 7.00 (d, J = 2.2 Hz, 1H), 7.08 (dd, J = 8.2, 2.1 Hz, 1H), 7.11 (d, J = 8.2 H.z, 1H), 7.54 (d, J = 8.2 Hz, 1H), 7.59 (dd, J = 8.2, 2.2 Hz, 1H) |
| 7-[2-Methoxy-4-(3,3,3-trifluoropropylsulfonyloxy)phenyl]-8-(2-methyl-5-nitrophenoxymethyl)-1,3,3-trimethyl-3,4-dihydro-1H-quinoxalin-2-one (Compound No. 1-46)<br />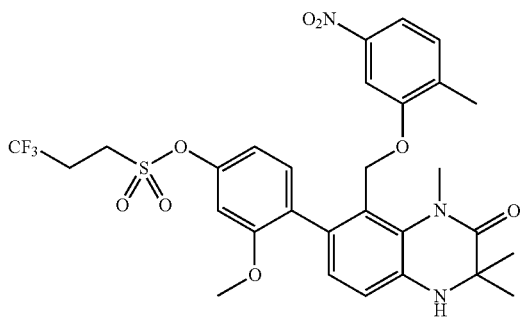 | $^1$H-NMR (400 MHz, CDCl$_3$) δ 0.64 (s, 3H), 1.37 (s, 3H), 2.17 (s, 3H), 2.79-2.91 (m, 2H), 3.52 (s, 3H), 3.52-3.56 (m, 2H), 3.74 (s, 1H), 3.86 (s, 3H), 4.92 (d, J = 13.9 Hz, 1H), 5.44 (d, J = 13.9 Hz, 1H), 6.72 (d, J = 8.1 Hz, 1H), 6.89 (d, J = 8.1 Hz, 1H), 6.91 (d, J = 2.2 Hz, 1H), 7.00 (d, J = 2.2 Hz, 1H), 7.02 (dd, J = 8.3, 2.2 Hz, 1H), 7.11 (d, J = 8.3 Hz, 1H), 7.57 (d, J = 8.1 Hz, 1H), 7.59 (dd, J = 8.1, 2.2 Hz, 1H) |

| | |
|---|---|
| 7-(4-Isobutylsulfonyloxy-2-methoxyphenyl)-8-(2-methyl-5-nitrophenoxymethyl)-1,3,3-trimethyl-3,4-dihydro-1H-quinoxalin-2-one (Compound No. 1-47)<br>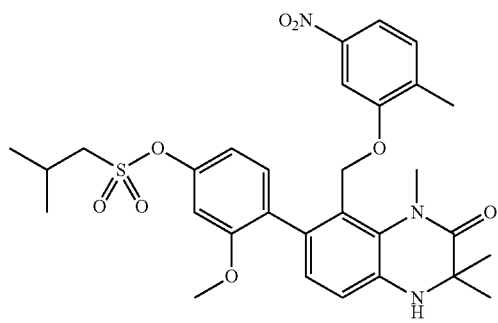 | $^1$H-NMR (500 MHz, CDCl$_3$) δ 0.63 (s, 3H), 1.19 (d, J = 6.7 Hz, 3H), 1.20 (d, J = 6.7 Hz, 3H), 1.37 (s, 3H), 2.17 (s, 3H), 2.43-2.51 (m, 1H), 3.22 (d, J = 6.7 Hz, 2H), 3.52 (s, 3H), 3.72 (s, 1H), 3.86 (s, 3H), 4.94 (d, J = 14.1 Hz, 1H), 5.45 (d, J = 14.1 Hz, 1H), 6.71 (d, J = 7.9 Hz, 1H), 6.89 (d, J = 7.9 Hz, 1H), 6.94 (d, J = 2.3 Hz, 1H), 7.00 (d, J = 2.1 Hz, 1H), 7.02 (dd, J = 8.2, 2.3 Hz, 1H), 7.11 (d, J = 8.2 Hz, 1H), 7.55 (d, J = 8.2 Hz, 1H), 7.58 (dd, J = 8.2, 2.1 Hz, 1H) |
| 7-(4-Isopropylsulfonyloxy-2-methoxyphenyl)-8-(2-methyl-5-nitrophenoxymethyl)-1,3,3-trimethyl-3,4-dihydro-1H-quinoxalin-2-one (Compound No. 1-48)<br>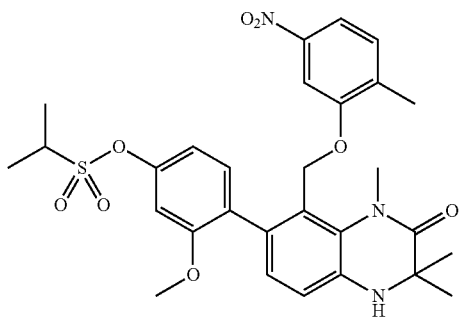 | $^1$H-NMR (500 MHz, CDCl$_3$) δ 0.64 (s, 3H), 1.36 (s, 3H), 1.58 (d, J = 6.9 Hz, 3H), 1.60 (d, J = 6.9 Hz, 3H), 2.17 (s, 3H), 3.48-3.56 (m, 1H), 3.52 (s, 3H), 3.71 (s, 1H), 3.86 (s, 3H), 4.94 (d, J = 14.1 Hz, 1H), 5.44 (d, J = 14.1 Hz, 1H), 6.71 (d, J = 8.1 Hz, 1H), 6.89 (d, J = 8.1 Hz, 1H), 6.94 (d, J = 2.2 Hz, 1H), 7.01 (d, J = 2.1 Hz, 1H), 7.02 (dd, J = 8.5, 2.2 Hz, 1H), 7.11 (d, J = 8.5 Hz, 1H), 7.55 (d, J = 8.2 Hz, 1H), 7.58 (dd, J = 8.2, 2.1 Hz, 1H) |
| 7-(2-Methoxy-4-methylsulfonyl-oxyphenyl)-8-(2-methyl-5-nitrophenoxymethyl)-1,3,3-trimethyl-3,4-dihydro-1H-quinoxalin-2-one (Compound No. 1-49)<br>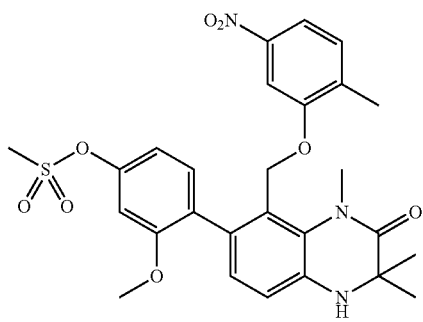 | $^1$H-NMR (400 MHz, CDCl$_3$) δ 0.64 (s, 3H), 1.37 (s, 3H), 2.17 (s, 3H), 3.21 (s, 3H), 3.51 (s, 3H), 3.73 (s, 1H), 3.86 (s, 3H), 4.94 (d, J = 14.2 Hz, 1H), 5.45 (d, J = 14.2 Hz, 1H), 6.72 (d, J = 8.1 Hz, 1H), 6.89 (d, J = 8.1 Hz, 1H), 6.95 (d, J = 2.3 Hz, 1H), 7.00 (d, J = 2.1 Hz, 1H), 7.05 (dd, J = 8.2, 2.3 Hz, 1H), 7.11 (d, J = 8.2 Hz, 1H), 7.56 (d, J = 8.3 Hz, 1H), 7.59 (dd, J = 8.3, 2.1 Hz, 1H) |

| | |
|---|---|
| 7-(4-Cyclopentylsulfonyloxy-2-methoxyphenyl)-8-(2-methyl-5-nitrophenoxymethyl)-1,3,3-trimethyl-3,4-dihydro-1H-quinoxalin-2-one (Compound No. 1-50)<br/>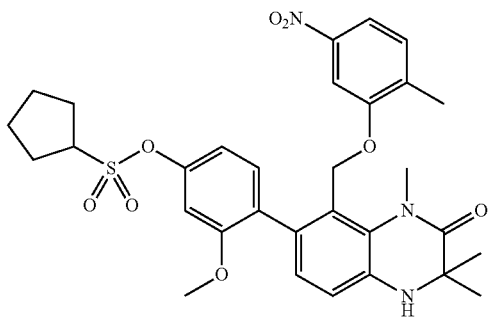 | $^1$H-NMR (500 MHz, CDCl$_3$) δ 0.64 (s, 3H), 1.36 (s, 3H), 1.68-1.74 (m, 2H), 1.88-1.94 (m, 2H), 2.14-2.21 (m, 2H), 2.17 (s, 3H), 2.24-2.32 (m, 2H), 3.52 (s, 3H), 3.71 (s, 1H), 3.73-3.79 (m, 1H), 3.86 (s, 3H), 4.94 (d, J = 14.1 Hz, 1H), 5.44 (d, J = 14.1 Hz, 1H), 6.71 (d, J = 7.9 Hz, 1H), 6.89 (d, J = 7.9 Hz, 1H), 6.94 (d, J = 2.3 Hz, 1H), 7.00 (d, J = 2.2 Hz, 1H), 7.02 (dd, J = 8.2, 2.3 Hz, 1H), 7.11 (d, J = 8.2 Hz, 1H), 7.54 (d, J = 8.2 Hz, 1H), 7.58 (dd, J = 8.2, 2.2 Hz, 1H) |
| 7-(2-Methoxy-4-propylsulfonyloxyphenyl)-8-(2-methoxy-5-nitrophenoxymethyl)-1,3,3-trimethyl-3,4-dihydro-1H-quinoxalin-2-one (Compound No. 1-51)<br/>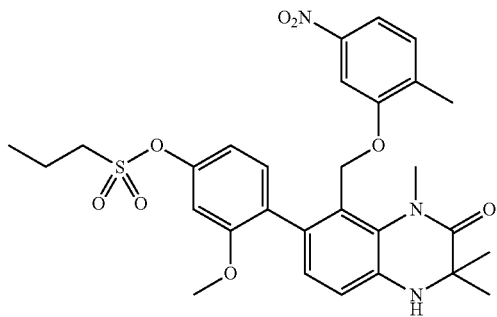 | $^1$H-NMR (400 MHz, CDCl$_3$) δ 0.63 (s, 3H), 1.15 (t, J = 7.5 Hz, 3H), 1.37 (s, 3H), 2.01-2.11 (m, 2H), 2.17 (s, 3H), 3.27-3.31 (m, 2H), 3.52 (s, 3H), 3.72 (s, 1H), 3.86 (s, 3H), 4.94 (d, J = 14.2 Hz, 1H), 5.45 (d, J = 14.2 Hz, 1H), 6.72 (d, J = 8.0 Hz, 1H), 6.89 (d, J = 8.0 Hz, 1H), 6.94 (d, J = 2.2 Hz, 1H), 7.00 (d, J = 2.2 Hz, 1H), 7.02 (dd, J = 8.3, 2.2 Hz, 1H), 7.11 (d, J = 8.3 Hz, 1H), 7.55 (d, J = 8.3 Hz, 1H), 7.58 (dd, J = 8.3, 2.2 Hz, 1H) |
| 7-(2-Methoxy-4-propylsulfonyloxyphenyl)-8-(4-methylbenzoyloxymethyl)-1,3,3-trimethyl-3,4-dihydro-1H-quinoxalin-2-one (Compound No. 1-52)<br/>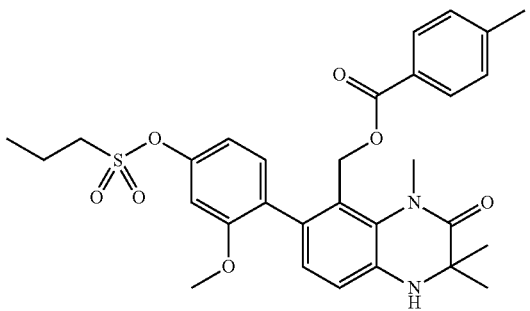 | $^1$H-NMR (400 MHz, CDCl$_3$) δ 1.13 (t, J = 7.4 Hz, 3H), 1.21 (s, 3H), 1.42 (s, 3H), 1.98-2.07 (m, 2H), 2.37 (s, 3H), 3.21-3.25 (m, 2H), 3.47 (s, 3H), 3.74 (s, 3H), 3.81 (s, 1H), 5.13 (d, J = 13.2 Hz, 1H), 5.29 (d, J = 13.2 Hz, 1H), 6.76 (d, J = 8.1 Hz, 1H), 6.83-6.86 (m, 3H), 7.16 (d, J = 8.1 Hz, 2H), 7.27 (d, J = 8.8 Hz, 1H), 7.71 (d, J = 8.1 Hz, 2H) |

| | |
|---|---|
| 8-(5-Fluoro-2-methylphenoxymethyl)-7-(2-methoxy-4-phenethylsulfonyloxyphenyl)-1,3,3-trimethyl-3,4-dihydro-1H-quinoxalin-2-one (Compound No. 1-53)<br>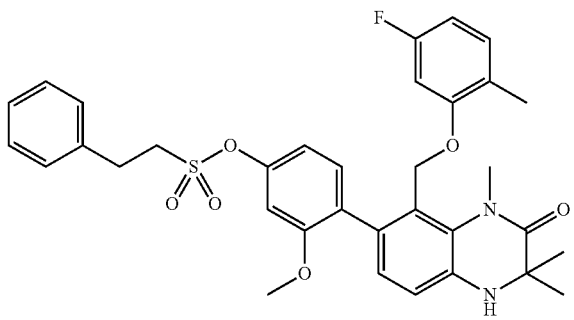 | $^1$H-NMR (400 MHz, CDCl$_3$) δ 0.98 (s, 3H), 1.27 (s, 3H), 2.01 (s, 3H), 3.29-3.33 (m, 2H), 3.46 (s, 3H), 3.54-3.58 (m, 2H), 3.74 (s, 1H), 3.82 (s, 3H), 4.80 (d, J = 13.4 Hz, 1H), 5.16 (d, J = 13.4 Hz, 1H), 6.05 (dd, J = 11.1, 2.4 Hz, 1H), 6.40 (td, J = 8.3, 2.4 Hz, 1H), 6.72 (d, J = 7.9 Hz, 1H), 6.85 (d, J = 7.9 Hz, 1H), 6.86 (d, J = 2.2 Hz, 1H), 6.88-6.92 (m, 1H), 6.91 (dd, J = 8.3, 2.2 Hz, 1H), 7.25-7.37 (m, 5H), 7.31 (d, J = 8.3 Hz, 1H) |
| 7-[4-(3-Chloropropylsulfonyloxy)-2-methoxyphenyl]-8-(5-fluoro-2-methylphenoxymethyl)-1,3,3-trimethyl-3,4-dihydro-1H-quinoxalin-2-one (Compound No. 1-54)<br>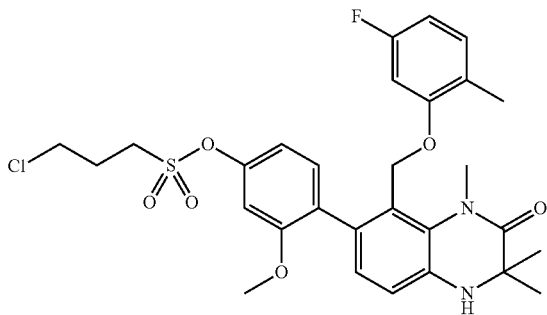 | $^1$H-NMR (500 MHz, CDCl$_3$) δ 0.99 (s, 3H), 1.27 (s, 3H), 2.01 (s, 3H), 2.45-2.51 (m, 2H), 3.46 (s, 3H), 3.49 (t, J = 7.3 Hz, 2H), 3.75 (t, J = 6.1 Hz, 3H), 3.84 (s, 3H), 4.80 (d, J = 13.4 Hz, 1H), 5.16 (d, J = 13.4 Hz, 1H), 6.06 (dd, J = 11.3, 2.4 Hz, 1H), 6.41 (td, J = 8.2, 2.4 Hz, 1H), 6.73 (d, J = 7.9 Hz, 1H), 6.86 (d, J = 7.9 Hz, 1H), 6.90-6.92 (m, 1H), 6.92 (d, J = 2.4 Hz, 1H), 6.96 (dd, J = 8.2, 2.4 Hz, 1H), 7.33 (d, J = 8.2 Hz, 1H) |
| 7-(4-Chloromethylsulfonyloxy-2-methoxyphenyl)-8-(5-fluoro-2-methylphenoxymethyl)-1,3,3-trimethyl-3,4-dihydro-1H-quinoxalin-2-one (Compound No. 1-55)<br>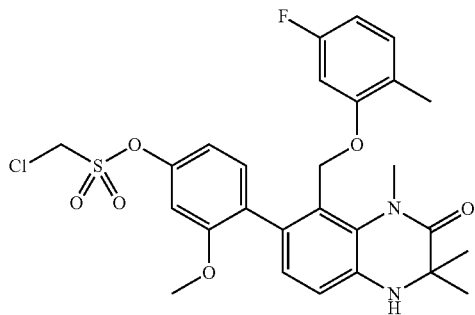 | $^1$H-NMR (400 MHz, CDCl$_3$) δ 1.01 (s, 3H), 1.28 (s, 3H), 2.01 (s, 3H), 3.46 (s, 3H), 3.77 (s, 1H), 3.84 (s, 3H), 4.68 (s, 2H), 4.77 (d, J = 13.3 Hz, 1H), 5.15 (d, J = 13.3 Hz, 1H), 6.06 (dd, J = 11.2, 2.4 Hz, 1H), 6.42 (td, J = 8.3, 2.4 Hz, 1H), 6.74 (d, J = 8.1 Hz, 1H), 6.85 (d, J = 8.1 Hz, 1H), 6.90-6.94 (m, 1H), 6.95 (d, J = 2.2 Hz, 1H), 7.02 (dd, J = 8.3, 2.2 Hz, 1H), 7.35 (d, J = 8.3 Hz, 1H) |

| | |
|---|---|
| 7-(4-Cyclopropylsulfonyloxy-2-methoxyphenyl)-8-(5-fluoro-2-methylphenylaminomethyl)-1,3,3-trimethyl-3,4-dihydro-1H-quinoxalin-2-one (Compound No. 1-56)<br>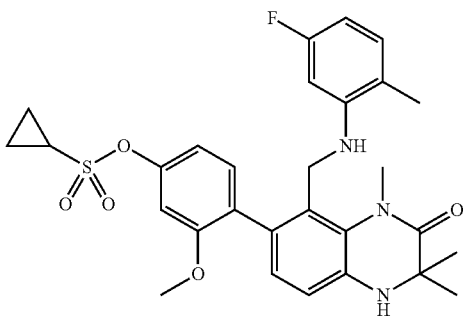 | $^1$H-NMR (500 MHz, CDCl$_3$) δ 1.04-1.06 (m, 2H), 1.18 (s, 3H), 1.22-1.25 (m, 2H), 1.40 (s, 3H), 1.85 (s, 3H), 2.50 (tt, J = 7.9, 4.6 Hz, 1H), 3.43 (s, 3H), 3.72-3.75 (m, 1H), 3.78 (s, 1H), 3.80 (s, 3H), 4.10 (dd, J = 13.9, 5.5 Hz, 1H), 4.18 (dd, J = 13.9, 4.9 Hz, 1H), 5.97 (dd, J = 11.6, 2.5 Hz, 1H), 6.22 (td, J = 8.3, 2.5 Hz, 1H), 6.72 (d, J = 8.1 Hz, 1H), 6.80-6.84 (m, 1H), 6.82 (d, J = 8.1 Hz, 1H), 6.91 (d, J = 2.3 Hz, 1H), 6.97 (dd, J = 8.2, 2.3 1H), 7.22 (d, J = 8.2 Hz, 1H) |
| 7-(4-Cyclopentylsulfonyloxy-2-methoxyphenyl)-8-(5-fluoro-2-methylphenylaminomethyl)-1,3,3-trimethyl-3,4-dihydro-1H-quinoxalin-2-one (Compound No. 1-57)<br>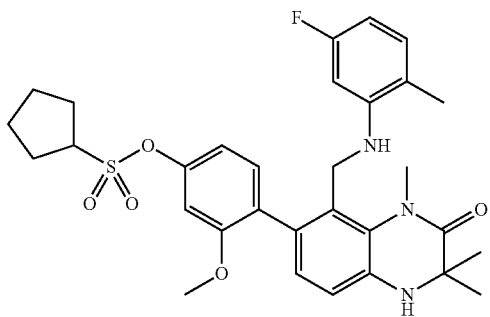 | $^1$H-NMR (400 MHz, CDCl$_3$) δ 1.17 (s, 3H), 1.40 (s, 3H), 1.67-1.73 (m, 2H), 1.84 (s, 3H), 1.86-1.92 (m, 2H), 2.10-2.16 (m, 2H), 2.21-2.26 (m, 2H), 3.42 (s, 3H), 3.64-3.70 (m, 1H), 3.72-3.76 (m, 1H), 3.78 (s, 1H), 3.80 (s, 3H), 4.12 (dd, J = 14.1, 5.1 Hz, 1H), 4.20 (dd, J = 14.1, 4.9 Hz, 1H), 5.97 (dd, J = 11.6, 2.5 Hz, 1H), 6.22 (td, J = 8.4, 2.5 Hz, 1H), 6.71 (d, J = 7.9 Hz, 1H), 6.81-6.84 (m, 1H), 6.81 (d, J = 7.9 Hz, 1H), 6.89 (d, J = 2.3 Hz, 1H), 6.92 (dd, J = 8.1, 2.3 Hz, 1H), 7.21 (d, J = 8.1 Hz, 1H) |
| 8-(5-Fluoro-2-methylphenyl-aminomethyl)-7-(2-methoxy-4-propylsulfonyloxyphenyl)-1,3,3-trimethyl-3,4-dihydro-1H-quinoxalin-2-one (Compound No. 1-58)<br>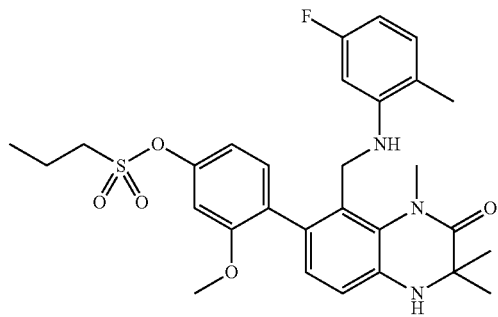 | $^1$H-NMR (400 MHz, CDCl$_3$) δ 1.13 (t, J = 7.4 Hz, 3H), 1.17 (s, 3H), 1.40 (s, 3H), 1.84 (s, 3H), 1.98-2.06 (m, 2H), 3.20-3.24 (m, 2H), 3.42 (s, 3H), 3.71-3.75 (m, 1H), 3.78 (s, 1H), 3.80 (s, 3H), 4.13 (dd, J = 13.9, 5.0 Hz, 1H), 4.21 (dd, J = 13.9, 4.9 Hz, 1H), 5.97 (dd, J = 11.5, 2.5 Hz, 1H), 6.22 (td, J = 8.4, 2.5 Hz, 1H), 6.71 (d, J = 7.9 Hz, 1H), 6.80-6.85 (m, 1H), 6.81 (d, J = 7.9 Hz, 1H), 6.89 (d, J = 2.3 Hz, 1H), 6.92 (dd, J = 8.2, 2.3 Hz, 1H), 7.23 (d, J = 8.2 Hz, 1H) |

Example 2

7-(2-Methoxy-4-methylsulfonyloxyphenyl)-8-(2-methoxyphenylaminomethyl)-1,3,3-trimethyl-3,4-dihydro-1H-quinoxalin-2-one

Compound No. 2-1

8-[N-(9-Fluorenylmethoxycarbonyl)-N-(2-methoxyphenyl)aminomethyl]-7-(4-hydroxy-2-methoxyphenyl)-1,3,3-trimethyl-3,4-dihydro-1H-quinoxalin-2-one (Reference Compound No. 14-6, 30.9 mg, 0.0461 mmol) was dissolved in dichloromethane (0.5 mL), and triethylamine (16 μL, 0.115 mmol) and methanesulfonyl chloride (5 μL, 0.0646 mmol) were added thereto successively. After the reaction mixture was stirred at room temperature for 1 hour, it was purified by silica gel column chromatography (hexane-ethyl acetate). The obtained colorless amorphous product was dissolved in N,N-dimethylformamide (0.5 mL) and piperidine (30 μL) was added thereto. After the reaction mixture was stirred at room temperature for 20 minutes, it was diluted with ethyl acetate (30 mL). The mixture was washed with water (30 mL) and saturated brine (30 mL) successively, dried over anhydrous magnesium sulfate, and then the solvent was removed under reduced pressure. The obtained residue was purified by silica gel column chromatography (hexane-ethyl acetate) to give the titled compound (13.7 mg) as a colorless solid. (Yield 56%)

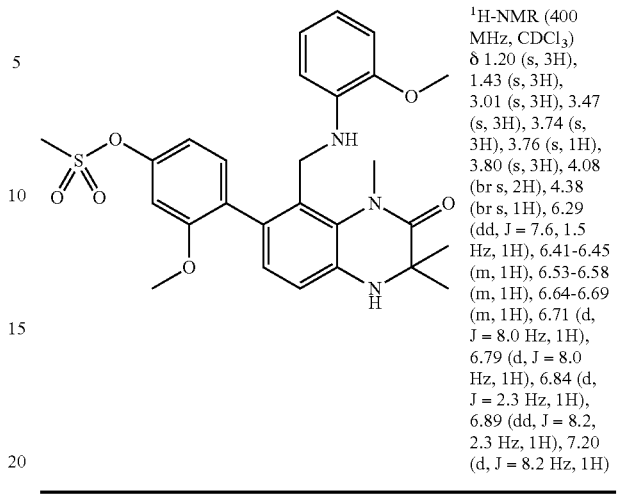

$^1$H-NMR (400 MHz, CDCl$_3$) δ 1.20 (s, 3H), 1.43 (s, 3H), 3.01 (s, 3H), 3.47 (s, 3H), 3.74 (s, 3H), 3.76 (s, 3H), 3.80 (s, 3H), 4.08 (br s, 2H), 4.38 (br s, 1H), 6.29 (dd, J = 7.6, 1.5 Hz, 1H), 6.41-6.45 (m, 1H), 6.53-6.58 (m, 1H), 6.64-6.69 (m, 1H), 6.71 (d, J = 8.0 Hz, 1H), 6.79 (d, J = 8.0 Hz, 1H), 6.84 (d, J = 2.3 Hz, 1H), 6.89 (dd, J = 8.2, 2.3 Hz, 1H), 7.20 (d, J = 8.2 Hz, 1H)

Using any compounds among Reference Compound. No. 14-6 and available compounds, the following Compounds (No. 2-2~2-8) were obtained by a method similar to that of Compound No. 2-1.

8-(2-Methoxyphenylaminomethyl)-7-(2-methoxy-4-phenylsulfonyloxyphenyl)-1,3,3-trimethyl-3,4-dihydro-1H-quinoxalin-2-one (Compound No. 2-2)

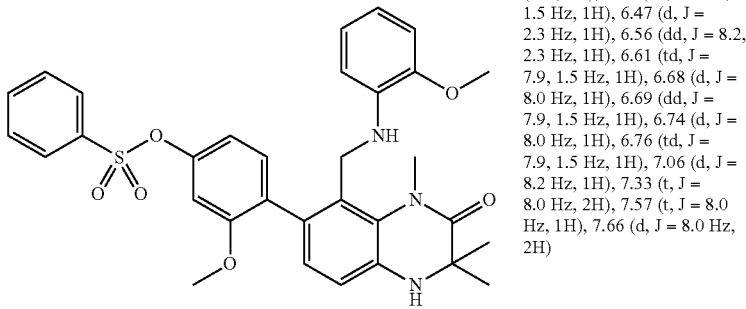

$^1$H-NMR (500 MHz, CDCl$_3$) δ 1.19 (s, 3H), 1.42 (s, 3H), 3.46 (s, 3H), 3.62 (s, 3H), 3.75 (s, 1H), 3.76 (s, 3H), 3.99-4.00 (m, 2H), 4.39 (br s, 1H), 6.32 (dd, J = 7.9, 1.5 Hz, 1H), 6.47 (d, J = 2.3 Hz, 1H), 6.56 (dd, J = 8.2, 2.3 Hz, 1H), 6.61 (td, J = 7.9, 1.5 Hz, 1H), 6.68 (d, J = 8.0 Hz, 1H), 6.69 (dd, J = 7.9, 1.5 Hz, 1H), 6.74 (d, J = 8.0 Hz, 1H), 6.76 (td, J = 7.9, 1.5 Hz, 1H), 7.06 (d, J = 8.2 Hz, 1H), 7.33 (t, J = 8.0 Hz, 2H), 7.57 (t, J = 8.0 Hz, 1H), 7.66 (d, J = 8.0 Hz, 2H)

7-(4-Cyclopropylsulfonyloxy-2-methoxyphenyl)-8-(2-methoxyphenylaminoethyl)-1,3,3-trimethyl-3,4-dihydro-1H-quinoxalin-2-one (Compound No. 2-3)

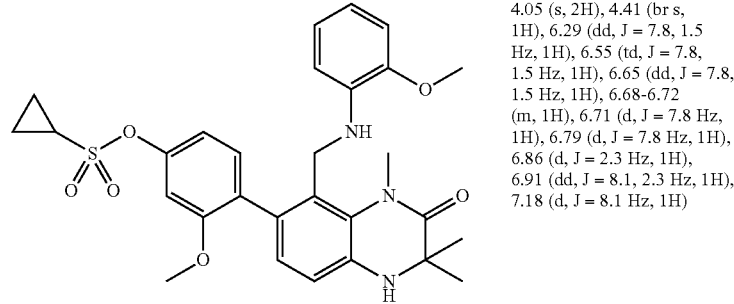

$^1$H-NMR (400 MHz, CDCl$_3$) δ 0.96-0.98 (m, 2H), 1.16-1.19 (m, 2H), 1.21 (s, 3H), 1.43 (s, 3H), 2.33-2.38 (m, 1H), 3.48 (s, 3H), 3.74 (s, 3H), 3.76 (s, 1H), 3.79 (s, 3H), 4.05 (s, 2H), 4.41 (br s, 1H), 6.29 (dd, J = 7.8, 1.5 Hz, 1H), 6.55 (td, J = 7.8, 1.5 Hz, 1H), 6.65 (dd, J = 7.8, 1.5 Hz, 1H), 6.68-6.72 (m, 1H), 6.71 (d, J = 7.8 Hz, 1H), 6.79 (d, J = 7.8 Hz, 1H), 6.86 (d, J = 2.3 Hz, 1H), 6.91 (dd, J = 8.1, 2.3 Hz, 1H), 7.18 (d, J = 8.1 Hz, 1H)

| | |
|---|---|
| 8-(2-Methoxyphenylaminomethyl)-7-[2-methoxy-4-(3,3,3-trifluoropropylsulfonyloxy)phenyl]-1,3,3-trimethyl-3,4-dihydro-1H-quinoxalin-2-one (Compound No. 2-4) 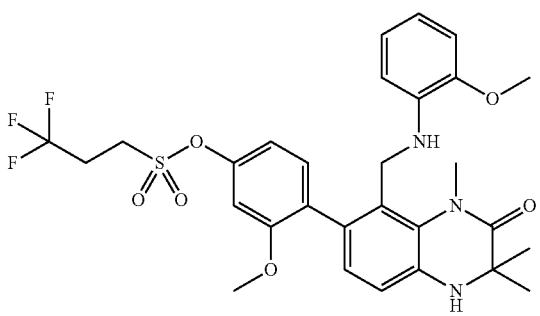 [SMILES: COc1ccccc1NCc1c(-c2ccc(OS(=O)(=O)CCC(F)(F)F)cc2OC)ccc2c1N(C)C(=O)C(C)(C)N2] | $^1$H-NMR (400 MHz, CDCl$_3$) δ 1.20 (s, 3H), 1.43 (s, 3H), 2.74-2.86 (m, 2H), 3.39-3.44 (m, 2H), 3.46 (s, 3H), 3.73 (s, 3H), 3.77 (s, 1H), 3.80 (s, 3H), 4.09 (s, 2H), 4.39 (br s, 1H), 6.29 (dd, J = 7.8, 1.4 Hz, 1H), 6.56 (td, J = 7.8, 1.4 Hz, 1H), 6.66 (dd, J = 7.8, 1.4 Hz, 1H), 6.69-6.74 (m, 1H), 6.70 (d, J = 7.8 Hz, 1H), 6.78 (d, J = 7.8 Hz, 1H), 6.80 (d, J = 2.4 Hz, 1H), 6.85 (dd, J = 8.1, 2.4 Hz, 1H), 7.22 (d, J = 8.3 Hz, 1H) |
| 7-(4-Isobutylsulfonyloxy-2-methoxyphenyl)-8-(2-methoxyphenylaminomethyl)-1,3,3-trimethyl-3,4-dihydro-1H-quinoxalin-2-one (Compound No. 2-5) 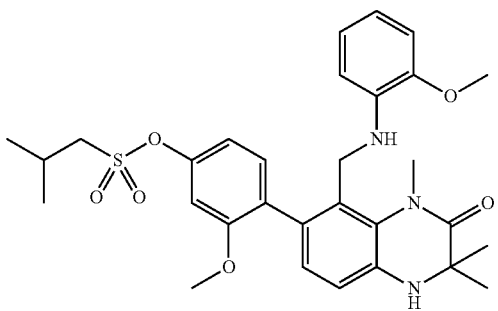 [SMILES: COc1ccccc1NCc1c(-c2ccc(OS(=O)(=O)CC(C)C)cc2OC)ccc2c1N(C)C(=O)C(C)(C)N2] | $^1$H-NMR (400 MHz, CDCl$_3$) δ 1.16 (d, J = 6.7 Hz, 6H), 1.19 (s, 3H), 1.42 (s, 3H), 2.39-2.47 (m, 1H), 3.12 (d, J = 6.4 Hz, 2H), 3.46 (s, 3H), 3.73 (s, 3H), 3.75 (s, 1H), 3.79 (s, 3H), 4.10 (s, 2H), 4.41 (br s, 1H), 6.30 (dd, J = 7.7, 1.5 Hz), 6.56 (td, J = 7.7, 1.5 Hz, 1H), 6.65 (dd, J = 7.7, 1.5 Hz, 1H), 6.70 (d, J = 7.9 Hz, 1H), 6.71 (td, J = 7.7, 1.5 Hz, 1H), 6.79 (d, J = 7.9 Hz, 1H), 6.84 (d, J = 2.3 Hz, 1H), 6.87 (dd, J = 8.2, 2.3 Hz, 1H), 7.19 (d, J = 8.2 Hz, 1H) |
| 7-(4-Isopropylsulfonyloxy-2-methoxyphenyl)-8-(2-methoxyphenylaminomethyl)-1,3,3-trimethyl-3,4-dihydro-1H-quinoxalin-2-one (Compound No. 2-6) 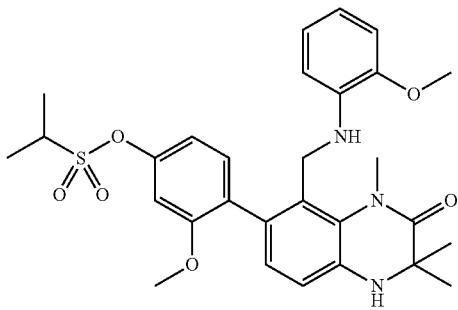 [SMILES: COc1ccccc1NCc1c(-c2ccc(OS(=O)(=O)C(C)C)cc2OC)ccc2c1N(C)C(=O)C(C)(C)N2] | $^1$H-NMR (400 MHz, CDCl$_3$) δ 1.19 (s, 3H), 1.42 (s, 3H), 1.54 (d, J = 6.8 Hz, 6H), 3.41 (sept, J = 6.8 Hz, 1H), 3.46 (s, 3H), 3.73 (s, 3H), 3.76 (s, 1H), 3.79 (s, 3H), 4.10 (s, 2H), 4.43 (br s, 1H), 6.30 (dd, J = 7.8, 1.4 Hz, 1H), 6.56 (td, J = 7.8, 1.4 Hz, 1H), 6.66 (dd, J = 7.8, 1.4 Hz, 1H), 6.70 (d, J = 8.1 Hz, 1H), 6.71 (td, J = 7.8, 1.4 Hz, 1H), 6.79 (d, J = 8.1 Hz, 1H), 6.84 (d, J = 2.2 Hz, 1H), 6.88 (dd, J = 8.2, 2.2 Hz, 1H), 7.18 (d, J = 8.2 Hz, 1H) |

| | |
|---|---|
| 7-(4-Cyclopentylsulfonyloxy-2-methoxyphenyl)-8-(2-methoxyphenylaminomethyl)-1,3,3-trimethyl-3,4-dihydro-1H-quinoxalin-2-one (Compound No. 2-7)<br />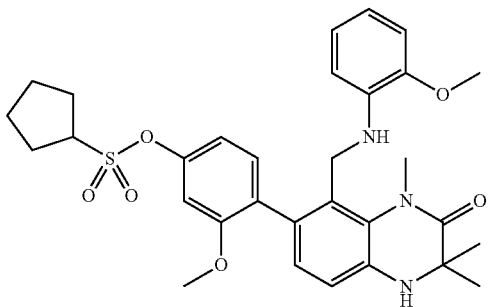 [SMILES: COc1ccccc1NCc1c(-c2ccc(OS(=O)(=O)C3CCCC3)cc2OC)ccc2c1N(C)C(=O)C(C)(C)N2] | $^1$H-NMR (500 MHz, CDCl$_3$) δ 1.19 (s, 3H), 1.42 (s, 3H), 1.66-1.69 (m, 2H), 1.85-1.89 (m, 2H), 2.07-2.13 (m, 2H), 2.19-2.24 (m, 2H), 3.46 (s, 3H), 3.58-3.62 (m, 1H), 3.73 (s, 3H), 3.75 (s, 1H), 3.79 (s, 3H), 4.09 (s, 2H), 4.42 (br s, 1H), 6.29 (dd, J = 7.8, 1.4 Hz, 1H), 6.56 (td, J = 7.8, 1.4 Hz, 1H), 6.65 (dd, J = 7.8, 1.4 Hz, 1H), 6.70 (d, J = 7.9 Hz, 1H), 6.71 (td, J = 7.8, 1.4 Hz, 1H), 6.78 (d, J = 7.9 Hz, 1H), 6.84 (d, J = 2.3 Hz, 1H), 6.88 (dd, J = 8.2, 2.3 Hz, 1H), 7.18 (d, J = 8.2 Hz, 1H) |
| 8-(2-Methoxyphenylaminomethyl)-7-(2-methoxy-4-propylsulfonyloxyphenyl)-1,3,3-trimethyl-3,4-dihydro-1H-quinoxalin-2-one (Compound No. 2-8)<br />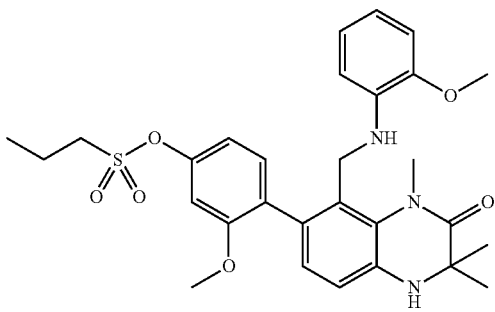 [SMILES: CCCS(=O)(=O)Oc1ccc(-c2ccc3c(c2CNc2ccccc2OC)N(C)C(=O)C(C)(C)N3)c(OC)c1] | $^1$H-NMR (500 MHz, CDCl$_3$) δ 1.11 (t, J = 7.5 Hz, 3H), 1.19 (s, 3H), 1.42 (s, 3H), 1.96-2.04 (m, 2H), 3.15-3.18 (m, 2H), 3.46 (s, 3H), 3.73 (s, 3H), 3.76 (br s, 1H), 3.79 (s, 3H), 4.10 (br s, 2H), 4.40 (br s, 1H), 6.29 (d, J = 7.6 Hz, 1H), 6.56 (t, J = 7.6 Hz, 1H), 6.65 (d, J = 7.6 Hz, 1H), 6.70 (d, J = 7.9 Hz, 1H), 6.71 (t, J = 7.6 Hz, 1H), 6.78 (d, J = 7.9 Hz, 1H), 6.84 (d, J = 1.9 Hz, 1H), 6.87 (dd, J = 8.0, 1.9 Hz, 1H), 7.19 (d, J = 8.0 Hz, 1H) |

Example 3

7-[4-(3-Benzylaminopropylsulfonyloxy)-2-methoxyphenyl]-8-(5-fluoro-2-methylphenoxymethyl)-1,3,3-trimethyl-3,4-dihydro-1H-quinoxalin-2-one Compound No. 3-1

A mixture of 7-[4-(3-chloropropylsulfonyloxy)-2-methoxyphenyl]-8-(5-fluoro-2-methylphenoxymethyl)-1,3,3-trimethyl-3,4-dihydro-1H-quinoxalin-2-one (Reference Compound No. 1-54, 50.0 mg, 0.0846 mmol), benzylamine (92.4 μL, 0.846 mmol), and potassium iodide (16.9 mg, 0.102 mmol) was suspended in anhydrous N,N-dimethylformamide (0.4 mL) and stirred at 50° C. for 5 hours. After cooling down, ethyl acetate (50 mL) was added thereto. The organic layer was washed with water (50 mL) and saturated brine (30 mL), dried over anhydrous magnesium sulfate, and then the solvent was removed under reduced pressure. The obtained residue was purified by silica gel column chromatography (hexane-ethyl acetate) to give the titled compound (21.4 mg) as a colorless amorphous product. (Yield 38%)

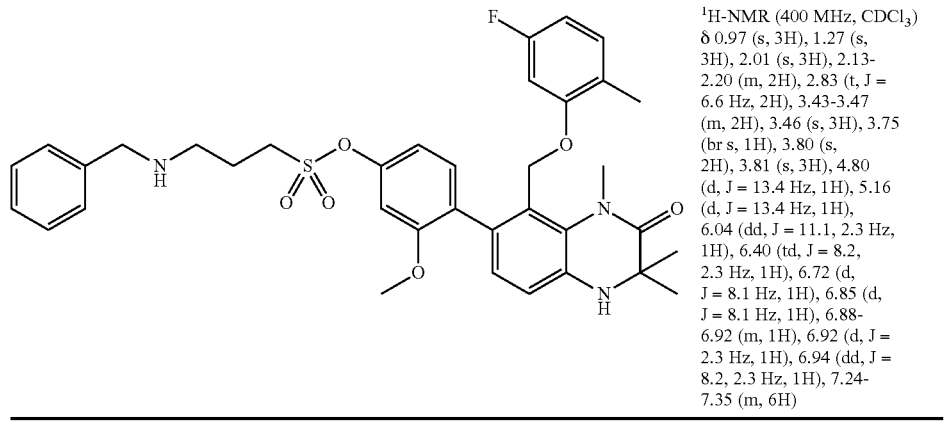

| | ¹H-NMR (400 MHz, CDCl₃) δ 0.97 (s, 3H), 1.27 (s, 3H), 2.01 (s, 3H), 2.13-2.20 (m, 2H), 2.83 (t, J = 6.6 Hz, 2H), 3.43-3.47 (m, 2H), 3.46 (s, 3H), 3.75 (br s, 1H), 3.80 (s, 2H), 3.81 (s, 3H), 4.80 (d, J = 13.4 Hz, 1H), 5.16 (d, J = 13.4 Hz, 1H), 6.04 (dd, J = 11.1, 2.3 Hz, 1H), 6.40 (td, J = 8.2, 2.3 Hz, 1H), 6.72 (d, J = 8.1 Hz, 1H), 6.85 (d, J = 8.1 Hz, 1H), 6.88-6.92 (m, 1H), 6.92 (d, J = 2.3 Hz, 1H), 6.94 (dd, J = 8.2, 2.3 Hz, 1H), 7.24-7.35 (m, 6H) |

Using any compounds among Compound No. 1-54 and available compounds, the following Compounds (No. 3-2~3-6) were obtained by a method similar to that of Compound No. 3-1.

| 8-(5-Fluoro-2-methylphenoxymethyl)-7-[2-methoxy-4-(3-propyl-aminopropylsulfonyloxy)phenyl]-1,3,3-trimethyl-3,4-dihydro-1H-quinoxalin-2-one (Compound No. 3-2) 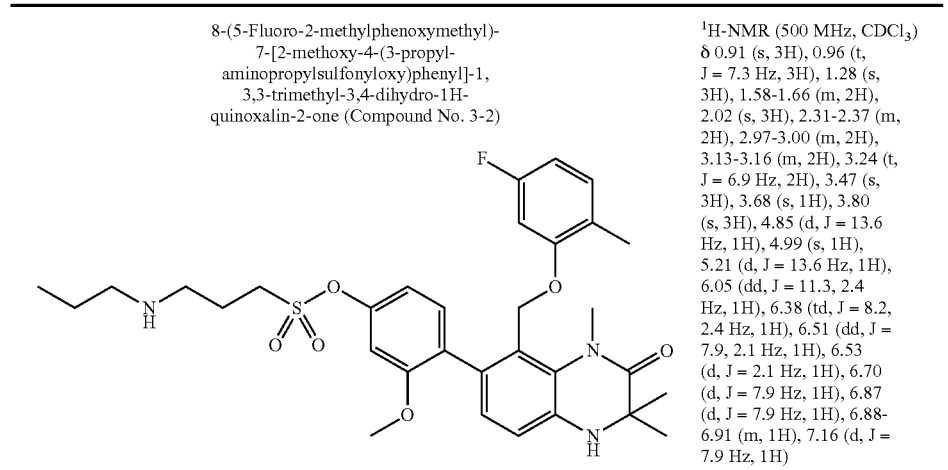 | ¹H-NMR (500 MHz, CDCl₃) δ 0.91 (s, 3H), 0.96 (t, J = 7.3 Hz, 3H), 1.28 (s, 3H), 1.58-1.66 (m, 2H), 2.02 (s, 3H), 2.31-2.37 (m, 2H), 2.97-3.00 (m, 2H), 3.13-3.16 (m, 2H), 3.24 (t, J = 6.9 Hz, 2H), 3.47 (s, 3H), 3.68 (s, 1H), 3.80 (s, 3H), 4.85 (d, J = 13.6 Hz, 1H), 4.99 (s, 1H), 5.21 (d, J = 13.6 Hz, 1H), 6.05 (dd, J = 11.3, 2.4 Hz, 1H), 6.38 (td, J = 8.2, 2.4 Hz, 1H), 6.51 (dd, J = 7.9, 2.1 Hz, 1H), 6.53 (d, J = 2.1 Hz, 1H), 6.70 (d, J = 7.9 Hz, 1H), 6.87 (d, J = 7.9 Hz, 1H), 6.88-6.91 (m, 1H), 7.16 (d, J = 7.9 Hz, 1H) |
| 8-(5-Fluoro-2-methylphenoxymethyl)-7-[2-methoxy-4-[3-(morpholin-4-yl)propylsulfonyloxy]phenyl]-1,3,3-trimethyl-3,4-dihydro-1H-quinoxalin-2-one (Compound No. 3-3) 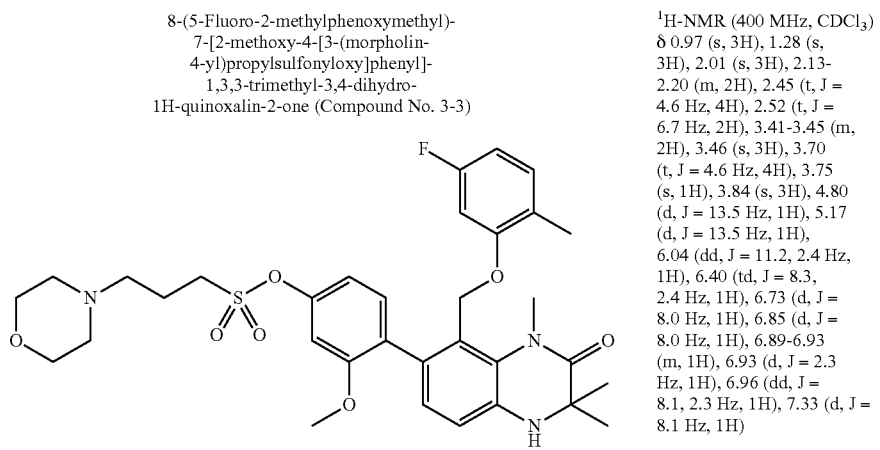 | ¹H-NMR (400 MHz, CDCl₃) δ 0.97 (s, 3H), 1.28 (s, 3H), 2.01 (s, 3H), 2.13-2.20 (m, 2H), 2.45 (t, J = 4.6 Hz, 4H), 2.52 (t, J = 6.7 Hz, 2H), 3.41-3.45 (m, 2H), 3.46 (s, 3H), 3.70 (t, J = 4.6 Hz, 4H), 3.75 (s, 1H), 3.84 (s, 3H), 4.80 (d, J = 13.5 Hz, 1H), 5.17 (d, J = 13.5 Hz, 1H), 6.04 (dd, J = 11.2, 2.4 Hz, 1H), 6.40 (td, J = 8.3, 2.4 Hz, 1H), 6.73 (d, J = 8.0 Hz, 1H), 6.85 (d, J = 8.0 Hz, 1H), 6.89-6.93 (m, 1H), 6.93 (d, J = 2.3 Hz, 1H), 6.96 (dd, J = 8.1, 2.3 Hz, 1H), 7.33 (d, J = 8.1 Hz, 1H) |

| Compound | NMR |
|---|---|
| 8-(5-Fluoro-2-methylphenoxymethyl)-7-[2-methoxy-4-[3-(piperidin-1-yl)propylsulfonoyloxyphenyl]-1,3,3-trimethyl-3,4-dihydro-1H-quinoxalin-2-one (Compound No. 3-4) 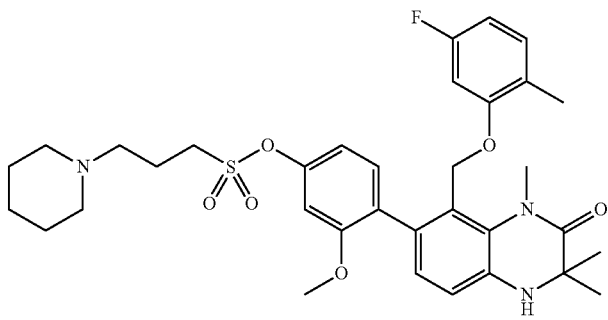 [SMILES: COc1cc(OS(=O)(=O)CCCN2CCCCC2)ccc1-c1ccc2c(c1COc1cc(F)ccc1C)N(C)C(=O)C(C)(C)N2] | $^1$H-NMR (500 MHz, CDCl$_3$) δ 0.97 (s, 3H), 1.27 (s, 3H), 1.40-1.45 (m, 2H), 1.54-1.60 (m, 4H), 2.01 (s, 3H), 2.13-2.18 (m, 2H), 2.37 (br s, 4H), 2.45 (t, J = 6.7 Hz, 2H), 3.38-3.42 (m, 2H), 3.46 (s, 3H), 3.74 (s, 1H), 3.84 (s, 3H), 4.81 (d, J = 13.4 Hz, 1H), 5.17 (d, J =13.4 Hz, 1H), 6.05 (dd, J = 11.0, 2.4 Hz, 1H), 6.40 (td, J = 8.2, 2.4 Hz, 1H), 6.72 (d, J = 7.9 Hz, 1H), 6.85 (d, J = 7.9 Hz, 1H), 6.89-6.92 (m, 1H), 6.93 (d, J = 2.1 Hz, 1H), 6.97 (dd, J = 8.2, 2.1 Hz, 1H), 7.32 (d, J = 8.2 Hz, 1H) |
| 7-[4-[3-[N-(2-Dimethylaminoethyl)-N-methylamino]propylsulfonyloxy]-2-methoxyphenyl]-8-(5-fluoro-2-methylphenoxymethyl)-1,3,3-trimethyl-3,4-dihydro-1H-quinoxalin-2-one (Compound No. 3-5) 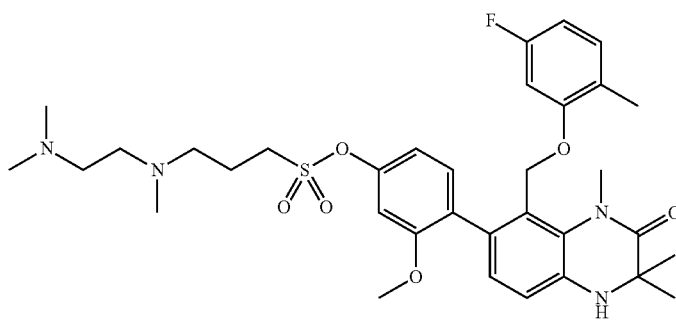 | $^1$H-NMR (400 MHz, CDCl$_3$) δ 0.97 (s, 3H), 1.27 (s, 3H), 2.01 (s, 3H), 2.11-2.18 (m, 2H), 2.23 (s, 6H), 2.25 (s, 3H), 2.38 (dd, J = 7.7, 5.5 Hz, 2H), 2.49 (dd, J = 7.7, 5.5 Hz, 2H), 2.55 (t, J = 6.7 Hz, 2H), 3.40-3.44 (m, 2H), 3.46 (s, 3H), 3.74 (s, 1H), 3.84 (s, 3H), 4.81 (d, J = 13.4 Hz, 1H), 5.18 (d, J = 13.4 Hz, 1H), 6.05 (dd, J = 11.2, 2.4 Hz, 1H), 6.40 (td, J = 8.3, 2.4 Hz, 1H), 6.72 (d, J = 8.0 Hz, 1H), 6.86 (d, J = 8.0 Hz, 1H), 6.89-6.93 (m, 1H), 6.93 (d, J = 2.2 Hz, 1H), 6.96 (dd, J = 8.2, 2.2 Hz, 1H), 7.32 (d, J = 8.2 Hz, 1H) |
| 8-(5-Fluoro-2-methylphenoxymethyl)-7-[2-methoxy-4-[3-[N-(2-methylaminoethyl)-N-methylamino]propylsulfonyloxy]phenyl]-1,3,3-trimethyl-3,4-dihydro-1H-quinoxalin-2-one (Compound No. 3-6) 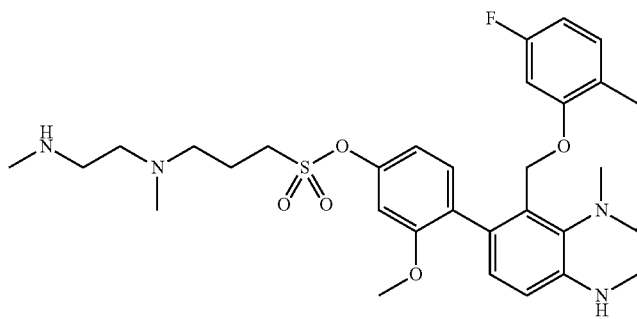 | $^1$H-NMR (500 MHz, CDCl$_3$) δ 0.97 (s, 3H), 1.27 (s, 3H), 2.01 (s, 3H), 2.12-2.18 (m, 2H), 2.23 (s, 3H), 2.44 (s, 3H), 2.51 (t, J = 6.0 Hz, 2H), 2.54 (t, J = 6.6 Hz, 2H), 2.65 (t, J = 6.0 Hz, 2H), 3.39-3.42 (m, 2H), 3.46 (s, 3H), 3.74 (s, 1H), 3.84 (s, 3H), 4.81 (d, J = 13.4 Hz, 1H), 5.17 (d, J = 13.4 Hz, 1H), 6.05 (dd, J = 11.3, 2.4 Hz, 1H), 6.40 (td, J = 8.2, 2.4 Hz, 1H), 6.72 (d, J = 8.1 Hz, 1H), 6.86 (d, J = 8.1 Hz, 1H), 6.89-6.92 (m, 1H), 6.93 (d, J = 2.4 Hz, 1H), 6.96 (dd, J = 8.2, 2.4 Hz, 1H), 7.32 (d, J = 8.2 Hz, 1H) |

Preparation Examples

Hereinafter, typical preparation examples of the present compound are shown.
1) Tablet (in 150 mg)

| | |
|---|---|
| The present compound | 1 mg |
| Lactose | 100 mg |
| Cornstarch | 40 mg |
| Carboxymethyl cellulose calcium | 4.5 mg |
| Hydroxypropyl cellulose | 4 mg |
| Magnesium stearate | 0.5 mg |

A tablet of the above-mentioned formulation is coated with 3 mg of a coating agent (for example, a coating agent which is used conventionally such as hydroxypropylmethyl cellulose, macrogol or a silicone resin), whereby an objective tablet can be obtained. In addition, a desired tablet can be obtained by appropriately changing the kind and/or amount of the present compound and additives.
2) Capsule (in 150 mg)

| | |
|---|---|
| The present compound | 5 mg |
| Lactose | 135 mg |
| Carboxymethyl cellulose calcium | 4.5 mg |
| Hydroxypropyl cellulose | 4 mg |
| Magnesium stearate | 1.5 mg |

A desired capsule can be obtained by appropriately changing the kind and/or amount of the present compound and additives.
3) Eye Drop (in 100 mL)

| | |
|---|---|
| The present compound | 100 mg |
| Sodium chloride | 900 mg |
| Polysorbate 80 | 500 mg |
| Sodium hydroxide | q.s. |
| Hydrochloric acid | q.s. |
| Sterile purified water | q.s. |

A desired eye drop can be obtained by appropriately changing the kind and/or amount of the present compound and additives.
[Pharmacological Test]
1. Evaluation Test for Binding Activity to Glucocorticoid Receptor (hereinafter referred to as "GR")

In order to evaluate a binding activity to GR, a receptor competitor assay was carried out by a fluorescence polarization method. In the assay, a GR competitor assay kit (manufactured by Invitrogen, cat No. P2816) was used, and a procedure was carried out according to the protocol attached to the kit. Hereinafter, the specific method will be described.
(Preparation of Reagents)

GR screening buffer: A buffer containing 10 mM potassium phosphate (pH 7.4), 20 mM sodium molybdate ($Na_2MoO_4$), 0.1 mM ethylene diamine tetraacetic acid (EDTA), 5 mM dithiothreitol (DTT), 0.1 mM stabilizing peptide and 2% dimethylsulfoxide was prepared.

4×GS1 solution: Fluormone™ GS1, which is a fluorescent glucocorticoid ligand, was diluted with GR screening buffer, whereby a 4 nM solution was prepared.

4×GR solution: Recombinant human GR was diluted with GR screening buffer, whereby a 16 nM solution was prepared.

(Preparation of Test Compound Solution)
After a test compound was dissolved in dimethylsulfoxide, it was diluted with GR screening buffer, whereby a 20 µM test compound solution was prepared.
(Test Method and Measurement Method)
1) The test compound solution was added in an amount of 10 µL into each well of a 384-well plate, and then, 4×GS1 solution and 4×GR solution were added in an amount of 5 µL into each well, respectively.

2) The plate was incubated in a dark place at room temperature for 2 to 4 hours.

3) By using a multimode plate reader, Analyst™ HT (manufactured by LJL Biosystems), fluorescence polarization of each well was measured. As the blank, a well containing GR screening buffer in place of the test compound and 4×GS1 solution was used.

4) The same procedure as that in the above 1) to 3) was carried out except that GR screening buffer was used in place of the test compound solution, and the obtained result was taken as the negative control.

5) The same procedure as that in the above 1) to 3) was carried out except that 2 mM dexamethasone was used in place of the test compound solution, and the obtained result was taken as the positive control.

(Calculation Equation of GR Binding Ratio)
A GR binding ratio (%) was calculated from the following equation.

GR binding ratio(%)=100×[1−(fluorescence polarization of test compound solution−fluorescence polarization of positive control solution)/(fluorescence polarization of negative control solution−fluorescence polarization of positive control solution)]

(Test Results and Discussion)
As an example of the test results, the GR binding ratios (%) of the test compounds (Compound 1-1, Compound 1-2, Compound 1-3, Compound 1-4, Compound 1-5, Compound 1-6, Compound 1-7, Compound 1-8, Compound 1-9, Compound 1-10, Compound 1-11, Compound 1-12, Compound 1-13, Compound 1-14, Compound 1-15, Compound 1-16, Compound 1-17, Compound 1-18, Compound 1-19, Compound 1-20, Compound 1-21, Compound 1-22, Compound 1-23, Compound 1-25, Compound 1-26, Compound 1-27, Compound 1-28, Compound 1-29, Compound 1-30, Compound 1-31, Compound 1-32, Compound 1-33, Compound 1-34, Compound 1-35, Compound 1-36, Compound 1-37, Compound 1-38, Compound 1-39, Compound 1-40, Compound 1-41, Compound 1-42, Compound 1-43, Compound 1-44, Compound 1-45, Compound 1-46, Compound 1-50, Compound 1-54, Compound 1-56, Compound 1-57, Compound 1-58, Compound 2-1, Compound 2-2, Compound 2-3, Compound 2-4, Compound 2-5, Compound 2-6, Compound 2-7, Compound 2-8, Compound 3-1, Compound 3-2, Compound 3-3, Compound 3-4, Compound 3-5, Compound 3-6) are shown in Table I.

TABLE I

| Test compound | GR Binding ratio (%) |
|---|---|
| Compound 1-1 | 91 |
| Compound 1-2 | 85 |
| Compound 1-3 | 99 |
| Compound 1-4 | 99 |
| Compound 1-5 | 95 |
| Compound 1-6 | 100 |
| Compound 1-7 | 86 |

TABLE I-continued

| Test compound | GR Binding ratio (%) |
|---|---|
| Compound 1-8 | 85 |
| Compound 1-9 | 100 |
| Compound 1-10 | 100 |
| Compound 1-11 | 83 |
| Compound 1-12 | 100 |
| Compound 1-13 | 100 |
| Compound 1-14 | 100 |
| Compound 1-15 | 82 |
| Compound 1-16 | 68 |
| Compound 1-17 | 65 |
| Compound 1-18 | 88 |
| Compound 1-19 | 91 |
| Compound 1-20 | 87 |
| Compound 1-21 | 92 |
| Compound 1-22 | 91 |
| Compound 1-23 | 94 |
| Compound 1-25 | 92 |
| Compound 1-26 | 95 |
| Compound 1-27 | 99 |
| Compound 1-28 | 91 |
| Compound 1-29 | 95 |
| Compound 1-30 | 92 |
| Compound 1-31 | 90 |
| Compound 1-32 | 96 |
| Compound 1-33 | 95 |
| Compound 1-34 | 100 |
| Compound 1-35 | 95 |
| Compound 1-36 | 99 |
| Compound 1-37 | 94 |
| Compound 1-38 | 100 |
| Compound 1-39 | 100 |
| Compound 1-40 | 100 |
| Compound 1-41 | 100 |
| Compound 1-42 | 100 |
| Compound 1-43 | 100 |
| Compound 1-44 | 93 |
| Compound 1-45 | 94 |
| Compound 1-46 | 95 |
| Compound 1-50 | 98 |
| Compound 1-54 | 99 |
| Compound 1-56 | 100 |
| Compound 1-57 | 93 |
| Compound 1-58 | 100 |
| Compound 2-1 | 95 |
| Compound 2-2 | 89 |
| Compound 2-3 | 93 |
| Compound 2-4 | 91 |
| Compound 2-5 | 97 |
| Compound 2-6 | 100 |
| Compound 2-7 | 99 |
| Compound 2-8 | 98 |
| Compound 3-1 | 94 |
| Compound 3-2 | 100 |
| Compound 3-3 | 100 |
| Compound 3-4 | 71 |
| Compound 3-5 | 100 |
| Compound 3-6 | 99 |

Incidentally, in the case where the GR binding ratio the test compound is 100% or more, the GR binding ratio is indicated by 100%.

As is apparent from Table I, the present compound showed an excellent GR binding activity. Accordingly, the present compound can be used as a GR modulator, and is particularly useful for a preventive or therapeutic agent for metabolic disorders, inflammatory diseases, autoimmune diseases, allergic diseases, central nervous system diseases, cardiovascular diseases, homeostasis-related diseases, glaucoma and the like.

INDUSTRIAL APPLICABILITY

The present compound has an excellent glucocorticoid receptor binding activity and is useful as a glucocorticoid receptor modulator. The present compound is particularly useful as a preventive or therapeutic agent for metabolic disorders such as diabetes and obesity, inflammatory diseases such as enteritis and chronic obstructive pulmonary diseases, autoimmune diseases such as connective tissue diseases, allergic diseases such as asthma, atopic dermatitis and allergic rhinitis, central nervous system diseases such as psychiatric disorders, Alzheimer's disease and drug use disorders, cardiovascular diseases such as hypertension, hypercalcemia, hyperinsulinemia and hyperlipidemia, homeostasis-related diseases causing an abnormality of neuro-immune-endocrine balance, glaucoma and the like.

The invention claimed is:

1. A method for modulating glucocorticoid receptor activity comprising administering a pharmacologically effective amount of a compound or a pharmaceutically acceptable salt thereof to a patient, said compound having the following formula (1):

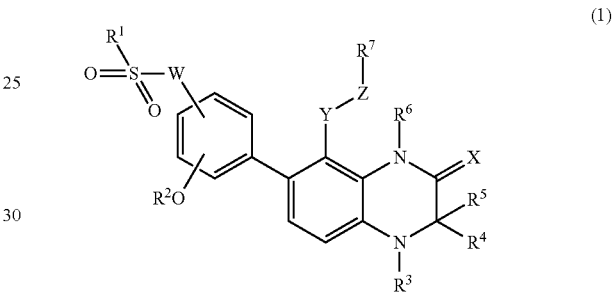

wherein
$R^1$ represents a lower alkyl group, a lower cycloalkyl group, an aryl group, a heterocyclic group or an aralkyl group;
  in the case where $R^1$ is a lower alkyl group, the lower alkyl group is unsubstituted or substituted with one or a plurality of groups selected from the group consisting of a halogen atom, a heterocyclic group, a carboxy group, a lower alkoxycarbonyl group, a lower alkylamino group, a lower alkylamino group substituted with a lower alkylamino group and a lower alkylamino group substituted with an aryl group;
  in the case where $R^1$ is an aryl group, a heterocyclic group or an aralkyl group, the aryl group, the heterocyclic group or the aralkyl group is unsubstituted or substituted with one or a plurality of groups selected from the group consisting of a halogen atom, a lower alkyl group, a hydroxyl group and a lower alkoxy group;
$R^2$ represents a hydrogen atom or a lower alkyl group;
$R^3$ represents a hydrogen atom or a lower alkyl group;
$R^4$ and $R^5$ are the same or different and represent a hydrogen atom or a lower alkyl group;
$R^6$ represents a hydrogen atom or a lower alkyl group;
$R^7$ represents a lower cycloalkyl group, an aryl group or a heterocyclic group;
  in the case where $R^7$ is an aryl group or a heterocyclic group, the aryl group or the heterocyclic group is unsubstituted or substituted with one or a plurality of groups selected from the group consisting of a halogen atom, a lower alkyl group, a hydroxyl group, a lower alkoxy group and a nitro group;
W represents an oxygen atom or $NR^8$;

R⁸ represents a hydrogen atom or a lower alkyl group;
X represents an oxygen atom or a sulfur atom;
Y represents a lower alkylene group;
Z represents an oxygen atom, a sulfur atom, NR⁹ or OCO; and
R⁹ represents a hydrogen atom or a lower alkyl group.

2. The method according to claim 1, wherein in the formula (1),
R¹ represents a lower alkyl group, a lower cycloalkyl group, an aryl group, a heterocyclic group or an aralkyl group;
  in the case where R¹ is a lower alkyl group, the lower alkyl group is unsubstituted or substituted with one or a plurality of groups selected from the group consisting of a halogen atom, a heterocyclic group, a lower alkoxycarbonyl group, a lower alkylamino group substituted with a lower alkylamino group and a lower alkylamino group substituted with an aryl group as substituent(s);
  in the case where R¹ is an aryl group, the aryl group is unsubstituted or substituted with one or a plurality of groups selected from the group consisting of a halogen atom, a lower alkyl group and a lower alkoxy group;
in the case where R¹ is an aralkyl group, the aralkyl group is unsubstituted or substituted with one or a plurality of groups selected from the group consisting of a halogen atom and a lower alkyl group
R² represents a lower alkyl group;
R³ represents a hydrogen atom;
R⁴ and R⁵ represent a lower alkyl group;
R⁶ represents a lower alkyl group;
R⁷ represents an aryl group or a heterocyclic group;
  in the case where R⁷ is an aryl group, the aryl group is unsubstituted or substituted with one or a plurality of groups selected from the group consisting of a halogen atom, a lower alkyl group, a lower alkoxy group and a nitro group;
  in the case where R⁷ is a heterocyclic group, the heterocyclic group is unsubstituted or substituted with one lower alkyl group or a plurality of lower alkyl groups;
W represents an oxygen atom or NR⁸;
R⁸ represents a hydrogen atom;
X represents an oxygen atom;
Y represents a lower alkylene group;
Z represents an oxygen atom, NR⁹ or OCO;
R⁹ represents a hydrogen atom.

3. The method according to claim 1, wherein in the formula (1), R⁴ and R⁵ represent a methyl group.

4. The method according to claim 1, wherein in the formula (1), R⁶ represents a methyl group.

5. The method according to claim 1, wherein in the formula (1), R⁷ represents a heterocyclic group, which is thiophene.

6. The method according to claim 1, wherein in the formula (1), X represents an oxygen atom.

7. The method according to claim 1, wherein in the formula (1), Y represents a methylene group.

8. The method according to claim 2, wherein in the formula (1), R⁴ and R⁵ represent a methyl group.

9. The method according to claim 2, wherein in the formula (1), R⁶ represents a methyl group.

10. The method according to claim 2, wherein in the formula (1), R⁷ represents a heterocyclic group, which is thiophene.

11. The method according to claim 2, wherein in the formula (1), Y represents a methylene group.

12. The method according to claim 1, wherein the compound is selected from the group consisting of 8-(5-fluoro-2-methylphenoxymethyl)-7-(2-methoxy-4-methylsulfonyloxyphenyl)-1,3,3-trimethyl-3,4-dihydro-1H-quinoxalin-2-one,
8-(5-fluoro-2-methylphenoxymethyl)-7-(2-methoxy-4-phenylsulfonyloxyphenyl)-1,3,3-trimethyl-3,4-dihydro-1H-quinoxalin-2-one,
8-(5-fluoro-2-methylphenoxymethyl)-7-(2-methoxy-4-trifluoromethylsulfonyloxyphenyl)-1,3,3-trimethyl-3,4-dihydro-1H-quinoxalin-2-one,
8-(5-fluoro-2-methylphenoxymethyl)-7-(2-methoxy-4-propylsulfonyloxyphenyl)-1,3,3-trimethyl-3,4-dihydro-1H-quinoxalin-2-one,
8-(5-fluoro-2-methylphenoxymethyl)-7-[2-methoxy-4-(furan-2-ylsulfonyloxy)phenyl]-1,3,3-trimethyl-3,4-dihydro-1H-quinoxalin-2-one,
7-(2-methoxy-4-methylsulfonyloxyphenyl)-8-(5-methylthiophen-2-ylcarbonyloxymethyl)-1,3,3-trimethyl-3,4-dihydro-1H-quinoxalin-2-one,
7-[4-(2-chlorophenylsulfonyloxy)-2-methoxyphenyl]-8-(5-fluoro-2-methylphenoxymethyl)-1,3,3-trimethyl-3,4-dihydro-1H-quinoxalin-2-one,
7-(4-benzylsulfonyloxy-2-methoxyphenyl)-8-(5-fluoro-2-methylphenoxymethyl)-1,3,3-trimethyl-3,4-dihydro-1H-quinoxalin-2-one,
8-(5-fluoro-2-methylphenoxymethyl)-7-[2-methoxy-4-(2-methoxycarbonylethylsulfonyloxy)phenyl]-1,3,3-trimethyl-3,4-dihydro-1H-quinoxalin-2-one,
7-(4-butylsulfonyloxy-2-methoxyphenyl)-8-(5-fluoro-2-methylphenoxymethyl)-1,3,3-trimethyl-3,4-dihydro-1H-quinoxalin-2-one,
7-(4-ethylsulfonyloxy-2-methoxyphenyl)-8-(5-fluoro-2-methylphenoxymethyl)-1,3,3-trimethyl-3,4-dihydro-1H-quinoxalin-2-one,
8-(5-fluoro-2-methylphenoxymethyl)-7-(4-isopropylsulfonyloxy-2-methoxyphenyl)-1,3,3-trimethyl-3,4-dihydro-1H-quinoxalin-2-one,
8-(5-fluoro-2-methylphenoxymethyl)-7-[2-methoxy-4-(4-methylbenzylsulfonyloxy)phenyl]-1,3,3-trimethyl-3,4-dihydro-1H-quinoxalin-2-one,
7-[4-(4-chlorobenzylsulfonyloxy)-2-methoxyphenyl]-8-(5-fluoro-2-methylphenoxymethyl)-1,3,3-trimethyl-3,4-dihydro-1H-quinoxalin-2-one,
8-(5-fluoro-2-methylphenoxymethyl)-7-(4-isobutylsulfonyloxy-2-methoxyphenyl)-1,3,3-trimethyl-3,4-dihydro-1H-quinoxalin-2-one,
8-(5-fluoro-2-methylphenoxymethyl)-7-[2-methoxy-4-(3,3,3-trifluoropropylsulfonyloxy)phenyl]-1,3,3-trimethyl-3,4-dihydro-1H-quinoxalin-2-one,
7-(4-cyclopropylsulfonyloxy-2-methoxyphenyl)-8-(5-fluoro-2-methylphenoxymethyl)-1,3,3-trimethyl-3,4-dihydro-1H-quinoxalin-2-one,
8-(5-fluoro-2-methylphenoxymethyl)-7-(2-methoxy-4-methylsulfonylaminophenyl)-1,3,3-trimethyl-3,4-dihydro-1H-quinoxalin-2-one,
7-[4-(2-chlorobenzylsulfonyloxy)-2-methoxyphenyl]-8-(5-fluoro-2-methylphenoxymethyl)-1,3,3-trimethyl-3,4-dihydro-1H-quinoxalin-2-one,
8-(5-fluoro-2-methylphenoxymethyl)-7-[2-methoxy-4-(2-methylbenzylsulfonyloxy)phenyl]-1,3,3-trimethyl-3,4-dihydro-1H-quinoxalin-2-one,
7-(4-cyclopentylsulfonyloxy-2-methoxyphenyl)-8-(5-fluoro-2-methylphenoxymethyl)-1,3,3-trimethyl-3,4-dihydro-1H-quinoxalin-2-one,
7-(4-cyclohexylsulfonyloxy-2-methoxyphenyl)-8-(5-fluoro-2-methylphenoxymethyl)-1,3,3-trimethyl-3,4-dihydro-1H-quinoxalin-2-one, 8-(5-fluoro-2-methylphenoxymethyl)-7-[2-methoxy-4-(3-methylbenzylsulfonyloxy)phenyl]-1,3,3-trimethyl-3,4-dihydro-1H-quinoxalin-2-one, 7-(4-cyclopropylsulfonyloxy-2-methoxyphenyl)-8-(5-methylthiophen-2-ylcarbonyloxymethyl)-1,3,3-trimethyl-3,4-dihydro-1H-quinoxalin-2-one, 7-[2-methoxy-4-(3,3,3-trifluoropropylsulfonyloxy)phenyl]-8-(5-methylthiophen-2-ylcarbonyloxymethyl)-1,3,3-trimethyl-3,4-dihydro-1H-quinoxalin-2-one, 7-(4-isobutylsulfonyloxy-2-methoxyphenyl)-8-(5-methylthiophen-2-ylcarbonyloxymethyl)-1,3,3-trimethyl-3,4-dihydro-1H-quinoxalin-2-one, 7-(2-methoxy-4-propylsulfonyloxyphenyl)-8-(5-methylthiophen-2-ylcarbonyloxymethyl)-1,3,3-trimethyl-3,4-dihydro-1H-quinoxalin-2-one, 7-(4-isopropylsulfonyloxy-2-methoxyphenyl)-8-(5-methylthiophen-2-ylcarbonyloxymethyl)-1,3,3-trimethyl-3,4-dihydro-1H-quinoxalin-2-one, 7-(4-cyclopentylsulfonyloxy-2-methoxyphenyl)-8-(5-methylthiophen-2-ylcarbonyloxymethyl)-1,3,3-trimethyl-3,4-dihydro-1H-quinoxalin-2-one, 7-(2-methoxy-4-methylsulfonyloxyphenyl)-8-(2-methoxyphenylaminomethyl)-1,3,3-trimethyl-3,4-dihydro-1H-quinoxalin-2-one, 7-(4-cyclopropylsulfonyloxy-2-methoxyphenyl)-8-(2-methoxyphenylaminomethyl)-1,3,3-trimethyl-3,4-dihydro-1H-quinoxalin-2-one, 7-(2-methoxy-4-methylsulfonyloxyphenyl)-8-(2-methoxy-5-nitrophenoxymethyl)-1,3,3-trimethyl-3,4-dihydro-1H-quinoxalin-2-one, 8-(2-methoxy-5-nitrophenoxymethyl)-7-[2-methoxy-4-(3,3,3-trifluoropropylsulfonyloxy)phenyl]-1,3,3-trimethyl-3,4-dihydro-1H-quinoxalin-2-one, 7-(4-isopropylsulfonyloxy-2-methoxyphenyl)-8-(2-methoxy-5-nitrophenoxymethyl)-1,3,3-trimethyl-3,4-dihydro-1H-quinoxalin-2-one, 7-(4-cyclopropylsulfonyloxy-2-methoxyphenyl)-8-(2-methoxy-5-nitrophenoxymethyl)-1,3,3-trimethyl-3,4-dihydro-1H-quinoxalin-2-one, 7-(4-cyclopropylsulfonyloxy-2-methoxyphenyl)-8-(2-methyl-5-nitrophenoxymethyl)-1,3,3-trimethyl-3,4-dihydro-1H-quinoxalin-2-one, 7-[2-methoxy-4-(3,3,3-trifluoropropylsulfonyloxy)phenyl]-8-(2-methyl-5-nitrophenoxymethyl)-1,3,3-trimethyl-3,4-dihydro-1H-quinoxalin-2-one, 7-(2-methoxy-4-methylsulfonyloxyphenyl)-8-(2-methyl-5-nitrophenoxymethyl)-1,3,3-trimethyl-3,4-dihydro-1H-quinoxalin-2-one, 7-(2-methoxy-4-propylsulfonyloxyphenyl)-8-(4-methylbenzoyloxymethyl)-1,3,3-trimethyl-3,4-dihydro-1H-quinoxalin-2-one, 8-(2-methoxyphenylaminomethyl)-7-[2-methoxy-4-(3,3,3-trifluoropropylsulfonyloxy)phenyl]-1,3,3-trimethyl-3,4-dihydro-1H-quinoxalin-2-one, 7-(4-isobutylsulfonyloxy-2-methoxyphenyl)-8-(2-methoxyphenylaminomethyl)-1,3,3-trimethyl-3,4-dihydro-1H-quinoxalin-2-one, 7-(4-cyclopropylsulfonyloxy-2-methoxyphenyl)-8-(5-fluoro-2-methylphenylaminomethyl)-1,3,3-trimethyl-3,4-dihydro-1H-quinoxalin-2-one, 8-(5-fluoro-2-methylphenylaminomethyl)-7-[2-methoxy-4-(3-propylsulfonyloxy)phenyl]-1,3,3-trimethyl-3,4-dihydro-1H-quinoxalin-2-one, 7-(4-benzylaminopropylsulfonyloxy-2-methoxyphenyl)-8-(5-fluoro-2-methylphenoxymethyl)-1,3,3-trimethyl-3,4-dihydro-1H-quinoxalin-2-one, 8-(5-fluoro-2-methylphenoxymethyl)-7-(2-methoxy-4-propylaminopropylsulfonyloxyphenyl)-1,3,3-trimethyl-3,4-dihydro-1H-quinoxalin-2-one, 8-(5-fluoro-2-methylphenoxymethyl)-7-[2-methoxy-4-(morpholin-4-yl)propylsulfonyloxyphenyl]-1,3,3-trimethyl-3,4-dihydro-1H-quinoxalin-2-one, 8-(5-fluoro-2-methylphenoxymethyl)-7-[2-methoxy-4-(piperidin-1-yl)chloropropylsulfonyloxyphenyl]-1,3,3-trimethyl-3,4-dihydro-1H-quinoxalin-2-one, 8-(5-fluoro-2-methylphenoxymethyl)-7-[2-methoxy-4-(N-dimethylaminoethyl-N-methyl)aminopropylsulfonyloxy phenyl]-1,3,3-trimethyl-3,4-dihydro-1H-quinoxalin-2-one, and 8-(5-fluoro-2-methylphenoxymethyl)-7-[2-methoxy-4-(N-methyl-N-methylaminoethyl)aminopropylsulfonyloxy phenyl]-1,3,3-trimethyl-3,4-dihydro-1H-quinoxalin-2-one.

* * * * *